United States Patent
McElroy et al.

(10) Patent No.: US 8,252,791 B2
(45) Date of Patent: Aug. 28, 2012

(54) PURINE COMPOUNDS AS CANNABINOID RECEPTOR BLOCKERS

(75) Inventors: John F. McElroy, Wilmington, DE (US); Robert J. Chorvat, West Chester, PA (US)

(73) Assignee: Jenrin Discovery, Inc., Wilmington, DE (US)

( * ) Notice: Subject to any disclaimer, the term of this patent is extended or adjusted under 35 U.S.C. 154(b) by 387 days.

(21) Appl. No.: 12/540,425

(22) Filed: Aug. 13, 2009

(65) Prior Publication Data

US 2010/0041650 A1 Feb. 18, 2010

Related U.S. Application Data

(60) Provisional application No. 61/088,377, filed on Aug. 13, 2008.

(51) Int. Cl.
*C07D 473/34* (2006.01)
*C07D 473/16* (2006.01)
*A61K 31/52* (2006.01)
*A61P 3/06* (2006.01)
*A61P 3/10* (2006.01)
*A61P 3/04* (2006.01)

(52) U.S. Cl. .............. 514/234.2; 514/252.16; 514/263.2; 514/263.22; 544/118; 544/277

(58) Field of Classification Search .................. 544/118, 544/277; 514/234.2, 252.16, 263.2, 263.22
See application file for complete search history.

(56) References Cited

U.S. PATENT DOCUMENTS

| 7,129,239 | B2 | 10/2006 | Griffith et al. |
| 2005/0043327 | A1* | 2/2005 | Coe et al. ................. 514/263.22 |
| 2006/0241120 | A1 | 10/2006 | Griffith |
| 2006/0270655 | A1* | 11/2006 | Swick et al. ............. 514/210.21 |
| 2008/0097097 | A1* | 4/2008 | Ragan ........................... 544/277 |
| 2008/0200510 | A1* | 8/2008 | Milosavljevic-Ristic ..... 514/326 |
| 2012/0071490 | A1* | 3/2012 | Dally et al. ............. 514/252.16 |

OTHER PUBLICATIONS

Yang et al., Journal of Combinatorial Chemistry (2005), 7(3), 474-482.*
Liu et al., J. Comb. Chem., 2005, 7 (4), pp. 627-636.*
Montero, C. et. al., Homology models of the cannabinoid CB1 and CB2 receptors. A docking analysis study, Europ. J. Med. Chem. 2005, 40, 75-83.
Deveaux, V. et. al., Cannabinoid CB2 Recepto Potentiates Obesity-Associate Inflammation, Insulin Resistance and Hepatic Steatosis, PLoS ONE 2009, 4(6) e5844 (www.plosone.org).

* cited by examiner

*Primary Examiner* — Mark Berch
(74) *Attorney, Agent, or Firm* — Vance Intellectual Property, PC

(57) ABSTRACT

The present invention relates to purine-based cannabinoid receptor blockers and pharmaceutical compositions thereof and methods of using the same for treating obesity, diabetes, dyslipidemias, cardiovascular disorders, inflammatory disorders, hepatic disorders, and a combination thereof.

30 Claims, No Drawings

PURINE COMPOUNDS AS CANNABINOID RECEPTOR BLOCKERS

CROSS-REFERENCE TO RELATED APPLICATIONS

The present application claims priority benefit under 35 U.S.C. §119(e) of U.S. Provisional Patent Application Ser. No. 61/088,377 filed 13 Aug. 2008. The disclosure this application is incorporated herein by reference.

FIELD OF THE INVENTION

The present invention provides purine-based cannabinoid receptor blockers and pharmaceutical compositions thereof and methods of using the same for treating obesity, diabetes, dyslipidemia, cardiovascular disorders, inflammatory disorders, and/or hepatic disorders.

BACKGROUND OF THE INVENTION

Obesity is associated with an increase in the overall amount of adipose tissue (i.e., body fat), especially adipose tissue localized in the abdominal area. Obesity has reached epidemic proportions in the United States. The prevalence of obesity has steadily increased over the years among all racial and ethnic groups. The most recent data from the Centers for Disease Control and Prevention, and the National Center for Health Statistics report 66% of the adult population overweight (BMI, 25.0-29.9), 31% obese (BMI, 30-39.9), and 5% extremely obese (BMI, ≧40.0). Among children aged 6 through 19 years, 32% were overweight and 17% were obese. This translates to 124 million Americans medically overweight, and 44 million of these deemed obese. Obesity is responsible for more than 300,000 deaths annually, and will soon overtake tobacco usage as the primary cause of preventable death in the United States. Obesity is a chronic disease that contributes directly to numerous dangerous co-morbidities, including type 2 diabetes, cardiometabolic diseases fatty liver diseases, cardiovascular disease, inflammatory diseases, premature aging, and some forms of cancer. Type 2 diabetes, a serious and life-threatening disorder with growing prevalence in both adult and childhood populations, is currently the $7^{th}$ leading cause of death in the United States. Since more than 80% of patients with type 2 diabetes are overweight, obesity is the greatest risk factor for developing type 2 diabetes. Increasing clinical evidence indicates that the best way to control type 2 diabetes is to reduce weight.

The most popular over-the counter drugs for the treatment of obesity, phenylpropanolamine and ephedrine, and the most popular prescription drug, fenfluramine, were removed from the marketplace as a result of safety concerns. Drugs currently approved for the long-term treatment of obesity fall into two categories: (a) CNS appetite suppressants such as sibutramine and rimonabant, and (b) gut lipase inhibitors such as orlistat. CNS appetite suppressants reduce eating behavior through activation of the 'satiety center' in the brain and/or by inhibition of the 'hunger center' in the brain. Gut lipase inhibitors reduce the absorption of dietary fat from the gastrointestinal (GI) tract. Although appetite suppressants and gut lipase inhibitors work through very different mechanisms, they share in common the same overall goal of reducing body weight secondary to reducing the amount of calories that reach the systemic circulation. Unfortunately, these indirect therapies produce only a modest initial weight loss (approximately 5% compared to placebo) that is usually not maintained. After one or two years of treatment, most patients return to or exceed their starting weight. In addition, most approved anti-obesity therapeutics produce undesirable and often dangerous side effects that can complicate treatment and interfere with a patient's quality of life.

The lack of therapeutic effectiveness, coupled with the spiraling obesity epidemic, positions the 'treatment of obesity' as one of the largest and most urgent unmet medical needs. There is, therefore, a real and continuing need for the development of improved medications that treat or prevent obesity.

The endocanabinoid system, comprised of the canabinoid receptors (CB1 and CB2) and their endogenous ligands (e.g., anandamide, 2-AG), plays a prominent role in the control of food intake and energy metabolism. CB1 receptors are widely expressed in the brain, including cortex, hippocampus, amygdala, pituitary and hypothalamus. CB1 receptors have also been identified in numerous peripheral organs and tissues, including thyroid gland, adrenal gland, reproductive organs, adipose tissue, liver, muscle, pancreas, and gastrointestinal tract. CB2 receptors are localized almost exclusively in immune and blood cells (*Endocrine Reviews* 2006, 27, 73)

The plant-derived cannabinoid agonist $\Delta^9$-tetrahydrocannabinol ($\Delta^9$-THC), the main psychoactive component of marijuana, binds to both CB1 and CB2 receptors. $\Delta^9$-THC is widely reported to increase appetite and food intake (hyperphagia) in humans and in animals. This hyperphagic effect is largely blocked by pretreatment with selective CB1 receptor blockers (i.e., CB1 blockers)(e.g., rimonabant (SR141716A, Acomplia®)), strongly supporting the belief that CB1 receptor activation mediates the hyperphagic effect of $\Delta^9$-THC, (*Endocrine Reviews* 2006, 27, 73).

In humans, rimonabant produces a clinically meaningful weight loss in obese patients. Obese patients also experience improvements in diabetic and cardiometabolic risk factors associated with obesity, including an increase in the level of high density lipoprotein cholesterol (HDL), and decreases in triglycerides, glucose, and hemoglobin A1c (HbA1c, a marker of cumulative exposure to glucose) levels. Rimonabant also produces greater reductions in abdominal fat deposits, which are a known risk factor for diabetes and heart disease (*Science* 2006, 311, 323). Taken together, these improvements in adiposity and cardiometabolic risk factors produce an overall decrease in the prevalence of the metabolic syndrome) *Lancet* 2005, 365, 1389 and *NEJM* 2005, 353, 2121).

In patients with type 2 diabetes not currently treated with other anti-diabetic medications, rimonabant was shown to significantly improve blood sugar control and weight, as well as other risk factors such as HDL and triglycerides, when compared to placebo (International Diabetes Federation World Diabetes Congress, Cape Town, South Africa, 2006). After six months of treatment, HbA1c levels were significantly lowered by 0.8% from a baseline value of 7.9 as compared to a reduction of 0.3% in the placebo group. These results are consistent with preclinical studies that deomostrate improved glycemic and lipid control in diabetic and dyslipedemic mice, rats, and dogs (*Pharmacology Biochemistry & Behavior,* 2006, 84, 353; *American Journal of Physiology,* 2003, 284, R345; *American Diabetes Association Annual Meeting,* 2007; Abstract Number 0372-OR).

Several studies have conclusively demonstrated that a chronic low-grade systemic inflammatory state, predominantly arising from adipose tissue and liver, plays a critical role in the development of obesity-related comorbidities. Thus, in adipose tissue, fat laden adipocytes initiate the inflammatory response by producing cytokines and chemokines, including TNFα. Increased adipose tissue inflammation will contribute to insulin resistance, leading to increased delivery of free fatty acids to the liver, and thereby contributing to hepatic steatosis. Moreover, fatty liver itself also induces a local subacute inflammatory state characterized by production of inflammatory mediators such as TNFa or IL-6. Preclinical studies have demonstrated the critical role of CB receptors in the inflammatory process associated with rheumatoid arthritis, inflammatory bowel diseases, atherosclerosis and liver ischemia-reperfusion injury to the liver. Moreover, fatty liver itself also induces a local subacute inflammatory state characterized by production of inflammatory mediators such as TNFa or IL-6, that directly contribute to hepatic and systemic insulin resistance (*PlosOne*, 2009, 4, E5844).

The beneficial effects of rimonabant on diabetic and cardiometabolic risk factors such as high blood pressure, insulin resistance, and eleveated triglycerides cannot be explained by diet-related weight loss alone. For example, in patients receiving 20 mg of rimonabant, only approximately 50% of the beneficial effects on triglycerides, fasting insulin, and insulin resistance can be accounted for by weight loss secondary to reduced food intake. These results suggest a direct pharmacological effect of CB1 antagonists on glucose and lipid metabolism, in addition to indirect effects on metabolism secondary to hypophagia-mediated weight loss (*Science* 2006, 311, 323 and *JAMA* 2006, 311, 323). Taken together, these results suggest that CB1 antagonists might be effective in the treatment of diabetes, dyslipidemia, cardiovascular disorders (e.g., atherosclerosis, hypertension), and hepatic disorders (e.g., cirrhosis, fatty liver diseases), even in patients that are not clinically overweight or obese.

The CB1 receptor is one of the most abundant and widely distributed G protein-coupled receptors in the mammalian brain. It is believed that the appetite-suppressant properties of CB1 antagonists are mediated through an interaction with CB1 receptors in the hypothalamus (regulation of food intake), and in the mesolimbic region (rewarding properties of food). However, CB1 receptors are far more broadly distributed in brain (e.g., neocortex, hippocampus, thalamus, cerebellum, and pituitary), and while interacting with targeted CB1 receptors in hypothalamus and mesolimbic regions to suppress appetite, CB1 antagonists have equal access to non-targeted CB1 receptors that have little if any role in appetite control. Binding to non-targeted receptors can often lead to unwanted side effects of CNS drugs (*Endocrine Reviews* 2006, 27: 73). The CB1 blockers rimonabant and taranabant produce psychiatric and neurological side effects. These include depressed mood, anxiety, irritability, insomnia, dizziness, and headache, seizures, and suicidality.

These side effects are dose-related and appear pronounced at the most efficacious weight-reducing doses of rimonabant and taranabant (*JAMA* 2006, 311, 323; *Cell Metabolism* 2008, 7, 68). The occurrence of therapeutic efficacy (appetite suppression) and side effects over the same dose range strongly suggest that both effects are mediated through concurrent antagonism of CB1 receptors in both 'targeted' and 'non-targeted' brain regions. Brain-penetrant CB1 blockers do not selectively target CB1 receptors in efficacy brain regions, while ignoring CB1 receptors in side effect brain regions.

The beneficial effects of the CB1 antagonist rimonabant on body weight, adiposity, and diabetic and cardiometabolic risk factors such as high blood pressure, insulin resistance and blood lipids cannot be explained by weight loss derived from CNS-mediated appetite suppression alone (*JAMA* 2006, 311, 323). Approximately 50% of the non-CNS benefit is likely derived from an interaction with CB1 receptors in peripheral tissues known to play an active role in metabolism. These include adipose tissue, liver, muscle, pancreas, and gastrointestinal tract.

U.S. Pat. No. 7,129,239 describes purine compounds of the following formula:

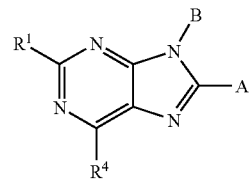

wherein A and B can be aryl or heteroaryl and $R^4$ can be a carbon- or nitrogen-linked ring. These compounds are described as being cannabinoid receptor ligands (e.g., CB1 antagonists) and being potentially useful for treating a wide variety of disorders via a central nervous system (CNS) mechanism (e.g., acting as an appetite suppressant). Thus, these compounds appear to have been optimized for maximal brain penetrance and maximal accumulation in the brain.

In view of the above, it is highly desirable to find effective and highly selective CB1 receptor blockers with limited or no CNS adverse side effects, including mood disorders. Particularly, it is desirable to find compounds that preferentially target CB1 receptors in peripheral tissues (e.g., adipose tissue, liver, muscle, pancreas, and gastrointestinal tract), while sparing CB1 receptors in brain. In this way, peripherally-mediated beneficial effects of CB1 blockers should be maintained, whereas CNS side effects should be reduced or eliminated. This should provide a novel opportunity to develop safer alternatives to highly brain penetrant CB1 blockers for the prevention or treatment of obesity, diabetes, dyslipidemia, cardiovascular disorders, inflammatory disorders, and/or hepatic disorders.

SUMMARY OF THE INVENTION

Accordingly, in an aspect, the present invention provides novel purine derivatives or pharmaceutically acceptable salts thereof that are CB1 receptor blockers.

In another aspect, the present invention provides novel pharmaceutical compositions, comprising: a pharmaceutically acceptable carrier and a therapeutically effective amount of at least one of the compounds of the present invention or a pharmaceutically acceptable salt form thereof.

In another aspect, the present invention provides novel methods for treating obesity, diabetes (e.g., insulin resistance, inadequate glucose tolerance, Type I diabetes, and Type II diabetes), dyslipidemias (e.g., elevated triglyerides and LDL, and low HDL), cardiovascular disorders (e.g., atherosclerosis and hypertension), inflammatory disorders (e.g., inflammatory bowel disease, Alzheimer's disease, atherosclerosis, osteoperosis, multiple sclerosis, traumatic brain injury, arthritis, and neuropathic pain), and/or hepatic disorders (e.g., nonalcoholic steatohepatitis (NASH), cirrhosis and fatty liver disease), comprising: administering to a mammal in need of such treatment a therapeutically effective amount of at least one of the compounds of the present invention or a pharmaceutically acceptable salt form thereof.

In another aspect, the present invention provides processes for preparing novel compounds.

In another aspect, the present invention provides novel compounds or pharmaceutically acceptable salts for use in therapy.

In another aspect, the present invention provides the use of novel compounds for the manufacture of a medicament for the treatment of obesity, diabetes, dyslipidemias, cardiovascular disorders, inflammatory disorders, and/or hepatic disorders.

These and other objects, which will become apparent during the following detailed description, have been achieved by the inventors' discovery that the presently claimed compounds or pharmaceutically acceptable salt forms thereof are expected to be effective CB1 receptor blockers.

DETAILED DESCRIPTION OF THE INVENTION

All references cited herein are hereby incorporated in their entirety herein by reference.

A CB1 blocker is a neutral CB1 receptor antagonist and/or an inverse CB1 receptor agonist.

The present invention is based on the finding that a CB1 receptor blocker has beneficial effects on metabolic disorders including obesity, diabetes, dyslipidemias, cardiovascular, inflammatory, and hepatic diseases that cannot be explained by weight loss derived from CNS-mediated appetite suppression alone, and that this effect is mediated, at least in part, through interaction at peripheral CB1 receptors. To this end, the present invention provides compounds that are designed to preferentially target CB1 receptors in peripheral tissues (e.g., adipose tissue, liver, muscle, pancreas, and gastrointestinal tract), while sparing CB1 receptors in brain. With these types of compounds, peripherally-mediated beneficial effects of CB1 blockers should be maintained, whereas CNS side effects should be reduced or eliminated.

The compounds of the present invention have been designed to have reduced CNS exposure by virtue of their inability or limited ability to penetrate the blood-brain barrier (BBB), or by their participation in active transport systems, thus reducing centrally mediated side-effects, a potential problem with many anti-obesity agents. It is expected that the peripherally restricted compounds of the present invention will have no or very limited CNS effects, including mood disorders, seizures, and suicidality. Thus, their peripherally mediated CB1 blocking properties should provide therapeutic agents with greater safety.

Moreover, if the maximum dosage of a drug used in the treatment of obesity, diabetes, dyslipidemias, cardiovascular disorders, inflammatory disorders, and/or hepatic disorders is limited as a result of CNS side effects (e.g., seizures, depression, anxiety, suicidality, movement disorders, and hyperactivity), incorporation of a peripherally restricting group in such a drug would lower the brain concentration of the drug relative to the concentration in the systemic circulation, thereby affording the opportunity to increase the dosage employed to treat the peripheral disorder (e.g., obesity, diabetes, dyslipidemias, cardiovascular disorders, inflammatory disorders, and/or hepatic disorders). The increased dosage may provide greater therapeutic efficacy, as well as a more rapid onset of therapeutic action.

Thus, in an embodiment, the present invention provides novel compounds of formula AA or a stereoisomer or pharmaceutically acceptable salt thereof:

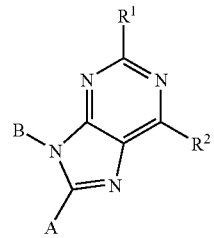

AA wherein:

A and B are independently selected from aryl and heteroaryl, wherein A and B are independently substituted with 0-3 $A^1$;

$A^1$ at each occurrence is independently selected from halo, —CN, OH, $C_{1-6}$ alkyl, $C_{2-6}$ alkenyl, $C_{3-8}$ cycloalkyl, 3-8 membered heterocycle, $C_{1-6}$ alkoxy, aryloxy, $C_{1-6}$ acyl, $C_{1-6}$ acyloxy, $C_{1-6}$ alkyl-OC(O)—, $C_{1-4}$ alkyl-NHC(O)—, ($C_{1-4}$ alkyl)$_2$NC(O), $NH_2$, $C_{1-6}$ alkylamino-, ($C_{1-4}$ alkyl)$_2$amino-, $C_{3-6}$ cycloalkylamino-, $C_{1-6}$ acylamino-, aryl$C_{1-4}$ alkylamino-, heteroaryl$C_{1-4}$ alkylamino-, aryl, and heteroaryl, wherein the aryl and heteroaryl groups are further substituted with 0-2 groups selected from halo, —CN, OH, $C_{1-6}$ alkyl, $C_{2-6}$ alkenyl, $C_{1-6}$ alkoxy, $C_{1-6}$ acyl, $C_{1-6}$ acyloxy, $C_{1-6}$ alkyl-OC(O)—, $C_{1-4}$ alkyl-NHC(O)—, ($C_{1-4}$ alkyl)$_2$NC(O), $NH_2$, $C_{1-6}$ alkylamino-, ($C_{1-4}$ alkyl)$_2$amino-, and $C_{1-6}$ acylamino-;

X is selected from a bond, —$CH_2CH_2$— and —$C(R^{4a})(R^{4b})$—;

Y is selected from O, S, $NR^{5c}$, C(O), C=NOH, and —$C(R^{5a})(R^{5b})$—;

Z is selected from a bond, —$CH_2CH_2$— and —$C(R^{4c})(R^{4d})$—;

$R^1$ is selected from H, $C_{1-4}$ alkyl, $C_{1-4}$ haloalkyl, and $C_{1-4}$ alkoxy;

$R^2$ is selected from a group having Formula (1A) and (1B)

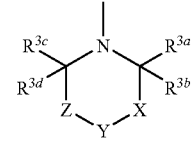

1A

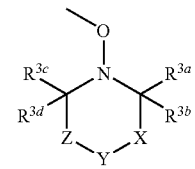

1B $R^{3a}$, $R^{3b}$, $R^{3c}$, $R^{3d}$, $R^{4a}$, $R^{4b}$, $R^{4c}$, $R^{4d}$, $R^{5a}$, and $R^{5b}$ are each independently selected from H, cyano, OH, $NH_2$, $H_2NC(O)$—, $C_{1-6}$ alkyl, $C_{1-6}$ alkoxy, $C_{1-6}$ acyloxy, $C_{1-6}$ acyl, $C_{1-3}$ alkyl-OC(O)—, $C_{1-4}$ alkyl-NHC(O)—, ($C_{1-4}$ alkyl)$_2$NC(O), $C_{1-6}$ alkylamino-, ($C_{1-4}$ alkyl)$_2$amino-, $C_{3-6}$ cycloalkylamino-, $C_{1-6}$ acylamino-, aryl$C_{1-4}$ alkylamino-, heteroaryl$C_{1-4}$ alkylamino-, aryl, heteroaryl, a 3-6 membered heterocycle, and a 3-8 membered carbocyclic ring, wherein the alkyl, cycloalkyl, aryl, heterocycle, and heteroaryl groups are independently optionally substituted with 0-2 $R^6$ groups;

alternatively, $R^{5a}$ and $R^{5b}$ taken together form a ring selected from a 3-6 membered heterocyclic ring, a 5-6 membered lactone ring, and a 4-6 membered lactam ring, wherein the ring is substituted with 0-2 $R^6$ and the lactone ring and the lactam ring optionally contain an additional heteroatom selected from O, N, NH, and S;

$R^{5c}$ is selected from H, $C_{1-6}$ alkyl, $C_{3-6}$ cycloalkyl, $C_{1-3}$ alkylsulfonyl-, $C_{1-3}$ alkylaminosulfonyl-, di$C_{1-3}$ alkylaminosulfonyl-, $C_{1-6}$ acyl, $C_{1-6}$ alkyl-OC(O)—, aryl, and heteroaryl, wherein the alkyl, aryl, and heteroaryl groups are substituted with 0-2 $R^6$;

$R^6$ at each occurrence is independently selected from halo, —CN, OH, $C_{1-6}$ alkyl, $C_{2-6}$ alkenyl, $C_{3-8}$ cycloalkyl, 3-8 membered heterocycle, $C_{1-6}$ alkoxy, aryloxy, $C_{1-6}$ acyl, $C_{1-6}$ acyloxy, $C_{1-6}$ alkyl-OC(O)—, $C_{1-4}$ alkyl-NHC(O)—, ($C_{1-4}$ alkyl)$_2$NC(O), $NH_2$, $C_{1-6}$ alkylamino-, ($C_{1-4}$ alkyl)$_2$amino-, $C_{3-6}$ cycloalkylamino-, $C_{1-6}$ acylamino-, aryl$C_{1-4}$ alkylamino-, heteroaryl$C_{1-4}$ alkylamino-, aryl, and heteroaryl, wherein the aryl and heteroaryl groups are further substituted with 0-2 groups selected from halo, —CN, OH, $C_{1-6}$ alkyl, $C_{2-6}$ alkenyl, $C_{1-6}$ alkoxy, $C_{1-6}$ acyl, $C_{1-6}$ acyloxy, $C_{1-6}$ alkyl-OC(O)—, $C_{1-4}$ alkyl-NHC(O)—, ($C_{1-4}$ alkyl)$_2$NC(O), $NH_2$, $C_{1-6}$ alkylamino-, ($C_{1-4}$ alkyl)$_2$amino-, and $C_{1-6}$ acylamino-;

alternatively, $R^{3a}$ and $R^{3b}$ taken together with $R^{3c}$ and $R^{3d}$ forms a bond, a methylene bridge, or an ethylene bridge;

alternatively, $R^{4a}$ and $R^{4b}$ taken together with $R^{3c}$ and $R^{3d}$ forms a bond, a methylene bridge, or an ethylene bridge;

alternatively, either $R^{4c}$ and $R^{4d}$ taken together with $R^{4a}$ and $R^{4b}$ or with $R^{3a}$ and $R^{3b}$ forms a bond, a methylene bridge, or an ethylene bridge;

provided that at least one of A, B, $R^1$, $R^2$, $R^{3a}$, $R^{3b}$, $R^{3c}$, $R^{3d}$, $R^{4a}$, $R^{4b}$, $R^{4c}$, $R^{4d}$, $R^{5a}$, $R^{5b}$ and $R^{5c}$ is suitably modified or replaced by a group capable of reducing or limiting the CNS (brain) levels of compound AA.

In another embodiment, when $R^3$ or $R^4$ is a group of Formula (IA), then (a) at least one of $R^{3a}$, $R^{3b}$, $R^{3c}$, $R^{3d}$, $R^{4a}$, $R^{4b}$, $R^{4c}$, and $R^{4d}$ is other than H, $C_{1-4}$ alkyl, or $C_{1-4}$ haloalkyl; and (b) when X and Z are a bond, —$CH_2$— or —$CH_2CH_2$— and $R^{3a}$, $R^{3b}$, $R^{3c}$, and $R^{3d}$ are hydrogen, then Y is other than O, sulfur or —NH—.

It is noted that if a substituent is listed for an alkyl moiety of a variable, this includes the alkyl portions of other groups, including alkoxy and acyl.

[1] In another embodiment, the present invention provides novel compounds of formula I or a stereoisomer or pharmaceutically acceptable salt thereof:

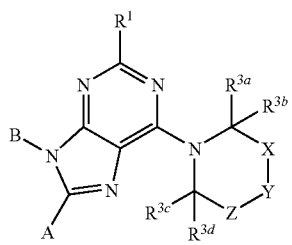

I wherein:

A and B are independently selected from aryl and heteroaryl, wherein A and B are independently substituted with 0-3 groups independently selected from, $C_{1-4}$ alkoxy, $C_{1-4}$ alkyl, $C_{1-4}$ haloalkyl, cyano, $RO_2C(CH_2)_mCHQ(CH_2)_mNHC(O)(CH_2)_m$—, $R^c_2NC(O)(CH_2)_mCHQ(CH_2)_mNHC(O)(CH_2)_m$—, $RO_2C(CH_2)_mCHQ(CH_2)_mNHC(O)(CH_2)_mCHQ(CH_2)_mNHC(O)(CH_2)_m$—, $R^c_2NC(O)(CH_2)_mCHQ(CH_2)_mNHC(O)(CH_2)_mCHQ(CH_2)_mNHC(O)(CH_2)_m$—, $(CH_2)_mCO_2R$, $O(CH_2)_nCO_2R$, $OCH_2CH=CHCO_2R$, $CH_2O(CH_2)_nCO_2R$, $CH_2OCH_2CH=CHCO_2R$, $O(CH_2)_nPO(OR)_2$, $CH_2O(CH_2)_nPO(OR)_2$, $NR^a(CH_2)_mCO_2R$, $NR^a(CH_2)_nPO(OR)_2$, $NR^aCH_2CH=CHCO_2R$, $NR^aSO_2CH_3$, $NR^aCO(CH_2)_nCO_2R$, $O(CH_2)_nC_6H_4CO_2R$, $O(CH_2)_nC_6H_4(CH_2)_nCO_2R$, $CH_2O(CH_2)_nC_6H_4CO_2R$, $O(CH_2)_nC_6H_4CONR^c_2$, $O(CH_2)_nC_6H_4(CH_2)_nCONR^c_2$, $CH_2O(CH_2)_nC_6H_4CONR^c_2$, $O(CH_2)_nC_6H_4$-tetrazole, $CH_2O(CH_2)_nC_6H_4$-tetrazole, $O(CH_2)_nC_6H_4(CH_2)_n$-tetrazole, $NR^a(CH_2)_nC_6H_4CO_2R$, $CH_2NR^a(CH_2)_nC_6H_4CO_2R$, $NR^a(CH_2)_nC_6H_4CONR^c_2$, $CH_2NR^a(CH_2)_nC_6H_4CONR^c_2$, $NR^a(CH_2)_nC_6H_4$-tetrazole, $CH_2NR^a(CH_2)_nC_6H_4$-tetrazole, —CN, $(CH_2)_mC(=NH)NH_2$, $(CH_2)_mNHC(=NH)NH_2$, $(CH_2)_mNHC(=CHNO_2)NH_2$, $(CH_2)_mNHC(=NCN)NH_2$, $CONR^c_2$, $(CH_2)_nCONR^c_2$, $O(CH_2)_nCONR^c_2$, $CH_2O(CH_2)_nCONR^c_2$, $NR^a(CH_2)_mCONHR^a$, $OCH_2CH=CHCONR^c_2$, $CH_2OCH_2CH=CHCONR^c_2$, $NR^aCH_2CH=CHCONR^c_2$, tetrazole, $O(CH_2CH_2O)_pR$, $NR^a(CH_2CH_2O)_pR$, $SONH_2$, and $SO_2NR^aCH_3$;

X is selected from a bond, —$CH_2CH_2$— and —$C(R^{4a})(R^{4b})$—;

Y is selected from O, S, $NR^{5c}$, C(O), C=NOH, and —$C(R^{5a})(R^{5b})$—;

Z is selected from a bond, —$CH_2CH_2$— and —$C(R^{4c})(R^{4d})$—;

$R^1$ is selected from H, $C_{1-4}$ alkyl, $C_{1-4}$ haloalkyl, $C_{1-4}$ alkylene-OH, $C_{1-4}$ alkoxy, $(CH_2)_nCO_2R$, $RO_2C(CH_2)_mCHQ(CH_2)_mNHC(O)(CH_2)_n$—, $R^c_2NC(O)(CH_2)_mCHQ(CH_2)_mNHC(O)(CH_2)_n$—, $OCH_2CH=CHCO_2R$, $CH_2O(CH_2)_nCO_2R$, $CH_2OCH_2CH=CHCO_2R$, $O(CH_2)_nPO(OR)_2$, $CH_2O(CH_2)_nPO(OR)_2$, $NR^a(CH_2)_mCO_2R$, $NR^a(CH_2)_nPO(OR)_2$, $NR^aCH_2CH=CHCO_2R$, $NR^aSO_2CH_3$, $NR^aCO(CH_2)_nCO_2R$, $(CH_2)_mNHC(=NH)NH_2$, $(CH_2)_mNHC(=CHNO_2)NH_2$, $(CH_2)_mNHC(=NCN)NH_2$, $(CH_2)_nCONR^c_2$, $O(CH_2)_nCONR^c_2$, $CH_2O(CH_2)_nCONR^c_2$, $(CH_2)_mNR^a(CH_2)_nCONHR^a$, $(CH_2)_mNR^aC(O)(CH_2)_nCO_2R$, $(CH_2)_mNR^aC(O)(CH_2)_nCONR^c_2$, $(CH_2)_mNR^a(CH_2)_mCHQCO_2R$, $(CH_2)_mNR^a(CH_2)_mCHQCONR^c_2$, $(CH_2)_nCH(NHR^a)CO_2R$, $(CH_2)_nCH(NHR^a)CONHR^a$, $CH_2OCH_2CH=CHCONR^c_2$, $NR^aCH_2CH=CHCONR^c_2$, and $(CH_2)_m$tetrazole, $R^{3a}$, $R^{3b}$, $R^{3c}$, $R^{3d}$, $R^{4a}$, $R^{4b}$, $R^{4c}$, $R^{4d}$, $R^{5a}$, and $R^{5b}$ are each independently selected from H, cyano, OH, $NH_2$, $H_2NC(O)$—, $C_{1-6}$ alkyl, $C_{1-6}$ alkoxy, $C_{1-6}$ acyloxy, $C_{1-6}$ acyl, $C_{1-3}$ alkyl-OC(O)—, $C_{1-4}$ alkyl-NHC(O)—, ($C_{1-4}$ alkyl)$_2$NC(O)—, $C_{3-8}$ cycloalkyl, $RO_2C(CH_2)_mCHQ(CH_2)_m$—, $R_2N(O)C(CH_2)_mCHQ(CH_2)_m$—, $R_2NS(O_2)C(CH_2)_mCHQ(CH_2)_m$—, $RO_2C(CH_2)_mCHQ(CH_2)_mNHC(O)$—, $R^c_2NC(O)(CH_2)_mCHQ(CH_2)_mNHC(O)$—, $RO_2C(CH_2)_mCHQ(CH_2)_m NHC(O)(CH_2)_mCHQ(CH_2)_mNHC(O)$—, $R^c_2NC(O)(CH_2)_mCHQ(CH_2)_mNHC(O)(CH_2)_mCHQ(CH_2)_mNHC(O)$—, $RO_2C(CH_2)_mCHQ(CH_2)_mNHC(O)(CH_2)_mCHQ(CH_2)_mNHC(O)(CH_2)_mCHQ(CH_2)_mNHC(O)$—, $R^c_2NC(O)(CH_2)_mCHQ(CH_2)_mNHC(O)(CH_2)_mCHQ(CH_2)_mNHC(O)(CH_2)_mCHQ(CH_2)_mNHC(O)$—, $ROS(O_2)(CH_2)_mCHQ(CH_2)_mNHC(O)$—, $R^c_2NS(O_2)(CH_2)_mCHQ(CH_2)_mNHC(O)$—, $C_{1-6}$ alkylamino-, ($C_{1-4}$ alkyl)$_2$amino-, $C_{3-6}$ cycloalkylamino-, $C_{1-6}$ acylamino-, aryl$C_{1-4}$ alkylamino-, heteroaryl$C_{1-4}$ alkylamino-, aryl, heteroaryl, a 3-6 membered heterocycle, and a 3-8 membered carbocyclic ring, wherein the alkyl, cycloalkyl, aryl, heterocycle, and heteroaryl groups are substituted with 0-2 $R^6$;

alternatively, $R^{5a}$ and $R^{5b}$ taken together form a ring selected from a 3-6 membered heterocyclic ring, a 5-6 membered lactone ring, and a 4-6 membered lactam ring, wherein the ring is substituted with 0-2 $R^6$ and the lactone ring and the lactam ring optionally contain an additional heteroatom selected from O, N, NR, and S;

$R^{5c}$ is selected from H, $C_{1-6}$ alkyl, $C_{3-6}$ cycloalkyl, $C_{1-3}$ alkylsulfonyl-, $C_{1-3}$ alkylaminosulfonyl-, di$C_{1-3}$ alkylaminosulfonyl-, $C_{1-6}$ acyl, $C_{1-6}$ alkyl-OC(O)—, —$(CH_2)_mCO_2R$, —C(O)$(CH_2)_nCO_2R$, —$(CH_2)_mCONR^c_2$, —C(O)$(CH_2)_nCONR^c_2$, —$(CH_2)_mC(O)NH(CH_2)_nCO_2R$, —$(CH_2)_mC(O)NH(CH_2)_nCONR^c_2$, —C(O)$(CH_2)_nCONH(CH_2)_mCHQ(CH_2)_mCO_2R$, —C(O)$(CH_2)_nCONH(CH_2)_mCHQ(CH_2)_mCONR^c_2$, aryl, and heteroaryl, wherein the alkyl, aryl, and heteroaryl groups are substituted with 0-2 $R^6$;

$R^6$ at each occurrence is independently selected from halo, —CN, OH, $C_{1-6}$ alkyl, $C_{2-6}$ alkenyl, $C_{3-8}$ cycloalkyl, $C_{1-6}$ alkoxy, $C_{1-6}$ acyl, $C_{1-6}$ acyloxy, $C_{1-4}$ alkyl-NHC(O)—, $(C_{1-4}$ alkyl$)_2$NC(O), $NH_2$, $C_{1-6}$ alkylamino-, $(C_{1-4}$ alkyl$)_2$amino-, $C_{3-6}$ cycloalkylamino-, $C_{1-6}$ acylamino-, C(O)$NH_2$, —CONH$(CH_2)_mCHQ(CH_2)_mCO_2R$, and —CONH$(CH_2)_mCHQ(CH_2)_mCONHR$;

alternatively, $R^{3a}$ and $R^{3b}$ taken together with $R^{3c}$ and $R^{3d}$ forms a bond, a methylene bridge, or an ethylene bridge;

alternatively, $R^{4a}$ and $R^{4b}$ taken together with $R^{3c}$ and $R^{3d}$ forms a bond, a methylene bridge, or an ethylene bridge;

alternatively, either $R^{4c}$ and $R^{4d}$ taken together with $R^{4a}$ and $R^{4b}$ or with $R^{3a}$ and $R^{3b}$ forms a bond, a methylene bridge, or an ethylene bridge;

Q is selected from H, OH, $C_{1-6}$ alkyl, $C_{1-6}$ alkylene-OH, $(CH_2)_mNR^c_2$, $(CH_2)_nCONR^c_2$, $(CH_2)_mNHCONR^c_2$, $(CH_2)_mC(=NH)NH_2$, $(CH_2)_m$—$C_{3-6}$-cycloalkyl, $(CH_2)_m$-heteroaryl, and $(CH_2)_m$-aryl, wherein each aryl and heteroaryl is substituted with 0-2 groups selected from $CF_3$, halogen, $C_{1-4}$ alkyl, —CN, CONR$^c_2$, $NO_2$, $NR_2$, OR, $NHSO_2CH_3$, and SONHR;

R is independently selected from H and $C_{1-6}$ alkyl;

$R^a$ is independently selected from H, $C_{1-6}$ alkyl, $C_{2-6}$ alkenyl, and $C_{2-6}$ alkynyl;

$R^c$ is independently selected from H, OH, $C_{1-6}$ alkyl, $C_{2-6}$ alkenyl, aryl$C_{1-4}$ alkyl- and $C_{2-6}$ alkynyl, where each alkyl may be optionally substituted with a hydroxyl group on the alkyl chain, and the aryl group is optionally substituted with 0-2 groups selected from $CF_3$, halogen, $C_{1-4}$ alkyl, —CN, CONR$_2$, $NO_2$, $NR_2$, OR, $NHSO_2CH_3$, and SONHR;

m is selected from 0, 1, 2, 3, and 4; and, n is selected from 1, 2, 3, and 4.

[1a] In another embodiment, the present invention provides novel compounds, wherein A is selected from 2-chlorophenyl, 2-fluorophenyl, 2,4-dichlorophenyl, 2-fluoro-4-chlorophenyl, 2-chloro-4-fluorophenyl, and 2,4-difluorophenyl; and, B is selected from 4-chlorophenyl and 4-fluorophenyl.

[1b] In another embodiment, the present invention provides novel compounds of formula Ia or a stereoisomer or pharmaceutically acceptable salt thereof:

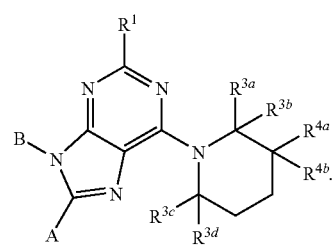

Ia

[1c] In another embodiment, the present invention provides novel compounds of formula Ia or a stereoisomer or pharmaceutically acceptable salt thereof:

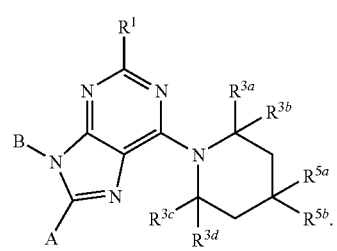

Ib

[1d] In another embodiment, the present invention provides novel compounds of formula Ia or a stereoisomer or pharmaceutically acceptable salt thereof:

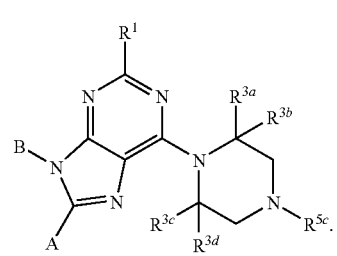

Ic

[2] In another embodiment, the present invention provides novel compounds of formula I or a stereoisomer or pharmaceutically acceptable salt thereof, wherein:

one of A and B is selected from a substituted aryl and a substituted heteroaryl, the substituent being selected from the group consisting of $CO_2R$, $RO_2C(CH_2)_mCHQ(CH_2)_mNHC(O)(CH_2)_m$—, $R^c_2NC(O)(CH_2)_mCHQ(CH_2)_mNHC(O)(CH_2)_m$—, $RO_2C(CH_2)_mCHQ(CH_2)_mNHC(O)(CH_2)_mCHQ(CH_2)_mNHC(O)(CH_2)_m$—, $R^c_2NC(O)(CH_2)_mCHQ(CH_2)_mNHC(O)(CH_2)_mCHQ(CH_2)_mNHC(O)(CH_2)_m$—, $(CH_2)_nCO_2R$, $O(CH_2)_nCO_2R$, $OCH_2CH=CHCO_2R$, $CH_2O(CH_2)_nCO_2R$, $CH_2OCH_2CH=CHCO_2R$, $O(CH_2)_nPO(OR)_2$, $CH_2O(CH_2)_nPO(OR)_2$, $NR^a(CH_2)_mCO_2R$, $NR^a(CH_2)_nPO(OR)_2$, $NR^aCH_2CH=CHCO_2R$, $NR^aSO_2CH_3$, $NR^aCO(CH_2)_nCO_2R$, $O(CH_2)_nC_6H_4CO_2R$, $O(CH_2)_nC_6H_4(CH_2)_nCO_2R$, $CH_2O(CH_2)_nC_6H_4CO_2R$, $O(CH_2)_nC_6H_4CONR^c_2$, $O(CH_2)_nC_6H_4(CH_2)_nCONR^c_2$, $CH_2O(CH_2)_nC_6H_4CONR^c_2$, $O(CH_2)_n$ $C_6H_4$-tetrazole, $CH_2O(CH_2)_nC_6H_4$-tetrazole, $O(CH_2)_n C_6H_4$ $(CH_2)_n$-tetrazole, $NR^a(CH_2)_nC_6H_4CO_2R$, $CH_2NR^a(CH_2)_n$ $C_6H_4CO_2R$, $NR^a(CH_2)_nC_6H_4CONR^c_2$, $CH_2NR^a(CH_2)_n$ $C_6H_4CONR^c_2$, $NR^a(CH_2)_nC_6H_4$-tetrazole, $CH_2NR^a(CH_2)_n$ $C_6H_4$-tetrazole, —CN, $(CH_2)_mC(=NH)NH_2$, $(CH_2)_m$ NHC $(=NH)NH_2$, $(CH_2)_m$NHC$(=CHNO_2)NH_2$, $(CH_2)_m$ NHC $(=NCN)NH_2$, $CONR^c_2$, $(CH_2)_nCONR^c_2$, $O(CH_2)_n$ $CONR^c_2$, $CH_2O(CH_2)_nCONR^c_2$, $NR^a(CH_2)_mCONHR^a$, $OCH_2CH=CHCONR^c_2$, $CH_2OCH_2CH=CHCONR^c_2$, $NR^aCH_2CH=CHCONR^c_2$, tetrazole, $O(CH_2CH_2O)_pR$, $NR^a$ $(CH_2CH_2O)_pR$, $SONH_2$, and $SO_2NR^aCH_3$;

the other of A and B is selected from an aryl and an heteroaryl, the aryl or heteroaryl being substituted with 0-3 substituents selected from halo, $C_{1-4}$ alkoxy, $C_{1-4}$ alkyl, $C_{1-4}$ haloalkyl, and cyano;

X is selected from a bond, —$CH_2CH_2$— and —$C(R^{4a})(R^{4b})$—;

Y is selected from O, S, $NR^{5c}$, C(O), C=NOH, and —$C(R^{5a})(R^{5b})$—;

Z is selected from a bond, —$CH_2CH_2$— and —$C(R^{4c})(R^{4d})$—;

$R^1$ is selected from H, $C_{1-4}$ alkyl, $C_{1-4}$ haloalkyl, and $C_{1-4}$ alkoxy;

$R^{3a}, R^{3b}, R^{3c}, R^{3d}, R^{4a}, R^{4b}, R^{4c}, R^{4d}, R^{5a}$, and $R^{5b}$ are each independently selected from H, cyano, OH, $NH_2$, $H_2NC(O)$—, $C_{1-6}$ alkyl, $C_{1-6}$ alkoxy, $C_{1-6}$ acyloxy, $C_{1-6}$ acyl, $C_{1-3}$ alkyl-OC(O)—, $C_{1-4}$ alkyl-NHC(O)—, $C_{1-4}$ alkyl)$_2$NC(O), $C_{3-8}$ cycloalkyl, $C_{1-6}$ alkylamino-, $(C_{1-4}$ alkyl)$_2$amino-, $C_{3-6}$ cycloalkylamino-, $C_{1-6}$ acylamino-, aryl$C_{1-4}$ alkylamino-, heteroaryl$C_{1-4}$ alkylamino-, aryl, heteroaryl, a 3-6 membered heterocycle, and a 3-8 membered carbocyclic ring, wherein the alkyl, cycloalkyl, aryl, heterocycle, and heteroaryl groups are substituted with 0-2 $R^6$;

alternatively, $R^{5a}$ and $R^{5b}$ taken together form a ring selected from a 3-6 membered heterocyclic ring, a 5-6 membered lactone ring, and a 4-6 membered lactam ring, wherein the ring is substituted with 0-2 $R^6$ and the lactone ring and the lactam ring optionally contain an additional heteroatom selected from O, N, NR, and S;

$R^{5c}$ is selected from H, $C_{1-6}$ alkyl, $C_{3-6}$ cycloalkyl, $C_{1-3}$ alkylsulfonyl-, $C_{1-3}$ alkylaminosulfonyl-, di$C_{1-3}$ alkylaminosulfonyl-, $C_{1-6}$ acyl, $C_{1-6}$ alkyl-OC(O)—, aryl, and heteroaryl, wherein the alkyl, aryl, and heteroaryl groups are substituted with 0-2 $R^6$;

$R^6$ at each occurrence is independently selected from halo, —CN, OH, $C_{1-6}$ alkyl, $C_{2-6}$ alkenyl, $C_{3-8}$ cycloalkyl, $C_{1-6}$ alkoxy, $C_{1-6}$ acyl, $C_{1-6}$ acyloxy, $C_{1-6}$ alkyl-OC(O)—, $C_{1-4}$ alkyl-NHC(O)—, $(C_{1-4}$ alkyl)$_2$NC(O), $NH_2$, $C_{1-6}$ alkylamino-, $(C_{1-4}$ alkyl)$_2$amino-, $C_{3-6}$ cycloalkylamino-, $C_{1-6}$ acylamino-, $C(O)NH_2$, —$CONH(CH_2)_mCHQ(CH_2)_mCO_2R$, and —$CONH(CH_2)_mCHQ(CH_2)_mCONHR$;

alternatively, $R^{3a}$ and $R^{3b}$ taken together with $R^{3c}$ and $R^{3d}$ forms a bond, a methylene bridge, or an ethylene bridge;

alternatively, $R^{4a}$ and $R^{4b}$ taken together with $R^{3c}$ and $R^{3d}$ forms a bond, a methylene bridge, or an ethylene bridge; and, alternatively, either $R^{4c}$ and $R^{4d}$ taken together with $R^{4a}$ and $R^{4b}$ or with $R^{3a}$ and $R^{3b}$ forms a bond, a methylene bridge, or an ethylene bridge.

[2a] In another embodiment, the present invention provides novel compounds of formula IIa or a stereoisomer or pharmaceutically acceptable salt thereof:

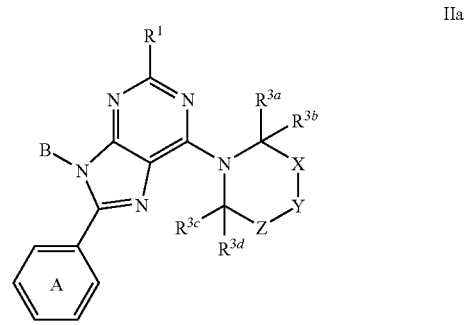

IIa wherein:
ring A is substituted with 0-3 substituents selected from the group consisting of halo, $C_{1-4}$ alkoxy, $C_{1-4}$ alkyl, $C_{1-4}$ haloalkyl, and cyano.

[2b] In another embodiment, the present invention provides novel compounds of formula IIa$_1$ or a stereoisomer or pharmaceutically acceptable salt thereof:

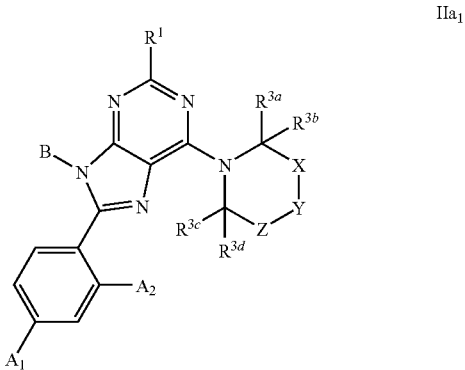

IIa$_1$ wherein:
$A_1$ and $A_2$ are independently selected from H, Cl, F, and $CF_3$; and,
B is phenyl substituted with 1-2 substituents selected from $CO_2R$, $RO_2C(CH_2)_mCHQ(CH_2)_mNHC(O)(CH_2)_m$—, $R^c_2NC(O)(CH_2)_mCHQ(CH_2)_mNHC(O)(CH_2)_m$—, $RO_2C(CH_2)_mCHQ(CH_2)_mNHC(O)(CH_2)_mCHQ(CH_2)_mNHC(O)(CH_2)_m$—, $R^c_2NC(O)(CH_2)_mCHQ(CH_2)_mNHC(O)(CH_2)_m$ $CHQ(CH_2)_mNHC(O)(CH_2)_m$—, $(CH_2)_nCO_2R$, $O(CH_2)_n$ $CO_2R$, $OCH_2CH=CHCO_2R$, $CH_2O(CH_2)_nCO_2R$, $CH_2OCH_2CH=CHCO_2R$, $O(CH_2)_nPO(OR)_2$, $CH_2O(CH_2)_n$ $PO(OR)_2$, $NR^a(CH_2)_mCO_2R$, $NR^a(CH_2)_nPO(OR)_2$, $NR^aCH_2CH=CHCO_2R$, $NR^aSO_2CH_3$, $NR^aCO(CH_2)_n$ $CO_2R$, $O(CH_2)_nC_6H_4CO_2R$, $O(CH_2)_nC_6H_4(CH_2)_nCO_2R$, $CH_2O(CH_2)_nC_6H_4CO_2R$, $O(CH_2)_nC_6H_4CONR^c_2$, $O(CH_2)_n$ $C_6H_4(CH_2)_nCONR^c_2$, $CH_2O(CH_2)_nC_6H_4CONR^c_2$, $O(CH_2)_n$ $C_6H_4$-tetrazole, $CH_2O(CH_2)_nC_6H_4$-tetrazole, $O(CH_2)_n C_6H_4$ $(CH_2)_n$-tetrazole, $NR^a(CH_2)_nC_6H_4CO_2R$, $CH_2NR^a(CH_2)_n$ $C_6H_4CO_2R$, $NR^a(CH_2)_nC_6H_4CONR^c_2$, $CH_2NR^a(CH_2)_n$ $C_6H_4CONR^c_2$, $NR^a(CH_2)_nC_6H_4$-tetrazole, $CH_2NR^a(CH_2)_n$ $C_6H_4$-tetrazole, —CN, $(CH_2)_mC(=NH)NH_2$, $(CH_2)_m$ NHC $(=NH)NH_2$, $(CH_2)_mNHC(=CHNO_2)NH_2$, $(CH_2)_m$ NHC $(=NCN)NH_2$, $CONR^c_2$, $(CH_2)_nCONR^c_2$, $O(CH_2)_n$ $CONR^c_2$, $CH_2O(CH_2)_nCONR^c_2$, $NR^a(CH_2)_mCONHR^a$, $OCH_2CH=CHCONR^c_2$, $CH_2OCH_2CH=CHCONR^c_2$, $NR^aCH_2CH=CHCONR^c_2$, tetrazole, $O(CH_2CH_2O)_pR$, $NR^a(CH_2CH_2O)_pR$, $SONH_2$, and $SO_2NR^aCH_3$.

[3] In another embodiment, the present invention provides novel compounds of formula I or a stereoisomer or pharmaceutically acceptable salt thereof, wherein:

A and B are selected from an optionally substituted aryl or an optionally substituted heteroaryl, the substituents being from one to three independently selected from halo, $C_{1-4}$ alkoxy, $C_{1-4}$ alkyl, $C_{1-4}$ haloalkyl, and cyano;

X is selected from a bond, $-CH_2CH_2-$ and $-C(R^{4a})(R^{4b})-$;

Y is selected from O, S, $NR^{5c}$, C(O), C=NOH, and $-C(R^{5a})(R^{5b})-$;

Z is selected from a bond, $-CH_2CH_2-$ and $-C(R^{4c})(R^{4d})-$;

$R^1$ is selected from $(CH_2)_nCO_2R$, $RO_2C(CH_2)_mCHQ(CH_2)_mNHC(O)(CH_2)_n$, $R^c_2NC(O)(CH_2)_mCHQ(CH_2)_mNHC(O)(CH_2)_n-$, $OCH_2CH=CHCO_2R$, $CH_2O(CH_2)_nCO_2R$, $CH_2OCH_2CH=CHCO_2R$, $O(CH_2)_nPO(OR)_2$, $CH_2O(CH_2)_nPO(OR)_2$, $NR^a(CH_2)_mCO_2R$, $NR^a(CH_2)_nPO(OR)_2$, $NR^aCH_2CH=CHCO_2R$, $NR^aSO_2CH_3$, $NR^aCO(CH_2)_nCO_2R$, $(CH_2)_mNHC(=NH)NH_2$, $(CH_2)_mNHC(=CNO_2)NH_2$, $(CH_2)_mNHC(=NCN)NH_2$, $(CH_2)_n CONR^c_2$, $O(CH_2)_n CONR^c_2$, $CH_2O(CH_2)_nCONR^c_2$, $(CH_2)_m NR^a(CH_2)_n CONHR^a$, $(CH_2)_mNR^aC(O)(CH_2)_nCO_2R$, $(CH_2)_mNR^aC(O)(CH_2)_n CONR^c_2$, $(CH_2)_mNR^a(CH_2)_m CHQCO_2R$, $(CH_2)_mNR^a(CH_2)_mCHQCONR^c_2$, $(CH_2)_nCH(NHR^a)CO_2R$, $(CH_2)_nCH(NHR^a)CONHR^a$, $CH_2OCH_2CH=CHCONR^c_2$, $NR^aCH_2CH=CHCONR^c_2$, and $(CH_2)_m$tetrazole, $R^{3a}$, $R^{3b}$, $R^{3c}$, $R^{3d}$, $R^{4a}$, $R^{4b}$, $R^{4c}$, $R^{4d}$, $R^{5a}$, and $R^{5b}$ are each independently selected from H, cyano, OH, $NH_2$, $H_2NC(O)-$, $C_{1-6}$ alkyl, $C_{1-6}$ alkoxy, $C_{1-6}$ acyloxy, $C_{1-6}$ acyl, $C_{1-3}$ alkyl-OC(O)—, $C_{1-4}$ alkyl-NHC(O)—, $C_{1-4}$ alkyl)$_2$NC(O), $C_{3-8}$ cycloalkyl, $C_{1-6}$ alkylamino-, $(C_{1-4}$ alkyl)$_2$amino-, $C_{3-6}$ cycloalkylamino-, $C_{1-6}$ acylamino-, aryl$C_{1-4}$ alkylamino-, heteroaryl$C_{1-4}$ alkylamino-, aryl, heteroaryl, a 3-6 membered heterocycle, and a 3-8 membered carbocyclic ring, wherein the alkyl, cycloalkyl, aryl, heterocycle, and heteroaryl groups are substituted with 0-2 $R^6$;

alternatively, $R^{5a}$ and $R^{5b}$ taken together form a ring selected from a 3-6 membered heterocyclic ring, a 5-6 membered lactone ring, and a 4-6 membered lactam ring, wherein the ring is substituted with 0-2 $R^6$ and the lactone ring and the lactam ring optionally contain an additional heteroatom selected from O, N, NR, and S;

$R^{5c}$ is selected from H, $C_{1-6}$ alkyl, $C_{3-6}$ cycloalkyl, $C_{1-3}$ alkylsulfonyl-, $C_{1-3}$ alkylaminosulfonyl-, di$C_{1-3}$ alkylaminosulfonyl-, $C_{1-6}$ acyl, $C_{1-6}$ alkyl-OC(O)—, aryl, and heteroaryl, wherein the alkyl, aryl, and heteroaryl groups are substituted with 0-2 $R^6$;

$R^6$ at each occurrence is independently selected from halo, —CN, OH, $C_{1-6}$ alkyl, $C_{2-6}$ alkenyl, $C_{3-8}$ cycloalkyl, $C_{1-6}$ alkoxy, $C_{1-6}$ acyl, $C_{1-6}$ alkyl-OC(O)—, $C_{1-4}$ alkyl-NHC(O)—, $(C_{1-4}$ alkyl)$_2$NC(O), $NH_2$, $C_{1-6}$ alkylamino-, $(C_{1-4}$ alkyl)$_2$amino-, $C_{3-6}$ cycloalkylamino-, $C_{1-6}$ acylamino-, C(O)$NH_2$, —CONH$(CH_2)_mCHQ(CH_2)_mCO_2R$, and —CONH$(CH_2)_mCHQ(CH_2)_mCONHR$;

alternatively, $R^{3a}$ and $R^{3b}$ taken together with $R^{3c}$ and $R^{3d}$ forms a bond, a methylene bridge, or an ethylene bridge;

alternatively, $R^{4a}$ and $R^{4b}$ taken together with $R^{3c}$ and $R^{3d}$ forms a bond, a methylene bridge, or an ethylene bridge; and, alternatively, either $R^{4c}$ and $R^{4d}$ taken together with $R^{4a}$ and $R^{4b}$ or with $R^{3a}$ and $R^{3b}$ forms a bond, a methylene bridge, or an ethylene bridge.

[3a] In another embodiment, the present invention provides novel compounds of formula IIa or a stereoisomer or pharmaceutically acceptable salt thereof:

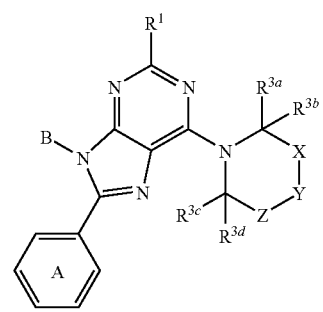

IIa wherein:

ring A is substituted with 0-3 substituents selected from the group consisting of halo, $C_{1-4}$ alkoxy, $C_{1-4}$ alkyl, $C_{1-4}$ haloalkyl, and cyano.

[3b] In another embodiment, the present invention provides novel compounds of formula IIb or a stereoisomer or pharmaceutically acceptable salt thereof:

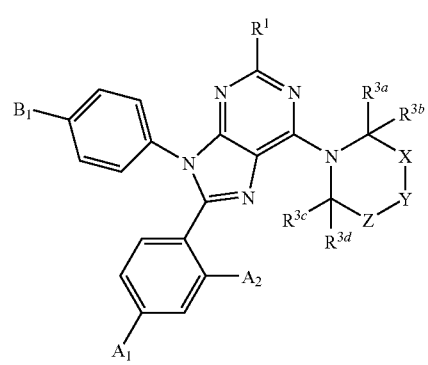

IIb wherein:

$A_1$ and $A_2$ are independently selected from H, Cl, F, and $CF_3$; and, $B_1$ is selected from Cl, F, and $CF_3$.

[4] In another embodiment, the present invention provides novel compounds of formula I or a stereoisomer or pharmaceutically acceptable salt thereof, wherein:

A and B are selected from an optionally substituted aryl or an optionally substituted heteroaryl, the substituents being from one to three independently selected from halo, $C_{1-4}$ alkoxy, $C_{1-4}$ alkyl, $C_{1-4}$ haloalkyl, and cyano;

X is selected from a bond, $-CH_2CH_2-$ and $-C(R^{4a})(R^{4b})-$;

Y is selected from O, S, $NR^{5c}$, C(O), C=NOH, and $-C(R^{5a})(R^{5b})-$;

Z is selected from a bond, $-CH_2CH_2-$ and $-C(R^{4c})(R^{4d})-$;

$R^1$ is selected from H, $C_{1-4}$ alkyl, $C_{1-4}$ haloalkyl, and $C_{1-4}$ alkoxy;

one or two of $R^{3a}$, $R^{3b}$, $R^{3c}$, $R^{3d}$, $R^{4a}$, $R^{4b}$, $R^{4c}$, $R^{4d}$, $R^{5a}$, and $R^{5b}$ are selected from $RO_2C(CH_2)_mCHQ(CH_2)_m-$, $R_2N(O)C(CH_2)_mCHQ(CH_2)_m-$, $R_2NS(O_2)C(CH_2)_mCHQ(CH_2)_m-$, $RO_2C(CH_2)_mCHQ(CH_2)_mNHC(O)-$, $R^c_2NC(O)(CH_2)_mCHQ(CH_2)_mNHC(O)-$, $RO_2C(CH_2)_mCHQ$ $(CH_2)_m NHC(O)(CH_2)_m CHQ(CH_2)_m NHC(O)$—, $R^c{}_2NC(O)$ $(CH_2)_m$ $CHQ(CH_2)_m NHC(O)(CH_2)_m CHQ(CH_2)_m NHC(O)$—, $RO_2C(CH_2)_m CHQ(CH_2)_m NHC(O)(CH_2)_m CHQ(CH_2)_m NHC(O)(CH_2)_m CHQ(CH_2)_m NHC(O)$—, $R^c{}_2NC(O)(CH_2)_m CHQ(CH_2)_m NHC(O)(CH_2)_m CHQ(CH_2)_m NHC(O)(CH_2)_m CHQ(CH_2)_m NHC(O)$—, $ROS(O_2)(CH_2)_m CHQ(CH_2)_m NHC(O)$—, and $R^c{}_2NS(O_2)(CH_2)_m CHQ(CH_2)_m NHC(O)$—;

the remainder of $R^{3b}, R^{3c}, R^{3d}, R^{4a}, R^{4b}, R^{4c}, R^{4d}, R^{5a}$, and $R^{5b}$ are each independently selected from H, cyano, OH, $NH_2$, $C_{1-4}$ alkyl-NH—, $(C_{1-4}$ alkyl$)_2$N—, $H_2NC(O)$—, $C_{1-6}$ alkyl, $C_{1-6}$ alkoxy, $C_{1-6}$ acyloxy, $C_{1-6}$ acyl, $C_{1-3}$ alkyl-OC(O)—, $C_{1-4}$ alkyl-NHC(O)—, $(C_{1-4}$ alkyl$)_2$NC(O), $C_{3-8}$ cycloalkyl, $C_{1-6}$ alkylamino-, $(C_{1-4}$ alkyl$)_2$amino-, $C_{3-6}$ cycloalkylamino-, $C_{1-6}$ acylamino-, aryl$C_{1-4}$ alkylamino-, heteroaryl$C_{1-4}$ alkylamino-, aryl, heteroaryl, a 3-6 membered heterocycle, and a 3-8 membered carbocyclic ring, wherein the alkyl, cycloalkyl, aryl, heterocycle, and heteroaryl groups are substituted with 0-2 $R^6$;

alternatively, $R^{5a}$ and $R^{5b}$ taken together form a ring selected from a 3-6 membered heterocyclic ring, a 5-6 membered lactone ring, and a 4-6 membered lactam ring, wherein the ring is substituted with 0-2 $R^6$ and the lactone ring and the lactam ring optionally contain an additional heteroatom selected from O, N, NR, and S;

$R^{5c}$ is selected from H, $C_{1-6}$ alkyl, $C_{3-6}$ cycloalkyl, $C_{1-3}$ alkylsulfonyl-, $C_{1-3}$ alkylaminosulfonyl-, di$C_{1-3}$ alkylaminosulfonyl-, $C_{1-6}$ acyl, $C_{1-6}$ alkyl-OC(O)—, aryl, and heteroaryl, wherein the alkyl, aryl, and heteroaryl groups are substituted with 0-2 $R^6$;

$R^6$ at each occurrence is independently selected from halo, —CN, OH, $C_{1-6}$ alkyl, $C_{2-6}$ alkenyl, $C_{3-8}$ cycloalkyl, $C_{1-6}$ alkoxy, $C_{1-6}$ acyl, $C_{1-6}$ acyloxy, $C_{1-6}$ alkyl-OC(O)—, $C_{1-4}$ alkyl-NHC(O)—, $(C_{1-4}$ alkyl$)_2$NC(O), $NH_2$, $C_{1-6}$ alkylamino-, $(C_{1-4}$ alkyl$)_2$amino-, $C_{3-6}$ cycloalkylamino-, $C_{1-6}$ acylamino-, $C(O)NH_2$, —$CONH(CH_2)_m CHQ(CH_2)_m CO_2R$, and —$CONH(CH_2)_m CHQ(CH_2)_m CONHR$;

alternatively, $R^{3a}$ and $R^{3b}$ taken together with $R^{3c}$ and $R^{3d}$ forms a bond, a methylene bridge, or an ethylene bridge;

alternatively, $R^{4a}$ and $R^{4b}$ taken together with $R^{3c}$ and $R^{3d}$ forms a bond, a methylene bridge, or an ethylene bridge; and, alternatively, either $R^{4c}$ and $R^{4d}$ taken together with $R^{4a}$ and $R^{4b}$ or with $R^{3a}$ and $R^{3b}$ forms a bond, a methylene bridge, or an ethylene bridge.

[4a] In another embodiment, the present invention provides novel compounds of formula IIa or a stereoisomer or pharmaceutically acceptable salt thereof:

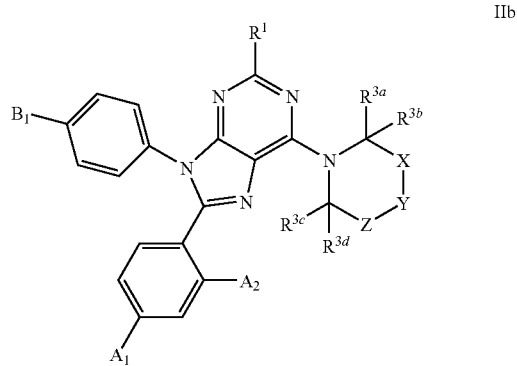

wherein:
ring A is substituted with 0-3 substituents selected from the group consisting of halo, $C_{1-4}$ alkoxy, $C_{1-4}$ alkyl, $C_{1-4}$ haloalkyl, and cyano.

[4b] In another embodiment, the present invention provides novel compounds of formula IIb or a stereoisomer or pharmaceutically acceptable salt thereof:

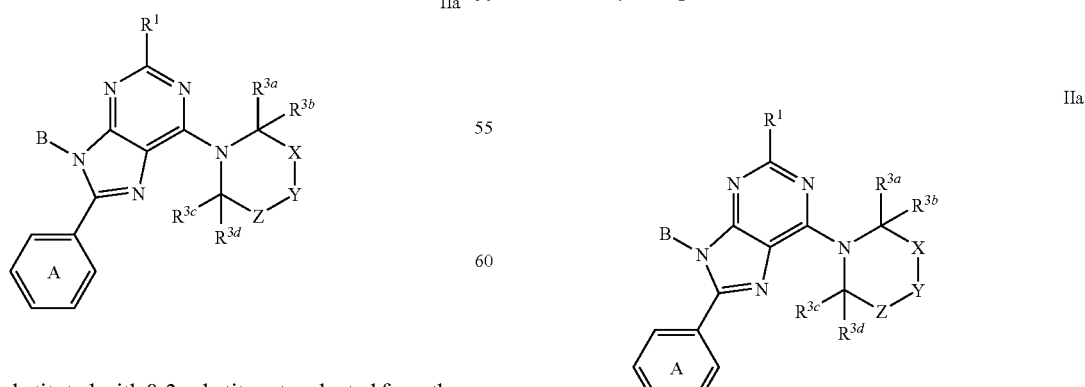

wherein:
$A_1$ and $A_2$ are independently selected from H, Cl, F, and $CF_3$; and,
$B_1$ is selected from Cl, F, and $CF_3$.

[5] In another embodiment, the present invention provides novel compounds of formula I or a stereoisomer or pharmaceutically acceptable salt thereof, wherein:

$R^{3a}$ is selected from $RO_2C(CH_2)_m CHQ(CH_2)_m$—, $R_2N(O)C(CH_2)_m CHQ(CH_2)_m$—, $R_2NS(O_2)C(CH_2)_m CHQ(CH_2)_m$—, $RO_2C(CH_2)_m CHQ(CH_2)_m NHC(O)$—, $R^c{}_2NC(O)(CH_2)_m CHQ(CH_2)_m NHC(O)$—, $RO_2C(CH_2)_m CHQ(CH_2)_m NHC(O)(CH_2)_m CHQ(CH_2)_m NHC(O)$—, $R^c{}_2NC(O)(CH_2)_m CHQ(CH_2)_m NHC(O)(CH_2)_m CHQ(CH_2)_m NHC(O)$—, $RO_2C(CH_2)_m CHQ(CH_2)_m NHC(O)(CH_2)_m CHQ(CH_2)_m NHC(O)(CH_2)_m CHQ(CH_2)_m NHC(O)$—, $R^c{}_2NC(O)(CH_2)_m CHQ(CH_2)_m NHC(O)(CH_2)_m CHQ(CH_2)_m NHC(O)(CH_2)_m CHQ(CH_2)_m NHC(O)$—, $ROS(O_2)(CH_2)_m CHQ(CH_2)_m NHC(O)$—, and $R^c{}_2NS(O_2)(CH_2)_m CHQ(CH_2)_m NHC(O)$—.

[5a] In another embodiment, the present invention provides novel compounds of formula IIa or a stereoisomer or pharmaceutically acceptable salt thereof:

wherein:

ring A is substituted with 0-3 substituents selected from the group consisting of halo, $C_{1-4}$ alkoxy, $C_{1-4}$ alkyl, $C_{1-4}$ haloalkyl, and cyano.

[5b] In another embodiment, the present invention provides novel compounds of formula IIb or a stereoisomer or pharmaceutically acceptable salt thereof:

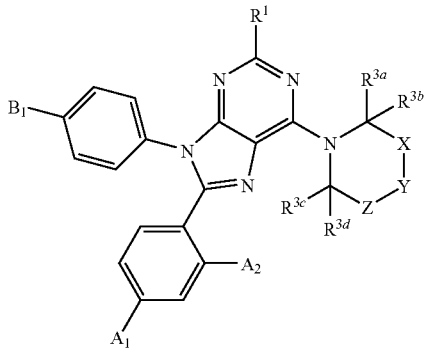

IIb wherein:

$A_1$ and $A_2$ are independently selected from H, Cl, F, and $CF_3$; and, $B_1$ is selected from Cl, F, and $CF_3$.

[6] In another embodiment, the present invention provides novel compounds of formula I or a stereoisomer or pharmaceutically acceptable salt thereof, wherein:

$R^{3c}$ is selected from $RO_2C(CH_2)_mCHQ(CH_2)_m$—, $R_2N(O)C(CH_2)_mCHQ(CH_2)_m$—, $R_2NS(O_2)C(CH_2)_mCHQ(CH_2)_m$—, $RO_2C(CH_2)_mCHQ(CH_2)_mNHC(O)$—, $R^c_2NC(O)(CH_2)_mCHQ(CH_2)_mNHC(O)$—, $RO_2C(CH_2)_mCHQ(CH_2)_m NHC(O)(CH_2)_mCHQ(CH_2)_mNHC(O)$—, $R^c_2NC(O)(CH_2)_m CHQ(CH_2)_mNHC(O)(CH_2)_mCHQ(CH_2)_mNHC(O)$—, $RO_2C(CH_2)_mCHQ(CH_2)_mNHC(O)(CH_2)_mCHQ(CH_2)_m NHC(O)(CH_2)_mCHQ(CH_2)_mNHC(O)$—, $R^c_2NC(O)(CH_2)_m CHQ(CH_2)_mNHC(O)(CH_2)_mCHQ(CH_2)_mNHC(O)(CH_2)_m CHQ(CH_2)_mNHC(O)$—, $ROS(O_2)(CH_2)_mCHQ(CH_2)_m NHC(O)$—, and, $R^c_2NS(O_2)(CH_2)_mCHQ(CH_2)_m NHC(O)$—.

[6a] In another embodiment, the present invention provides novel compounds of formula IIa or a stereoisomer or pharmaceutically acceptable salt thereof:

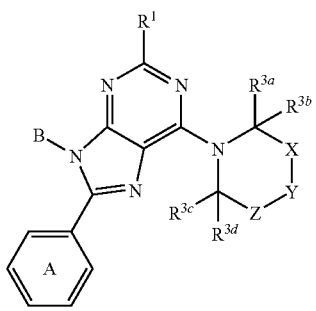

IIa wherein:

ring A is substituted with 0-3 substituents selected from the group consisting of halo, $C_{1-4}$ alkoxy, $C_{1-4}$ alkyl, $C_{1-4}$ haloalkyl, and cyano.

[6b] In another embodiment, the present invention provides novel compounds of formula IIb or a stereoisomer or pharmaceutically acceptable salt thereof:

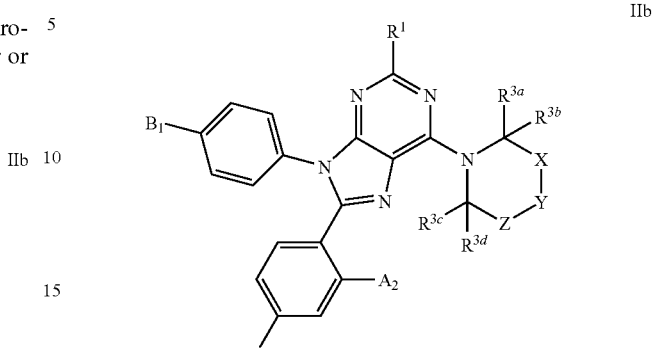

IIb wherein:

$A_1$ and $A_2$ are independently selected from H, Cl, F, and $CF_3$; and, $B_1$ is selected from Cl, F, and $CF_3$.

[7] In another embodiment, the present invention provides novel compounds of formula IIIa or a stereoisomer or pharmaceutically acceptable salt thereof:

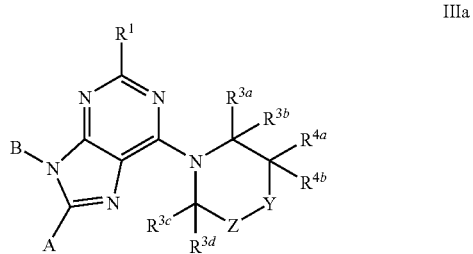

IIIa wherein:

$R^{4a}$ is selected from $RO_2C(CH_2)_mCHQ(CH_2)_m$—, $R_2N(O)C(CH_2)_mCHQ(CH_2)_m$—, $R_2NS(O_2)C(CH_2)_mCHQ(CH_2)_m$—, $RO_2C(CH_2)_mCHQ(CH_2)_mNHC(O)$—, $R^c_2NC(O)(CH_2)_mCHQ(CH_2)_mNHC(O)$—, $RO_2C(CH_2)_mCHQ(CH_2)_m NHC(O)(CH_2)_mCHQ(CH_2)_mNHC(O)$—, $R^c_2NC(O)(CH_2)_m CHQ(CH_2)_mNHC(O)(CH_2)_mCHQ(CH_2)_mNHC(O)$—, $RO_2C(CH_2)_mCHQ(CH_2)_mNHC(O)(CH_2)_mCHQ(CH_2)_m NHC(O)(CH_2)_mCHQ(CH_2)_mNHC(O)$—, $R^c_2NC(O)(CH_2)_m CHQ(CH_2)_mNHC(O)(CH_2)_mCHQ(CH_2)_mNHC(O)(CH_2)_m CHQ(CH_2)_mNHC(O)$—, $ROS(O_2)(CH_2)_mCHQ(CH_2)_m NHC(O)$—, and $R^c_2NS(O_2)(CH_2)_mCHQ(CH_2)_m NHC(O)$—.

[7a] In another embodiment, the present invention provides novel compounds of formula IIIb or a stereoisomer or pharmaceutically acceptable salt thereof:

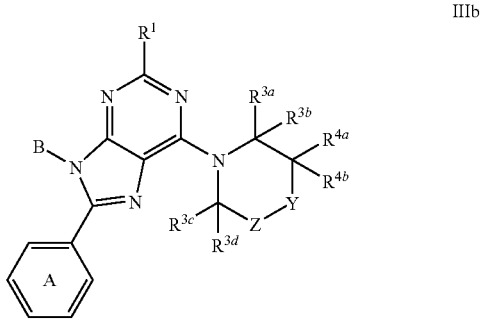

IIIb wherein:

ring A is substituted with 0-3 substituents selected from the group consisting of halo, $C_{1-4}$ alkoxy, $C_{1-4}$ alkyl, $C_{1-4}$ haloalkyl, and cyano.

[7b] In another embodiment, the present invention provides novel compounds of formula IIIc or a stereoisomer or pharmaceutically acceptable salt thereof:

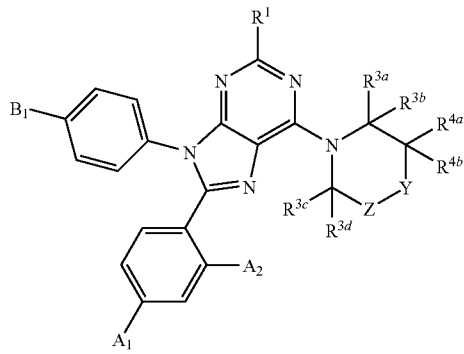

IIIc wherein:

$A_1$ and $A_2$ are independently selected from H, Cl, F, and $CF_3$; and, $B_1$ is selected from Cl, F, and $CF_3$.

[8] In another embodiment, the present invention provides novel compounds of formula IVa or a stereoisomer or pharmaceutically acceptable salt thereof:

IVa wherein:

$R^{5a}$ is selected from $RO_2C(CH_2)_mCHQ(CH_2)_m-$, $R_2N(O)C(CH_2)_mCHQ(CH_2)_m-$, $R_2NS(O_2)C(CH_2)_mCHQ(CH_2)_m-$, $RO_2C(CH_2)_mCHQ(CH_2)_mNHC(O)-$, $R^c{}_2NC(O)(CH_2)_mCHQ(CH_2)_mNHC(O)-$, $RO_2C(CH_2)_mCHQ(CH_2)_m NHC(O)(CH_2)_mCHQ(CH_2)_mNHC(O)-$, $R^c{}_2NC(O)(CH_2)_m CHQ(CH_2)_mNHC(O)(CH_2)_mCHQ(CH_2)_mNHC(O)-$, $RO_2C(CH_2)_mCHQ(CH_2)_mNHC(O)(CH_2)_mCHQ(CH_2)_m NHC(O)(CH_2)_mCHQ(CH_2)_mNHC(O)-$, $R^c{}_2NC(O)(CH_2)_m CHQ(CH_2)_mNHC(O)(CH_2)_mCHQ(CH_2)_mNHC(O)(CH_2)_m CHQ(CH_2)_mNHC(O)-$, $ROS(O_2)(CH_2)_mCHQ(CH_2)_m NHC(O)-$, and $R^c{}_2NS(O_2)(CH_2)_mCHQ(CH_2)_m NHC(O)-$.

[8a] In another embodiment, the present invention provides novel compounds of formula IVb or a stereoisomer or pharmaceutically acceptable salt thereof:

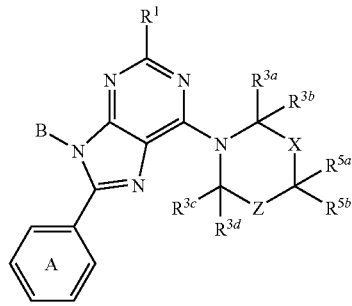

IVb wherein:

ring A is substituted with 0-3 substituents selected from the group consisting of halo, $C_{1-4}$ alkoxy, $C_{1-4}$ alkyl, $C_{1-4}$ haloalkyl, and cyano.

[8b] In another embodiment, the present invention provides novel compounds of formula IVc or a stereoisomer or pharmaceutically acceptable salt thereof:

IVc wherein:

$A_1$ and $A_2$ are independently selected from H, Cl, F, and $CF_3$; and, $B_1$ is selected from Cl, F, and $CF_3$.

[9] In another embodiment, the present invention provides novel compounds of formula Va or a stereoisomer or pharmaceutically acceptable salt thereof:

Va wherein:

$R^{4c}$ is selected from $RO_2C(CH_2)_mCHQ(CH_2)_m-$, $R_2N(O)C(CH_2)_mCHQ(CH_2)_m-$, $R_2NS(O_2)C(CH_2)_mCHQ$ $(CH_2)_m$—, $RO_2C(CH_2)_mCHQ(CH_2)_mNHC(O)$—, $R^c{}_2NC(O)(CH_2)_mCHQ(CH_2)_mNHC(O)$—, $RO_2C(CH_2)_mCHQ(CH_2)_m NHC(O)(CH_2)_mCHQ(CH_2)_mNHC(O)$—, $R^c{}_2NC(O)(CH_2)_m CHQ(CH_2)_mNHC(O)(CH_2)_mCHQ(CH_2)_mNHC(O)$—, $RO_2C(CH_2)_mCHQ(CH_2)_mNHC(O)(CH_2)_mCHQ(CH_2)_m NHC(O)(CH_2)_mCHQ(CH_2)_mNHC(O)$—, $R^c{}_2NC(O)(CH_2)_m CHQ(CH_2)_mNHC(O)(CH_2)_mCHQ(CH_2)_mNHC(O)(CH_2)_m CHQ(CH_2)_mNHC(O)$—, $ROS(O_2)(CH_2)_mCHQ(CH_2)_m NHC(O)$—, and $R^c{}_2NS(O_2)(CH_2)_mCHQ(CH_2)_m NHC(O)$—.

[9a] In another embodiment, the present invention provides novel compounds of formula Vb or a stereoisomer or pharmaceutically acceptable salt thereof:

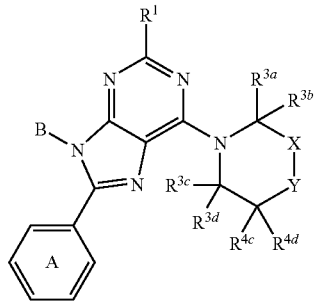

Vb wherein:

ring A is substituted with 0-3 substituents selected from the group consisting of halo, $C_{1-4}$ alkoxy, $C_{1-4}$ alkyl, $C_{1-4}$ haloalkyl, and cyano.

[9b] In another embodiment, the present invention provides novel compounds of formula Vc or a stereoisomer or pharmaceutically acceptable salt thereof:

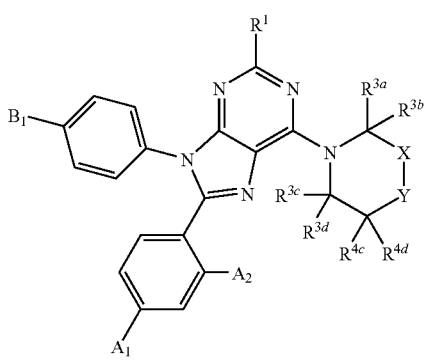

Vc wherein:

$A_1$ and $A_2$ are independently selected from H, Cl, F, and $CF_3$; and, $B_1$ is selected from Cl, F, and $CF_3$.

[10] In another embodiment, the present invention provides novel compounds of formula VIa or a stereoisomer or pharmaceutically acceptable salt thereof:

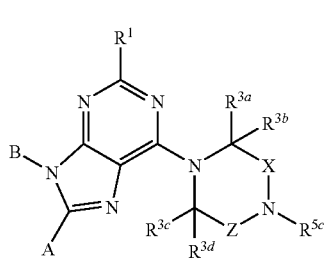

VIa wherein:

A and B are selected from an optionally substituted aryl or an optionally substituted heteroaryl, the substituents being from one to three independently selected from halo, $C_{1-4}$ alkoxy, $C_{1-4}$ alkyl, $C_{1-4}$ haloalkyl, and cyano;

X is selected from a bond, —$CH_2CH_2$— and —$C(R^{4a})(R^{4b})$—;

Z is selected from a bond, —$CH_2CH_2$— and —$C(R^{4c})(R^{4d})$—;

$R^1$ is selected from H, $C_{1-4}$ alkyl, $C_{1-4}$ haloalkyl, and $C_{1-4}$ alkoxy;

$R^{3a}$, $R^{3b}$, $R^{3c}$, $R^{3d}$, $R^{4a}$, $R^{4b}$, $R^{4c}$, $R^{4d}$, $R^{5a}$, and $R^{5b}$ are each independently selected from H, cyano, OH, $NH_2$, $H_2NC(O)$—, $C_{1-6}$ alkyl, $C_{1-6}$ alkoxy, $C_{1-6}$ acyloxy, $C_{1-6}$ acyl, $C_{1-3}$ alkyl-OC(O)—, $C_{1-4}$ alkyl-NHC(O)—, $C_{1-4}$ alkyl)$_2$NC(O), $C_{1-6}$ alkylamino-, $(C_{1-4}$ alkyl)$_2$amino-, $C_{3-6}$ cycloalkylamino-, $C_{1-6}$ acylamino-, aryl$C_{1-4}$ alkylamino-, heteroaryl$C_{1-4}$ alkylamino-, aryl, heteroaryl, a 3-6 membered heterocycle, and a 3-8 membered carbocyclic ring, wherein the alkyl, cycloalkyl, aryl, heterocycle, and heteroaryl groups are substituted with 0-2 $R^6$;

alternatively, $R^{5a}$ and $R^{5b}$ taken together form a ring selected from a 3-6 membered heterocyclic ring, a 5-6 membered lactone ring, and a 4-6 membered lactam ring, wherein the ring is substituted with 0-2 $R^6$ and the lactone ring and the lactam ring optionally contain an additional heteroatom selected from O, N, NR, and S;

$R^{5c}$ is selected from —$(CH_2)_mCO_2R$, —$C(O)(CH_2)_nCO_2R$, —$(CH_2)_mCONR^c{}_2$, —$C(O)(CH_2)_nCONR^c{}_2$, —$(CH_2)_mC(O)NH(CH_2)_nCO_2R$, —$(CH_2)_mC(O)NH(CH_2)_n CONR^c{}_2$, —$C(O)(CH_2)_nCONH(CH_2)_mCHQ(CH_2)_mCO_2R$, and —$C(O)(CH_2)_nCONH(CH_2)_mCHQ(CH_2)_mCONR^c{}_2$;

$R^6$ at each occurrence is independently selected from halo, —CN, OH, $C_{1-6}$ alkyl, $C_{2-6}$ alkenyl, $C_{3-8}$ cycloalkyl, $C_{1-6}$ alkoxy, $C_{1-6}$ acyl, $C_{1-6}$ acyloxy, $C_{1-4}$ alkyl-NHC(O)—, $(C_{1-4}$ alkyl)$_2$NC(O), $NH_2$, $C_{1-6}$ alkylamino-, $(C_{1-4}$ alkyl)$_2$amino-, $C_{3-6}$ cycloalkylamino-, $C_{1-6}$ acylamino-, $C(O)NH_2$, —$CONH(CH_2)_mCHQ(CH_2)_mCO_2R$, and —$CONH(CH_2)_m CHQ(CH_2)_mCONHR$;

alternatively, $R^{3a}$ and $R^{3b}$ taken together with $R^{3c}$ and $R^{3d}$ forms a bond, a methylene bridge, or an ethylene bridge;

alternatively, $R^{4a}$ and $R^{4b}$ taken together with $R^{3c}$ and $R^{3d}$ forms a bond, a methylene bridge, or an ethylene bridge; and, alternatively, either $R^{4c}$ and $R^{4d}$ taken together with $R^{4a}$ and $R^{4b}$ or with $R^{3a}$ and $R^{3b}$ forms a bond, a methylene bridge, or an ethylene bridge.

[10a] In another embodiment, the present invention provides novel compounds of formula VIb or a stereoisomer or pharmaceutically acceptable salt thereof:

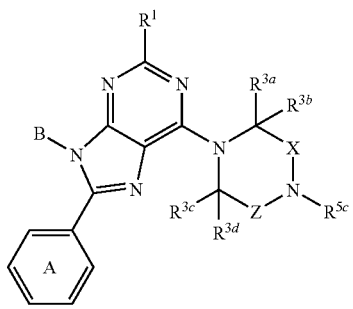

VIb wherein:

ring A is substituted with 0-3 substituents selected from the group consisting of halo, $C_{1-4}$ alkoxy, $C_{1-4}$ alkyl, $C_{1-4}$ haloalkyl, and cyano.

[10b] In another embodiment, the present invention provides novel compounds of formula VIc or a stereoisomer or pharmaceutically acceptable salt thereof:

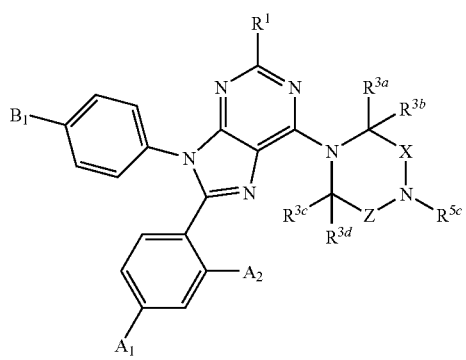

VIc wherein:

$A_1$ and $A_2$ are independently selected from H, Cl, F, and $CF_3$; and, $B_1$ is selected from Cl, F, and $CF_3$.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel method of modulating the activity of CB1 receptors (e.g., periperhal CB1 receptors) in a patient, comprising: administering to a patient in need thereof a therapeutically effective amount of a compound of the present invention or a pharmaceutically acceptable salt form thereof.

In another embodiment, the present invention provides a novel method of treating a disease characterized by an inappropriate activation of peripheral CB1 receptors, comprising: administering to a patient in need thereof a therapeutically effective amount of a compound of the present invention or a pharmaceutically acceptable salt form thereof.

In another embodiment, the present invention provides a novel method for treating a disease mediated by the $CB_1$ receptor in a patient, comprising: administering to a patient in need thereof a therapeutically effective amount of a compound of the present invention or a pharmaceutically acceptable salt form thereof. In an example, the disease is mediated by peripheral $CB_1$ receptors. In another example, the $CB_1$ receptors that are blocked are peripheral $CB_1$ receptors.

In another embodiment, the present invention provides a novel method for treating a disease, comprising: administering to a patient in need thereof a therapeutically effective amount of a compound of the present invention or a pharmaceutically acceptable salt form thereof, wherein the disease is selected from obesity, diabetes, dyslipidemias, cardiovascular disorders, inflammatory disorders, hepatic disorders, and a combination thereof.

In another embodiment, the diabetes disorder is selected from Type 1 diabetes, Type 2 diabetes, inadequate glucose tolerance, and insulin resistance.

In another embodiment, the dyslipidemia disorder is selected from undesirable blood lipid levels, including low levels of high-density lipoprotein, high levels of low-density lipoprotein, high levels of triglycerides, and a combination thereof.

In another embodiment, the cardiovascular disorder is selected from atherosclerosis, hypertension, stroke and heart attack.

In another embodiment, the inflammatory disorder is selected from inflammatory bowel disease, Alzheimer's disease, atherosclerosis, osteoperosis, multiple sclerosis, traumatic brain injury, arthritis, and neuropathic pain.

In another embodiment, the hepatic disorder is selected from liver inflammation, liver fibrosis, NASH, fatty liver, enlarged liver, alcoholic liver disease, jaundice, cirrhosis, and hepatitis.

In another embodiment, the present invention provides a novel method for treating a co-morbidity of obesity, comprising: administering to a patient in need thereof a therapeutically effective amount of a compound of the present invention or a pharmaceutically acceptable salt form thereof.

In another embodiment, the co-morbidity is selected from diabetes, dyslipidemias, Metabolic Syndrome, dementia, cardiovascular disease, and hepatic disease.

In another embodiment, the co-morbidity is selected from hypertension; gallbladder disease; gastrointestinal disorders; menstrual irregularities; degenerative arthritis; venous statis ulcers; pulmonary hypoventilation syndrome; sleep apnea; snoring; coronary artery disease; arterial sclerotic disease; pseudotumor cerebri; accident proneness; increased risks with surgeries; osteoarthritis; high cholesterol; and, increased incidence of malignancies of the ovaries, cervix, uterus, breasts, prostrate, and gallbladder.

In another embodiment, the present invention also provides a method of preventing or reversing the deposition of adipose tissue in a mammal by the administration of a compound of the present invention. By preventing or reversing the deposition of adipose tissue, compound of the present invention are expected to reduce the incidence or severity of obesity, thereby reducing the incidence or severity of associated co-morbidities.

In another embodiment, the present invention provides a compound of the present invention for use in therapy.

In another embodiment, the present invention provides the use of the present invention for the manufacture of a medicament for the treatment of an indication recited herein (e.g., obesity, diabetes, dyslipidemias, cardiovascular disorders, inflammatory disorders, hepatic disorders, and a combination thereof).

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

DEFINITIONS

The examples provided in the definitions present in this application are non-inclusive unless otherwise stated. They include but are not limited to the recited examples.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

Examples of the molecular weight of the compounds of the present invention include (a) less than about 500, 550, 600, 650, 700, 750, 800, 850, 900, 950, or 1000 grams per mole; (b) less than about 950 grams per mole; (c) less than about 850 grams per mole; and, (d) less than about 750 grams per mole.

"Alkyl" and "alkylene" includes both branched and straight-chain saturated aliphatic hydrocarbon groups having the specified number of carbon atoms. For example, $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

"Alkenyl" includes the specified number of hydrocarbon atoms in either straight or branched configuration with one or more unsaturated carbon-carbon bonds that may occur in any stable point along the chain, such as ethenyl and propenyl. For example, $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. For example, $C_{2-6}$ Alkynyl includes $C_2$, $C_3$, $C_4$, $C_5$, and $C_6$ alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. For example, $C_{3-8}$ cycloalkyl includes $C_3$, $C_4$, $C_5$, $C_6$, $C_7$, and $C_8$ cycloalkyl groups. Cycloalkyl also includes bicycloalkyl and tricycloalkyl, both of which include fused and bridged rings (e.g., norbornane and adamantane).

"Carbocycle" includes the specified number of carbon atoms in a cycloalkyl ring or a partially unsaturated cycloalkyl ring (e.g., cyclohexene and cyclopentadiene).

"Cyclic amine" is a hydrocarbon ring wherein one carbon atom of the ring has been replaced by a nitrogen atom. The cyclic amine can be unsaturated, partially saturated, or fully saturated. The cyclic amine can also be bicyclic, tricyclic, and polycyclic. Examples of cyclic amine include pyrrolidine and piperdine.

"Halo" or "halogen" refers to F, Cl, bromo, and iodo.

"Acyl" refers to an alkyl group terminated by a carbonyl (C=O) group. The acyl moiety is attached via the carbonyl group.

"Counterion" is used to represent a small, negatively charged species, such as chloride, bromide, hydroxide, acetate, and sulfate.

The group "$C_6H_4$" represents a phenylene.

"Lactone" refers to a ring containing a carboxyl group ($CO_2$).

"Lactam" refers to a ring containing an amido group (C(O)N).

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, and tetrahydronaphthyl.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl includes acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

Examples of heterocycles include, but are not limited to, decahydroquinolinyl, imidazolidinyl, imidazolinyl, indolinyl, isatinoyl, methylenedioxyphenyl, morpholinyl, octahydroisoquinolinyl, oxazolidinyl, oxindolyl, piperazinyl, piperidinyl, piperidonyl, 4-piperidonyl, piperonyl, pyranyl, pyrazolidinyl, pyrazolinyl, pyrrolidinyl, pyrrolinyl, tetrahydrofuranyl, tetrahydroisoquinolinyl, tetrahydroquinolinyl, 1-aza-bicyclo[2.2.2]octane, 2,5-diaza-bicyclo[2.2.2]octane, and 2,5-diaza-bicyclo[2.2.1]heptane. Also included are fused ring and spiro compounds containing, for example, the above heterocycles.

"Mammal" covers warm blooded mammals that are typically under medical care (e.g., humans and domesticated animals). Examples of mammals include feline, canine, equine, bovine, and human, as well as just human.

"Diseases" and "disorders" are used interchangeably.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached or reducing the symptoms of the disease state.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences,* 18th ed., Mack Publishing Company, Easton, Pa., 1990, p 1445.

"Therapeutically effective amount" includes an amount of a compound of the present invention that is effective when administered alone or in combination to treat obesity, diabetes, dyslipidemia, cardiovascular diseases, inflammatory disorder, hepatic disease, or another indication listed herein. "Therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Obesity is defined as having a body mass index (BMI) of 30 or above. The index is a measure of an individual's body weight relative to height. BMI is calculated by dividing body weight (in kilograms) by height (in meters) squared. Normal and healthy body weight is defined as having a BMI between 20 and 24.9. Overweight is defined as having a BMI$\geq$25. Obesity has reached epidemic proportions in the U.S., with 44 million obese Americans, and an additional eighty million deemed medically overweight.

Obesity is a disease characterized as a condition resulting from the excess accumulation of adipose tissue, especially adipose tissue localized in the abdominal area. It is desirable to treat overweight or obese patients by reducing their amount of adipose tissue, and thereby reducing their overall body weight to within the normal range for their sex and height. In this way, their risk for co-morbidities such as diabetes and cardiovascular disease will be reduced. It is also desirable to prevent normal weight individuals from accumulating additional, excess adipose tissue, effectively maintaining their body weights at a BMI<25, and preventing the development of co-morbidities. It is also desirable to control obesity, effectively preventing overweight and obese individuals from accumulating additional, excess adipose tissue, reducing the risk of further exacerbating their co-morbidities.

Type 2 Diabetes or Diabetes mellitus type 2 or (formerly called non-insulin-dependent diabetes mellitus (NIDDM), or adult-onset diabetes) is a metabolic disorder that is primarily characterized by insulin resistance, relative insulin deficiency, and hyperglycemia. The World Health Organization definition of diabetes is for a single raised glucose reading with symptoms otherwise raised values on two occasions, of either fasting plasma glucose$\geq$7.0 mmol/l (126 mg/dl) or with a Glucose tolerance test: two hours after the oral dose a plasma glucose≧11.1 mmol/l (200 mg/dl). Type 2 Diabetes is rapidly increasing in the developed world and there is some evidence that this pattern will be followed in much of the rest of the world in coming years. CDC has characterized the increase as an epidemic (Diabetes, Atlanta: Centres for Disease Control, Atlanta, Report no. 2007-05-24). In addition, whereas this disease used to be seen primarily in adults over age 40 (in contrast to Diabetes mellitus type 1), it is now increasingly seen in children and adolescents, an increase thought to be linked to rising rates of obesity in this age group.

Insulin resistance means that body cells do not respond appropriately when insulin is present. Unlike insulin-dependent diabetes mellitus (Type 1), the insulin resistance is generally "post-receptor", meaning it is a problem with the cells that respond to insulin rather than a problem with insulin production. Type 2 diabetes is presently of unknown etiology (i.e., origin). About 90-95% of all North American cases of diabetes are type 2, and about 20% of the population over the age of 65 has diabetes mellitus Type 2 (Nature, 2001, 414, 6865). Diabetes affects over 150 million people worldwide and this number is expected to double by 2025. About 55 percent of type 2 diabetics are obese-chronic obesity leads to increased insulin resistance that can develop into diabetes (Morbidity and Mortality Weekly Report 2008, 53, 1066). Type 2 diabetes is often associated with obesity, hypertension, elevated cholesterol (combined hyperlipidemia), and with the condition often termed Metabolic syndrome (it is also known as Syndrome X, Reavan's syndrome, or CHAOS). There are several drugs available for Type 2 diabetics, including metformin, thiazolidinediones, which increase tissue insulin sensitivity, α-glucosidase inhibitors which interfere with absorption of some glucose containing nutrients, and peptide analogs that must be injected.

Dyslipidemia is the presence of abnormal levels of lipids and/or lipoproteins in the blood. Lipids (fatty molecules) are transported in a protein capsule, and the density of the lipids and type of protein determines the fate of the particle and its influence on metabolism. Lipid and lipoprotein abnormalities are extremely common in the general population, and are regarded as a highly modifiable risk factor for cardiovascular disease due to the influence of cholesterol, one of the most clinically relevant lipid substances, on atherosclerosis. In addition, some forms may predispose to acute pancreatitis.

In western societies, most dyslipidemias are hyperlipidemias; that is, an elevation of lipids in the blood, often due to diet and lifestyle. The prolonged elevation of insulin levels can also lead to dyslipidemia. The most prevalent hyperlipidemias include: hypercholesterolemia, characterized by elevated cholesterol (usually LDL), hypertriglyceridemia, characterized by elevated triglycerides (TGs); hyperlipoproteinemia, characterized by elevated lipoproteins; hyperchylomicronemia, characterized by elevated chylomicrons; and combined hyperlipidemia, characterized by elevated LDL and triglycerides. Abnormal decreases in the levels of lipids and/or lipoproteins in the blood also can occur. These include hypocholesterolemia, characterized by lowered cholesterol (usually high density lipoprotein, or HDL); and abetalipoproteinemia, characterized by lowered beta lipoproteins.

Dyslipidemia contributes to the development of atherosclerosis. Causes may be primary (genetic) or secondary. Diagnosis is by measuring plasma levels of total cholesterol, TGs, and individual lipoproteins. Treatment is dietary changes, exercise, and lipid-lowering drugs. A linear relation probably exists between lipid levels and cardiovascular risk, so many people with "normal" cholesterol levels benefit from achieving still lower levels. Normal and abnormal lipid levels have been defined in the Third Report of the Expert Panel on Detection, Evaluation, and Treatment of High Blood Cholesterol in Adults. National Institutes of Health, National Heart, Lung, and Blood Institute, 2001.

The treatment of choice for dyslipidemias is lifestyle change, including diet and exercise. Drugs are the next step when lifestyle changes are not effective. Lipid lowering drugs include statins, nicotinic acid, bile acid sequestrants, fibrates, cholesterol absorption inhibitors, and combination treatments (e.g., niacin and a statin). These agents are not without adverse effects, including flushing and impaired glucose tolerance (nicotinic acid), bloating, nausea, cramping, and constipation (bile acid sequestrants). Bile acid sequestrants may also increase TGs, so their use is contraindicated in patients with hypertriglyceridemia. Fibrates potentiate muscle toxicity when used with statins, and may increase LDL in patients with high TGs.

Drugs enter the CNS from the systemic circulation by crossing the blood-brain barrier (BBB). The BBB is a highly specialized 'gate-keeper' that protects the brain by preventing the entry of many potentially harmful substances into the CNS from the systemic circulation. Much is known about the BBB, and of the physical-chemical properties required for compounds transported across it.

Drugs that do not cross the BBB into the CNS or that are readily eliminated through transport mechanisms (J. Clin. Invest. 1996, 97, 2517) are known in the literature and have low CNS activity due to their inability to develop brain levels necessary for pharmacological action. The BBB has at least one mechanism to remove drugs prior to their accumulation in the CNS. P-Glycoproteins (P-gp) localized in plasma membrane of the BBB can influence the brain penetration and pharmacological activity of many drugs through translocation across membranes. The lack of accumulation into the brain by some drugs can be explained by their active removal from the brain by P-gp residing in the BBB. For example, the typical opioid drug loperamide, clinically used as an antidiarrheal, is actively removed from the brain by P-gp, thus explaining its lack of opiate-like CNS effects. Another example is domperidone, a dopamine receptor blocker that participates in the P-gp transport (J. Clin. Invest. 1996, 97, 2517). Whereas dopamine receptor blockers that cross the BBB can be used to treat schizophrenia, the readily-eliminated domperidone can be used to prevent emesis, without the likelihood of producing adverse CNS effects.

In addition to the above compounds, agents possessing structural characteristics that retard or prevent BBB penetration or contribute to participation in active elimination processes have been identified in various classes of therapeutics. These include antihistamines (Drug Metab. Dispos. 2003, 31, 312), beta-adrenergic receptor antagonists (Eur. J. Clin. Pharmacol. 1985, 28, Suppl: 21; Br. J. Clin. Pharmacol., 1981, 11, 549), non-nucleoside reverse transcriptase inhibitors (NNRTIs, J. Pharm. Sci., 1999, 88, 950), and opioid antagonists. This latter group has been tested in relation to their activity in the gastrointestinal tract. These peripherally selective opioid antagonists are described in various US patents as being useful in the treatment of non-CNS pathologies in mammals, in particular those of the gastrointestinal tract (see U.S. Pat. No. 5,260,542; U.S. Pat. No. 5,434,171; U.S. Pat. No. 5,159,081; and U.S. Pat. No. 5,270,238).

Other types of non-brain penetrant compounds can be prepared through the creation of a charge within the molecule. Thus, the addition of a methyl group to the tertiary amine functionality of the drugs scopolamine or atropine, unlike the parent molecules, prevents their passage across the BBB through the presence of a positive charge. However, the new molecules (methyl-scopolamine and methyl-atropine) retain their full anticholinergic pharmacological properties. As such, these drugs can also be used to treat peripheral diseases, without the concern of adverse CNS effects. The quaternary ammonium compound methylnaltrexone is also used for the prevention and/or treatment of opioid-induced gastrointestinal side effects associated with opioid administration (*J. Pharmacol. Exp. Ther.* 2002, 300, 118).

The discovery that the anti-obesity activity of cannabinoid receptor blockers may in part be mediated by a non-CNS mechanism could make it beneficial for the compounds of the present invention to be peripherally restricted (i.e., have an inability or limited ability to cross the BBB, or be readily eliminated from the brain through active transport systems). It may be desirable for the compounds of the present invention to be peripherally restricted, which in turn will result in no or very limited CNS effects. Compounds that provide peripherally mediated anti-obesity, anti-diabetic, or anti-dyslipidemic properties should result in therapeutic agents with greater safety. It can be desirable that the compounds of the present invention, when administered in a therapeutically effective amount, have no or very limited CNS effects. It can also be desirable that the lack of CNS effects is a result of the compounds of the present invention having minimal brain concentrations when administered in therapeutically effective amounts. In this context, minimal brain concentrations means levels that are too low to be therapeutically effective for the treatment of a CNS indication or too low to cause significant or measurable deleterious or undesired side effects, or both.

Otenabant, CP-945548, is Compound AA, wherein A=2-chrorophenyl, B=4-chlorophenyl, X=C($R^{4a}$)($R^{4b}$), Y=C($R^{5a}$)($R^{5b}$), Z=C($R^{4c}$)($R^{4d}$), $R^1$=H, $R^2$=H, $R^{3a}$=H, $R^{3b}$=H, $R^{3c}$=H, $R^{3d}$=H, $R^{4a}$=H, $R^{4b}$=H, $R^{4c}$=H, $R^{4d}$=H, $R^{4a}$=NHEt, and $R^{5b}$=CONH$_2$ (see U.S. Pat. No. 7,129,239). Otenabant is a drug that was designed to cross the BBB, to suppress appetite via blockade of CB1 receptors in brain, and is indicated for the treatment of obesity. In compound AA, one of A, B, $R^1$, $R^{3a}$, $R^{3b}$, $R^{3c}$, $R^{3d}$, $R^{4a}$, $R^{4b}$, $R^{4c}$, $R^{4d}$, $R^{5a}$, $R^{5b}$, and $R^{5c}$ is suitably modified or replaced by a group capable of reducing or limiting the CNS (brain) levels of compound AA. This reduced or limited CNS activity occurs via at least one of A, B, $R^1$, $R^{3a}$, $R^{3b}$, $R^{3c}$, $R^{3d}$, $R^{4a}$, $R^{4b}$, $R^{4c}$ being a group that either limits compound AA's ability to cross the BBB relative to that of otenabant or enables it to be actively removed from the brain at a rate greater than that of otenabant. Examples of the amount of compound AA present in the brain can include (a) from 50, 55, 60, 65, 70, 75, 80, 85, 90, 91, 92, 93, 94, 95, 96, 97, 98, 99, to 100% lower than otenabant, (b) from 90, 91, 92, 93, 94, 95, 96, 97, 98, 99, to 100% lower than otenabant, and (c) from 98, 99, to 100% lower than otenabant, when administered at the same dosage.

Most methods of treating obesity are dependent on a significant reduction in energy intake, either by a decrease in food intake (e.g., sibutramine) or by inhibition of fat absorption (e.g., orlistat). In the present invention, adipose tissue may be reduced in the absence of a significant reduction in food intake. The weight loss, as a result of the present invention, comes from the treatment with a compound of the present invention, largely independent of, though not totally dissociated from, appetite and food intake. It can be desirable that adipose tissue loss occurs while food intake is maintained, increased or (a) about 1, 2, 3, 4, 5, 6, 7, 8, 9, 10, 11, 12, 13, 14, 15, 16, 17, 18, 19, or 20% below the normal range of the subject prior to being treated in accordance with the present invention (i.e., its pre-administration level), (b) about 1, 2, 3, 4, 5, 6, 7, 8, 9, 10, 11, 12, 13, 14, or 15% below its pre-administration level, (c) about 1, 2, 3, 4, 5, 6, 7, 8, 9, or 10% below its pre-administration level, or (d) about 1, 2, 3, 4, or 5% below its pre-administration level.

In some cases, loss of adipose tissue can be accompanied by a concomitant loss of lean muscle mass. This is particularly evident in cancer patients who show a generalized wasting of body tissues, including adipose tissue and lean muscle mass. In the present invention, however, it can be desirable for body fat to be significantly reduced in the absence of a significant reduction in lean body mass. Adipose tissue loss comes from treatment with a compound of the present invention, independent of a significant change in lean body mass. Thus, adipose tissue loss can occur while lean body mass is maintained, increased, or (a) is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% below the normal range of the subject prior to being treated in accordance with the present invention (i.e., its pre-administration level), (b) is no more than about 1, 2, 3, 4, 5, 6, 7, 8, 9, 10, 11, 12, 13, 14, or 15% below pre-administration levels, (c) is no more than about 1, 2, 3, 4, 5, 6, 7, 8, 9, or 10% below pre-administration levels, or (d) is no more than about 1, 2, 3, 4, or 5% below pre-administration levels.

In some cases, loss of adipose tissue can be accompanied by a concomitant loss of water mass. This is particularly evident with diet regimens that promote dehydration. In the present invention, it can be desirable for body fat to be significantly reduced in the absence of a significant reduction in water mass. In other words, adipose tissue loss comes from treatment with a compound of the present invention, independent of a significant change in water mass. It can be desirable that adipose tissue loss occurs while water mass is maintained, increased, or (a) is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% below the normal range of the subject prior to being treated in accordance with the present invention (i.e., its pre-administration level), (b) is no more than about 1, 2, 3, 4, 5, 6, 7, 8, 9, 10, 11, 12, 13, 14, or 15% below pre-administration levels, (c) is no more than about 1, 2, 3, 4, 5, 6, 7, 8, 9, or 10% below pre-administration levels, or (d) is no more than about 1, 2, 3, 4, or 5% below pre-administration levels.

Sibutramine and orlistat are currently marketed for use in the treatment of obesity, albeit weight loss is achieved through entirely different mechanism of action. Sibutramine inhibits the neuronal reuptake of serotonin and noradrenaline, and orlistat inhibits gut lipase enzymes that are responsible for breaking down ingested fat.

Cannabinoid receptor blockers can promote weight loss through inhibition of peripheral cannabinoid receptors, a mechanism entirely different from appetite suppressants, gut lipase inhibitors, and other agents with similar indications (e.g., serotonin agonists, leptin, fatty acid synthase inhibitors, and monoamine oxidase (MAO) inhibitors). Co-administration of a cannabinoid receptor blocker together with one or more other agents that are useful for treating the indications described above (e.g., obesity, diabetes, dyslipidemia, cardiovascular disorders, inflammatory disorders, hepatic disorders, and a combination thereof) is expected to be beneficial, by producing, for example, either additive or synergistic effects. Examples of additional agents include an appetite suppressant, a lipase inhibitor, and a MAO inhibitor (e.g., MAO-B and a combination of MAO-A/B). Therefore, the present invention provides a method of treating obesity, diabetes, dyslipidemia, cardiovascular disorders, inflammatory disorders, and/or hepatic disorders, and a combination thereof, comprising administering a therapeutically effective amount of a compound of the present invention and a second component effective for treating the desired indication.

Examples of second components include anti-obesity agents, which include, but are not limited to: 1) growth hormone secretagogues; 2) growth hormone secretagogue receptor agonists/antagonists; 3) melanocortin agonists; 4) Mc4r (melanocortin 4 receptor) agonists; 5) .beta.-3 agonists; 7) 5HT2C (serotonin receptor 2C) agonists; 8) orexin antagonists; 9) melanin concentrating hormone antagonists; 10) melanin-concentrating hormone 1 receptor (MCH1R) antagonists; 11) melanin-concentrating hormone 2 receptor (MCH2R) agonist/antagonists; 12) galanin antagonists; 13) CCK agonists; 14) CCK-A (cholecystokinin-A) agonists; 16) corticotropin-releasing hormone agonists; 17) NPY 5 antagonists; 18) NPY 1 antagonists; 19) histamine receptor-3 (H3) modulators; 20) histamine receptor-3 (H3) blockers; 21)β-hydroxy steroid dehydrogenase-1 inhibitors (.beta.-HSD-1); 22) PDE (phosphodiesterase) inhibitors; 23) phosphodiesterase-3B (PDE3B) inhibitors; 24) NE (norepinephrine) transport inhibitors; 25) non-selective serotonin/norepinephrine transport inhibitors, such as sibutramine, phentermine, or fenfluramine; 26) ghrelin antagonists; 28) leptin derivatives; 29) BRS3 (bombesin receptor subtype 3) agonists; 30) CNTF (Ciliary neurotrophic factors); 31) CNTF derivatives, such as axokine (Regeneron); 32) monoamine reuptake inhibitors; 33) UCP-1 (uncoupling protein-1), 2, or 3 activators; 34) thyroid hormone .beta. agonists; 35) FAS (fatty acid synthase) inhibitors; 37) DGAT2 (diacylglycerol acyltransferase 2) inhibitors; 38) ACC2 (acetyl-CoA carboxylase-2) inhibitors; 39) glucocorticoid antagonists; 40) acyl-estrogens; 41) lipase inhibitors, such as orlistat (Xenical®); 42) fatty acid transporter inhibitors; 43) dicarboxylate transporter inhibitors; 44) glucose transporter inhibitors; 45) phosphate transporter inhibitors; 46) serotonin reuptake inhibitors; 47) Metformin (Glucophage®); 48) Topiramate (Topimax®); 49) opiate antagonists such as naltrexone, 50) the non-selective transport inhibitor bupropion, and/or 51) MAO inhibitors.

Examples of MAO inhibitors include Moclobemide; Brofaromine; BW A616U; Ro 41-1049; RS-2232; SR 95191; Harmaline; Harman; Amiflamine; BW 1370U87; FLA 688; FLA 788; Bifemelane; Clorgyline; LY 51641; MDL 72,394; 5-(4-Benzyloxyphenyl)-3-(2-cyanoethyl)-(3H)-1,3,4-oxadiazol-2-one; 5-(4-Arylmethoxyphenyl)-2-(2-cyanoethyl) tetrazoles; Lazabemide; Ro 16-6491; Almoxatone; XB308; RS-1636; RS-1653; NW-1015; SL 340026;. L-selegiline; Rasagiline; Pargyline; AGN 1135; MDL 72,974; MDL 72,145; MDL 72,638; LY 54761; MD 780236; MD 240931; Bifemelane; Toloxatone; Cimoxatone; Iproniazid; Phenelzine; Nialamide; Phenylhydrazine; 1-Phenylcyclopropylamine; Isocarboxazid; and, Tranylcypromine. Additional examples of MAO inhibitors can be found in USPA 2007/0004683; U.S. Ser. No. 11/445,044; USPA 2007/0015734; and U.S. Ser. No. 11/424,274.

Examples of diabetes disorders include treating Type 1 diabetes, Type 2 diabetes, inadequate glucose tolerance, and insulin resistance.

Examples of second components useful for treating diabetes include (a) insulin sensitizers including (i) PPAR-γ agonists such as the glitazones (e.g. troglitazone, pioglitazone, englitazone, MCC-555, rosiglitazone), and compounds disclosed in WO97/27857, 97/28115, 97/28137, and 97/27847; and (ii) biguanides such as metformin and phenformin; (b) insulin or insulin mimetics; (c) sulfonylureas such as tolbutamide and glipizide, or related materials; (d) α-glucosidase inhibitors (e.g., acarbose); (e) cholesterol lowering agents such as (i) HMG-CoA reductase inhibitors (lovastatin, simvastatin, pravastatin, fluvastatin, atorvastatin, rivastatin, and other statins), (ii) sequestrants (e.g., cholestyramine, colestipol, and dialkylaminoalkyl derivatives of a cross-linked dextran), (iii) nicotinyl alcohol, nicotinic acid or a salt thereof, (iv) PPAR-α agonists (e.g., fenofibric acid derivatives including gemfibrozil, clofibrate, fenofibrate, and bezafibrate), (v) inhibitors of cholesterol absorption (e.g., β-sitosterol) and acyl CoA:cholesterol acyltransferase inhibitors (e.g., melinamide), and (vi) probucol; (f) PPAR-α/γ agonists; (g) antiobesity compounds (described previously); (h) ileal bile acid transporter inhibitors; (i) insulin receptor activators, (j) dipeptidyl peptidase IV, or DPP-4 inhibitors (sitagliptin, vildagliptin and other DPP-4 inhibitors (k) exenatide, (l) pramlintide, (m) FBPase inhibitors, (n) glucagon receptor antagonists, (o) glucagon-like peptide-1, and (p) the glucagon-like peptide-1 analogues (liraglutide, and others).

The compounds of the present invention are expected to be CB1 receptor blockers (e.g., antagonists/inverse agonists) and are expected to be useful for treating diseases mediated by the $CB_1$ receptor. The compounds of the present are expected to possess an affinity in vitro for the central and/or peripheral cannabinoid receptors under the experimental conditions described by Devane et al., *Molecular Pharmacology*, 1988, 34, 605-613. The compounds according to the invention are also expected to possess an affinity for the cannabinoid receptors present on preparations of electrically stimulated isolated organs. These tests can be performed on guinea-pig ileum and on mouse vas deferens according to Roselt et al., *Acta Physiologica Scandinavia* 1975, 94, 142-144, and according to Nicolau et al., *Arch. Int. Pharmacodyn*, 1978, 236, 131-136.

An inverse agonist is compound that not only blocks the action of the endogenous agonist at the receptor, but also exhibits its own activity which is usually the opposite of that shown by the agonist. Inverse agonists are also effective against certain types of receptors (e.g. certain histamine receptors/GABA receptors) that have intrinsic activity without the interaction of a ligand upon them (also referred to as 'constitutive activity').

CB1 receptor affinities can be determined using membrane preparations of Chinese hamster ovary (CHO) cells in which the human cannabinoid CB1 receptor is stably transfected (*Biochem J.* 1991, 279, 129-134) in conjunction with [3H] CP-55,940 as radioligand. After incubation of a freshly prepared cell membrane preparation with the [3H]-radioligand, with or without addition of test compound, separation of bound and free ligand is performed by filtration over glass fiber filters. Radioactivity on the filter is measured by liquid scintillation counting. The $IC_{50}$ values can be determined from at least three independent measurements.

As noted above, the compounds of the present invention are expected to be cannabinoid receptor antagonists or inverse agonists (e.g., have activity at ≦10 μM). Representative compounds have been tested and shown to be active (e.g., see Tables A, B, and C). Other examples of desired activity include ≦1 μM, ≦100 nM, ≦10 nM, and ≦1 nM.

Formulations and Dosages

In the present invention, the compound(s) of the present invention can be administered in any convenient manner (e.g., enterally or parenterally). Examples of methods of administration include orally and transdermally. One skilled in this art is aware that the routes of administering the compounds of the present invention may vary significantly. In addition to other oral administrations, sustained release compositions may be favored. Other acceptable routes may include injections (e.g., intravenous, intramuscular, subcutaneous, and intraperitoneal); subdermal implants; and, buccal, sublingual, topical, rectal, vaginal, and intranasal administrations. Bioerodible, non-bioerodible, biodegradable, and non-biodegradable systems of administration may also be used. Examples of oral formulations include tablets, coated tablets, hard and soft gelatin capsules, solutions, emulsions, and suspensions.

If a solid composition in the form of tablets is prepared, the main active ingredient can be mixed with a pharmaceutical vehicle, examples of which include silica, starch, lactose, magnesium stearate, and talc. The tablets can be coated with sucrose or another appropriate substance or they can be treated so as to have a sustained or delayed activity and so as to release a predetermined amount of active ingredient continuously. Gelatin capsules can be obtained by mixing the active ingredient with a diluent and incorporating the resulting mixture into soft or hard gelatin capsules. A syrup or elixir can contain the active ingredient in conjunction with a sweetener, which is typically calorie-free, an antiseptic (e.g., methylparaben and/or propylparaben), a flavoring, and an appropriate color. Water-dispersible powders or granules can contain the active ingredient mixed with dispersants or wetting agents or with suspending agents such as polyvinylpyrrolidone, as well as with sweeteners or taste correctors. Rectal administration can be effected using suppositories, which are prepared with binders melting at the rectal temperature (e.g., cocoa butter and/or polyethylene glycols). Parenteral administration can be effected using aqueous suspensions, isotonic saline solutions, or injectable sterile solutions, which contain pharmacologically compatible dispersants and/or wetting agents (e.g., propylene glycol and/or polyethylene glycol). The active ingredient can also be formulated as microcapsules or microspheres, optionally with one or more carriers or additives. The active ingredient can also be presented in the form of a complex with a cyclodextrin, for example α-, β-, or γ-cyclodextrin, 2-hydroxypropyl-β-cyclodextrin, and/or methyl-β-cyclodextrin.

The dose of the compound of the present invention administered daily will vary on an individual basis and to some extent may be determined by the severity of the disease being treated (e.g., obesity, diabetes, and cardiometabolic disorders). The dose of the compound of the present invention will also vary depending on the compound administered. Examples of dosages of compounds of the present invention include from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 15, 20, 25, 30, 35, 40, 45, 50, 55, 60, 65, 70, 76, 80, 85, 90, 95, to 100 mg/kg of mammal body weight. The compound can be administered in a single dose or in a number of smaller doses over a period of time. The length of time during which the compound is administered varies on an individual basis, and can continue until the desired results are achieved (i.e., reduction of body fat, or prevention of a gain in body fat). Therapy could, therefore, last from 1 day to weeks, months, or even years depending upon the subject being treated, the desired results, and how quickly the subject responds to treatment in accordance with the present invention.

A possible example of a tablet of the present invention is as follows.

| Ingredient | mg/Tablet |
|---|---|
| Active ingredient | 100 |
| Powdered lactose | 95 |
| White corn starch | 35 |
| Polyvinylpyrrolidone | 8 |

| Ingredient | mg/Tablet |
|---|---|
| Na carboxymethylstarch | 10 |
| Magnesium stearate | 2 |
| Tablet weight | 250 |

A possible example of a capsule of the present invention is as follows.

| Ingredient | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

In the above capsule, the active ingredient has a suitable particle size. The crystalline lactose and the microcrystalline cellulose are homogeneously mixed with one another, sieved, and thereafter the talc and magnesium stearate are admixed. The final mixture is filled into hard gelatin capsules of suitable size.

A possible example of an injection solution of the present invention is as follows.

| Ingredient | mg/Solution |
|---|---|
| Active substance | 1.0 mg |
| 1 N HCl | 20.0 µl |
| acetic acid | 0.5 mg |
| NaCl | 8.0 mg |
| Phenol | 10.0 mg |
| 1 N NaOH | q.s. ad pH 5 |
| $H_2O$ | q.s. ad 1 mL |

SYNTHESIS

The compounds of the present invention can be prepared in a number of ways known to one skilled in the art of organic synthesis (e.g., *J Med Chem* 1999, 42, 833; U.S. Pat. No. 7,129,239; US 2006/0241120 A1); US 2004/0092520). The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. In particular, suitable protecting groups for and amino groups (NH-PG) include acetyl, trifluoroacetyl, t-butoxycarbonyl (BOC), benzyloxycarbonyl (CBz), and 9-fluorenymethyleneoxycarbonyl (Fmoc). An authoritative account describing the many alternatives to the trained practitioner is Greene and Wuts (*Protective Groups In Organic Synthesis*, Wiley and Sons, 1991).

Scheme 1 shows the synthesis of adenine derivatives following the general route as described by Chorvat et al., J Med. Chem., 42, 833 (1999). Treatment of 5-amino-4,6-dichloropyrimidine ($R_1$=H, available from Sigma-Aldrich; or $R_1$=CH$_3$, Albert et al., J Chem. Soc. 3832 (1954)) with an aniline such as 4-chloroaniline in 2-ethoxyethanol at elevated temperature from 24-48 hours can produce the chlorodiaminopyrimidine (step a). Aroylation of the di-amino compound can be accomplished using an aroyl or heteroaroyl chloride in a suitable solvent such as methylene chloride in the presence of a base such as triethylamine (step b). Heating the amides at elevated temperatures in a solvent such as toluene containing phosphorus oxychloride in the presence of a base such as pyridine or triethylamine should afford the cyclized purine intermediate (step c). Treatment of the chloro purine with an amine such as 4-ethylaminopiperidine-4-carboxamide (prepared as described in U.S. Pat. No. 3,161,644; van de Westeringh, et al., J. Med. Chem., 7, 619 (1964); Metwally et al., J. Med. Chem., 41, 5084 (1998)) in a solvent such as ethanol, acetone, water and combinations thereof in the presence of an amine such as triethylamine should produce the aminopurine adduct (step d). The secondary amine can be protected using di-t-butyl-dicarbonate (t-Boc anhydride) in the presence of a base such as triethylamine, and the ester can then be hydrolyzed with lithium hydroxide in aqueous THF solution to afford carboxylic acid (step f). Coupling of the acid with an amino acid ester such as alanine (Q=Me) in the presence of isobutylchloroformate (IBCF) and N-methylmorpholine in methylene chloride at 0° C. to room temperature should yield the ester (step f). Hydrolysis of the ester as described above should afford the acid (step g) which can be de-protected using trifluoroacetic acid in methylene chloride to give the free amino acid, or coupled with ammonia using isobutylchloroformate (IBCF) and N-methylmorpholine in methylene chloride at 0° C. to room temperature to form the carboxamide (step h).

Scheme 1

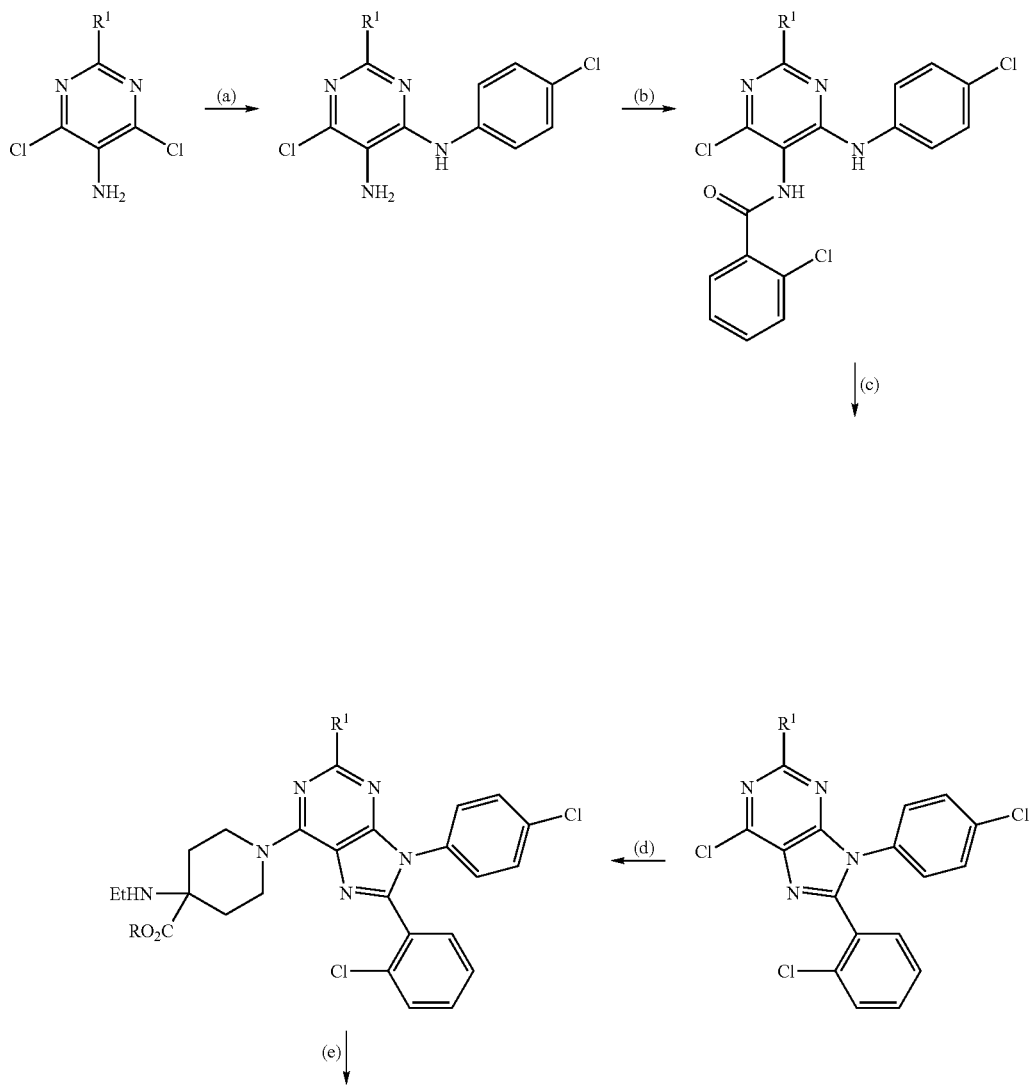

-continued

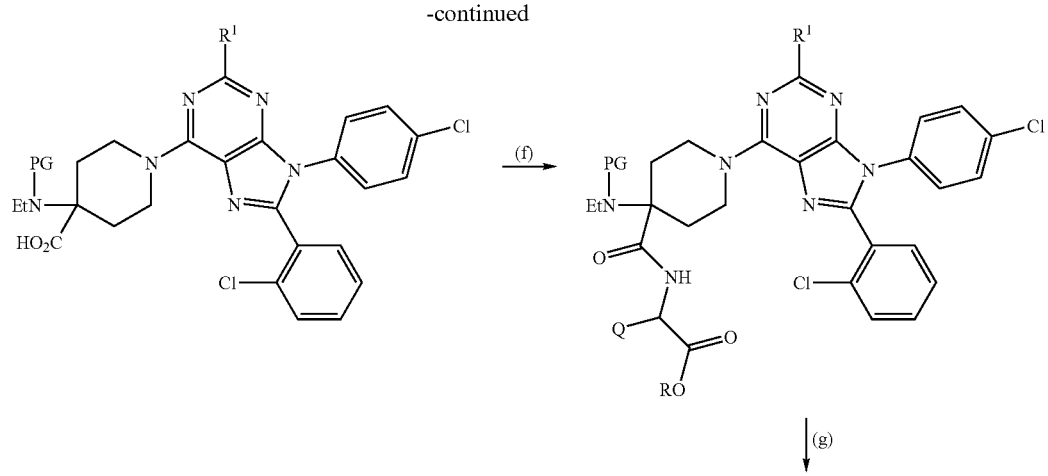

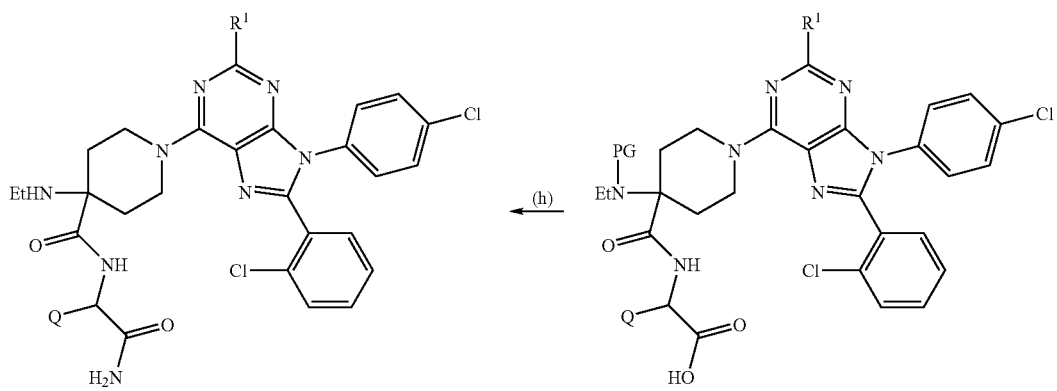

Scheme 2 gives a synthesis of purine derivatives with various functionalities on a phenyl group. Condensation of 5-amino-4,6-dichloropyrimidine ($R_1$=H, available from Sigma-Aldrich; or $R_1$=$CH_3$, Albert et al., J Chem. Soc. 3832 (1954)) with an aniline such as 4-methoxyaniline in 2-ethoxyethanol at elevated temperature from 24-48 hours can produce the methoxydiaminopyrimidine (step a). Aroylation of the di-amino compound can be accomplished using an aroyl- or hetero-aroyl chloride in a suitable solvent such as methylene chloride in the presence of a base such as triethylamine (step b). Heating the amides at elevated temperatures in a solvent such as toluene containing phosphorus oxychloride in the presence of a base such as pyridine or triethylamine should afford the cyclized purine intermediate (step c). Treatment of the chloro purine with an amine such as the 4-ethylaminopiperidine-4-carboxamide (prepared as described in U.S. Pat. No. 3,161,644; van de Westeringh, et al., J. Med. Chem., 7, 619 (1964); Metwally et al., J. Med. Chem., 41, 5084 (1998)) in a solvent such as ethanol, acetone, water and combinations thereof in the presence of an amine such as triethylamine should produce the aminopurine adduct (step d). Removal of the methyl group of the methoxyphenyl ring can be accomplished using [TMAH][$Al_2Cl_7$](Kempermann, et al., European J. Org. Chem., 1681 (2003)) in methylene chloride at room temperature to the solvent reflux temperature to provide the phenol (step e). Alkylation of the phenol with ethyl bromoacetate in acetone in the presence of potassium carbonate at room temperature to solvent reflux temperature can yield the ester (step f). Protection of the secondary amino group using di-t-butyl-dicarbonate (t-Boc anhydride) in the presence of a base such as triethylamine, and hydrolysis of the ester using lithium hydroxide in aqueous THF solution should afford the carboxylic acid (step g). Coupling of the acid with an ammonia in the presence of isobutylchloroformate (IBCF) and N-methylmorpholine in methylene chloride at 0° C. to room temperature, and deprotection of the amino group using trifluoroacetic acid in methylene chloride should yield the carboxamide (step h).

Scheme 2

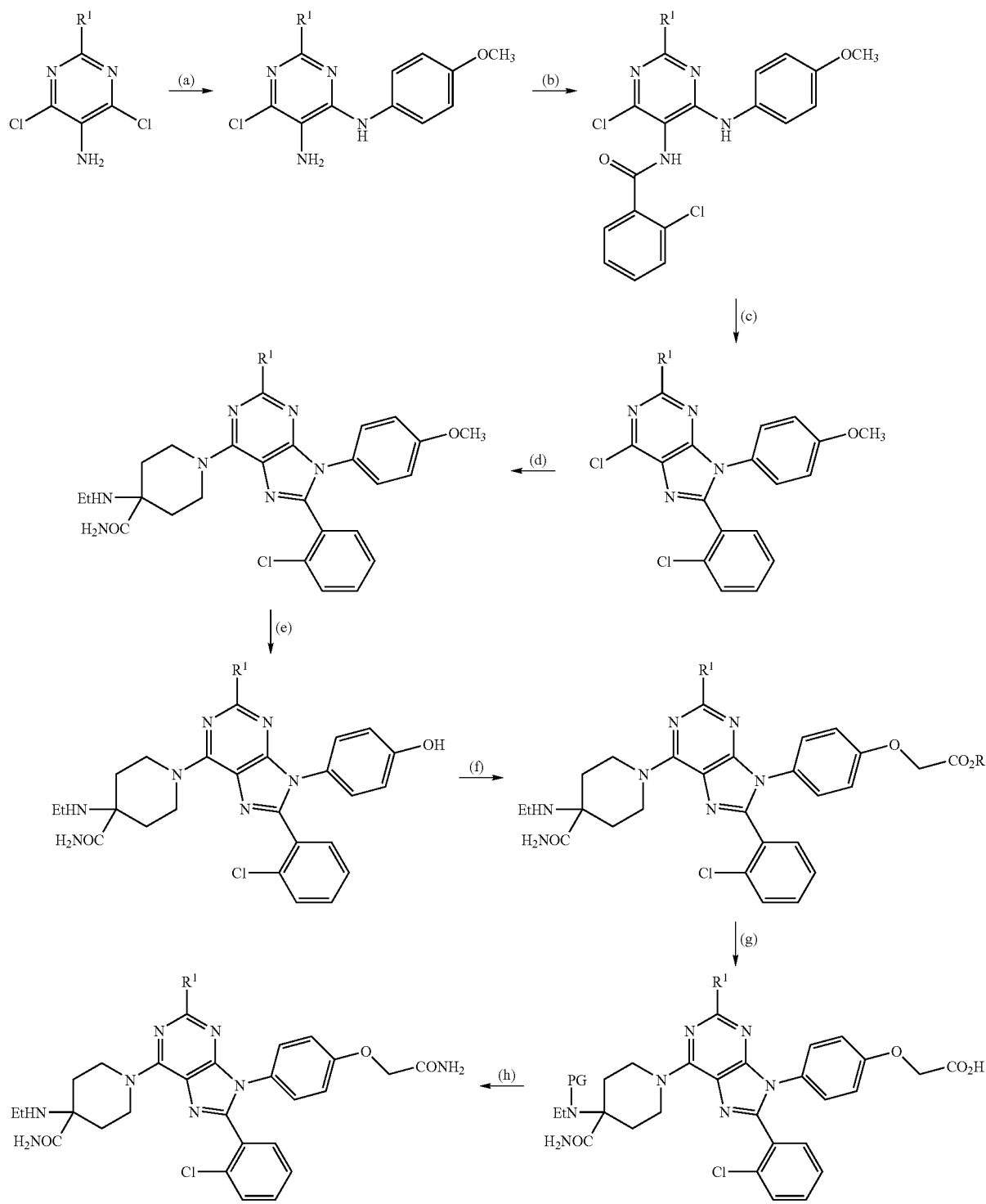

Scheme 3 shows the preparation of phenyl groups with amino acids coupled via carboxylic acids attached directly or on pendants to the ring. The forementioned 4-chlorophenyl aniline derivative can be treated with a cyanobenzoyl chloride to afford the benzamide (step a). Cyclization as previously described above can give the purine derivative (step b).

Hydration of the nitrile group using sulfuric acid or other acids and water should give the carboxamide (step c). The carboxamide can be converted to the ester using anhydrous HCl in methanol at zero degrees to room temperature (step d). Treatment of the ester with the forementioned 4-ethylaminopiperidine-4-carboxamide in a solvent such as ethanol, acetone, water and combinations thereof in the presence of an amine such as triethylamine should produce the aminopurine adduct (step e). Protection of the secondary amino group using di-t-butyl-dicarbonate (t-Boc anhydride) in the presence of a base such as triethylamine, and hydrolysis of the ester using lithium hydroxide in aqueous THF solution should afford the carboxylic acid (step f). Coupling of the acid with an amino acid ester such as alanine (Q=Me) in the presence of isobutylchloroformate (IBCF) and N-methylmorpholine in methylene chloride at 0° C. to room temperature should yield the amino acid ester adduct (step g).

Hydrolysis of the ester as described above and de-protection of the amino group using trifluoroacetic acid in methylene chloride can give the free amino acid. Alternatively, coupling of the protected amino acid with ammonia using isobutylchloroformate (IBCF) and N-methylmorpholine in methylene chloride at 0° C. to room temperature can form the carboxamide which upon amino group deprotection using trifluoroacetic acid in methylene chloride should give the amino carboxamide adduct (step h).

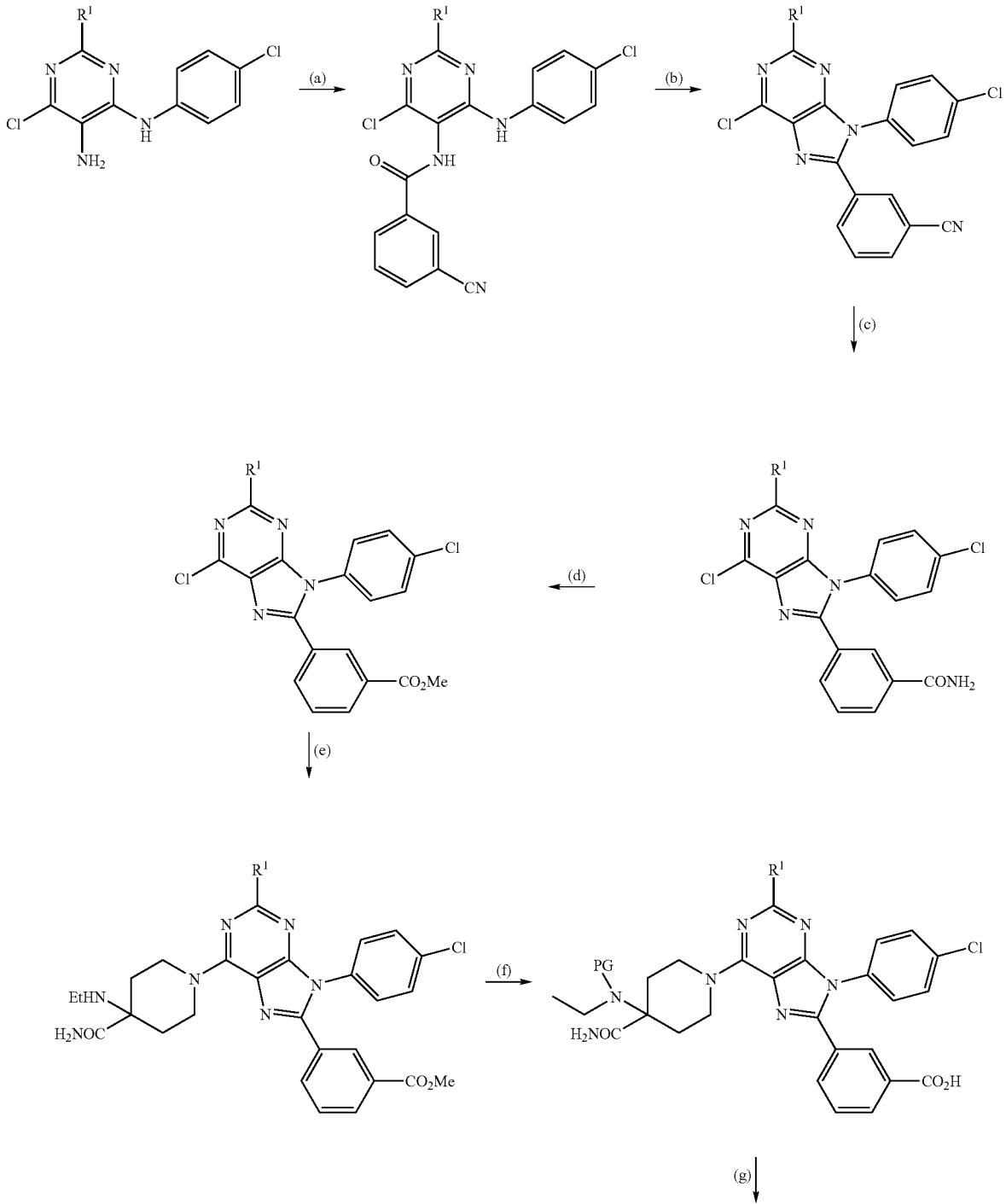

Scheme 3

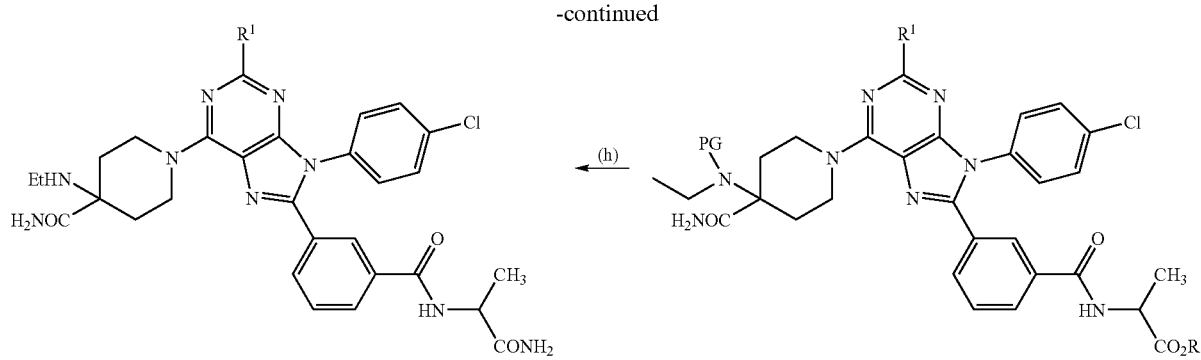

Scheme 4 shows a method of preparing carboxamide and carboxylic acid adducts via amino groups on the phenyl rings. The forementioned aminodichloropyrimidine can be treated with a nitroaniline at elevated temperatures as previously described to produce the nitrophenyl adduct (step a). Aroylation (step b) followed by cyclization (step c) and subsequent treatment with the forementioned 4-ethylaminopiperidine-4-carboxamide in a solvent such as ethanol, acetone, water and combinations thereof in the presence of an amine such as triethylamine should produce the aminopurine adduct (step d). Protection of the secondary amino group using di-t-butyl-dicarbonate (t-Boc anhydride) in the presence of a base such as triethylamine should afford the carbamate (step e), and reduction of the nitro group with sodium dithionite in aqueous dioxane containing concentrated ammonium hydroxide solution at room or slightly elevated temperatures can yield the aniline (step f). Acylation of the aromatic amine with ethyl malonylchloride in a solvent such as methylene chloride in the presence of a base such as triethylamine should afford the ester (step g). Hydrolysis of the ester using lithium hydroxide in aqueous THF solution should afford the carboxylic acid which upon coupling with ammonia in the presence of isobutylchloroformate (IBCF) and N-methylmorpholine in methylene chloride at 0° C. to room temperature, and deprotecting the amine using trifluoroacetic acid in methylene chloride should give the di-carboxamide adduct (step h).

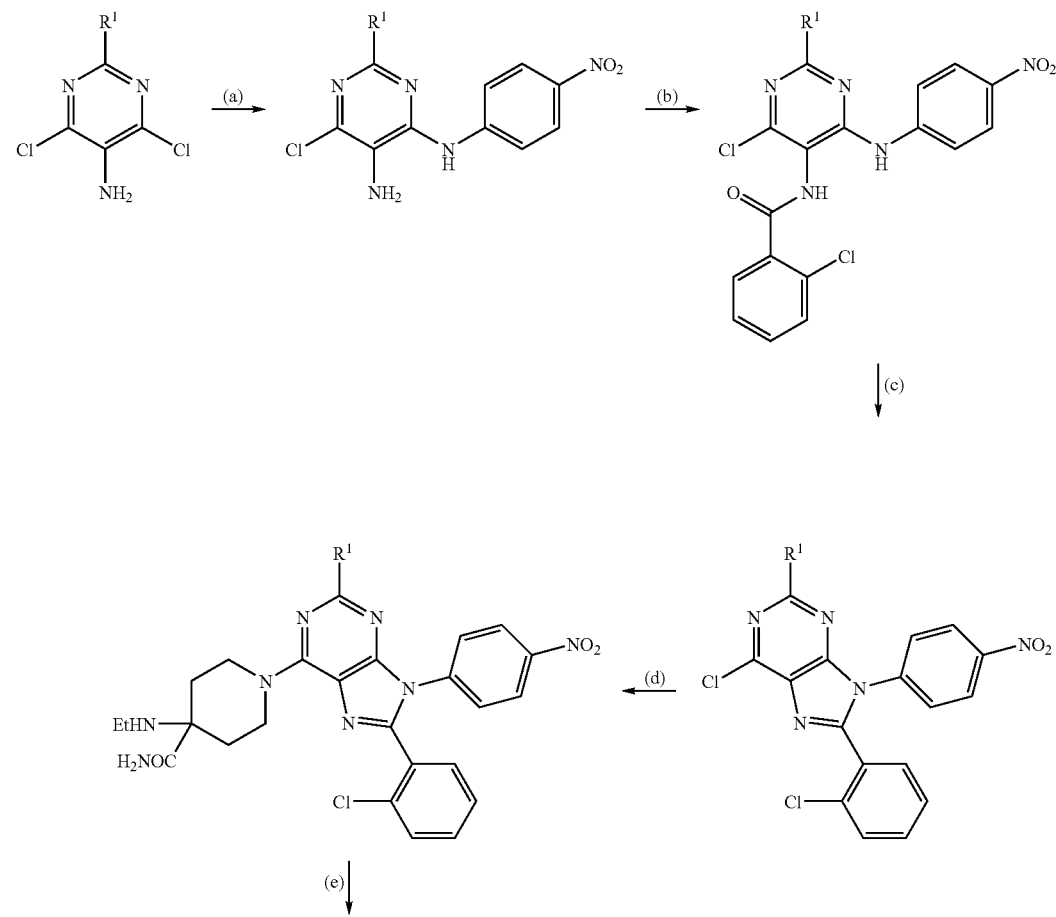

Scheme 4

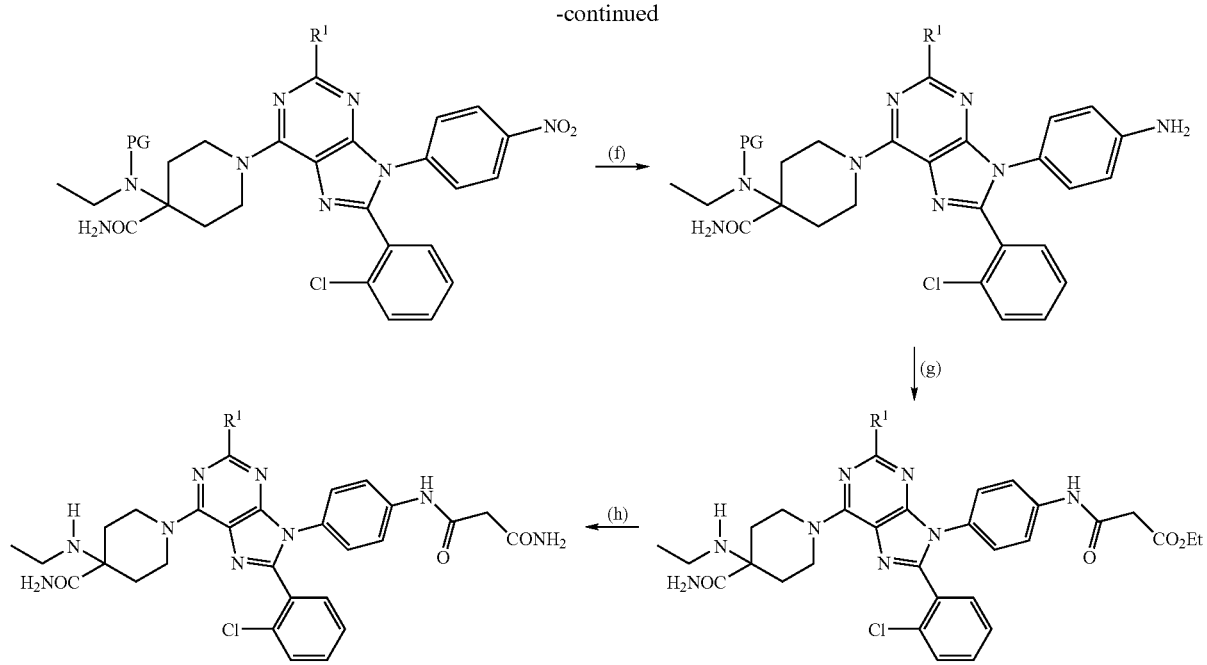

Scheme 5 shows the synthesis of purine analogs with functionalized pendants on the carbon atom of the pyrimidine ring. The indicated di-tosylated pyrimidine derivative can be prepared from condensation of diethyl nitromalonate (Sigma-Aldrch) and maloamamidine (Sigma-Aldrich) using standard pyrimidine synthesis procedures (Albert et al., J. Chem Soc., 3832 (1954; Hymans, J. Hetrerocycl. Chem., 13, 1141 (1976)) followed by the procedure of Cain and Beck, Heterocycles, 55, 439 (2001). Condensation of this reagent with 4-chloroaniline (step a), followed by aroylation with 2-chlorobenzoyl chloride (step b) and subsequent cyclization by methods previously described can afford the purine intermediate (step c). Treatment of the carboxamido compound in methanol using anhydrous HCl in methanol at zero degrees to room temperature should afford the methyl ester (step d). Treatment of the ester with the forementioned 4-ethylaminopiperidine-4-carboxamide in a solvent such as ethanol, acetone, water and combinations thereof in the presence of an amine such as triethylamine should produce the aminopurine adduct (step e). Protection of the secondary amino group using di-t-butyl-dicarbonate (t-Boc anhydride) in the presence of a base such as triethylamine, and hydrolysis of the ester using lithium hydroxide in aqueous THF solution should afford the carboxylic acid (step f). Coupling of the acid with an amino acid ester such as serine (Q=$CH_2OH$) in the presence of isobutylchloroformate (IBCF) and N-methylmorpholine in methylene chloride at 0° C. to room temperature should yield the amino acid ester adduct (step g). Hydrolysis of the ester as, described above, and conversion of the acid with anhydrous ammonia in the presence of isobutylchloroformate (IBCF) and N-methylmorpholine in methylene chloride at 0° C. to room temperature can produce the carboxamide (step h). De-protection of the amino group using trifluoroacetic acid in methylene chloride can give the free amino acid (step i).

Scheme 5

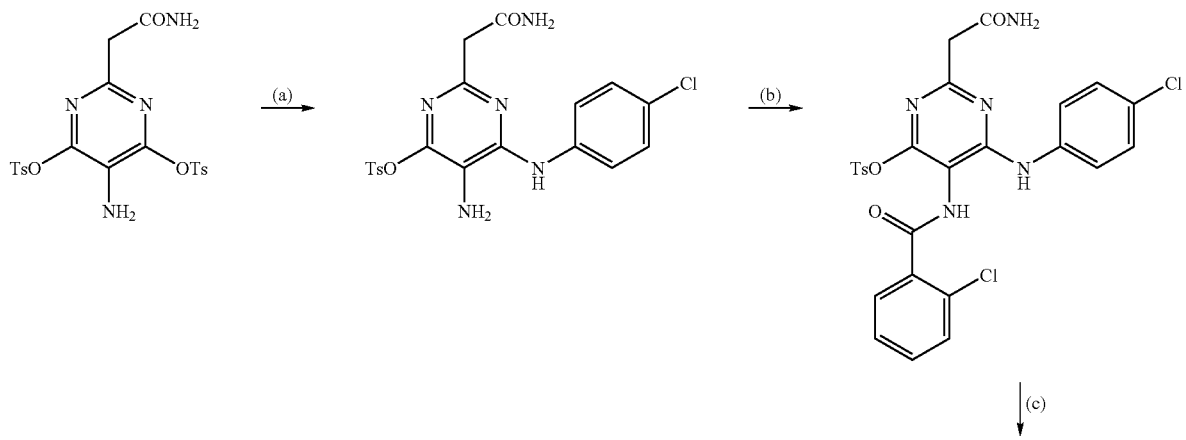

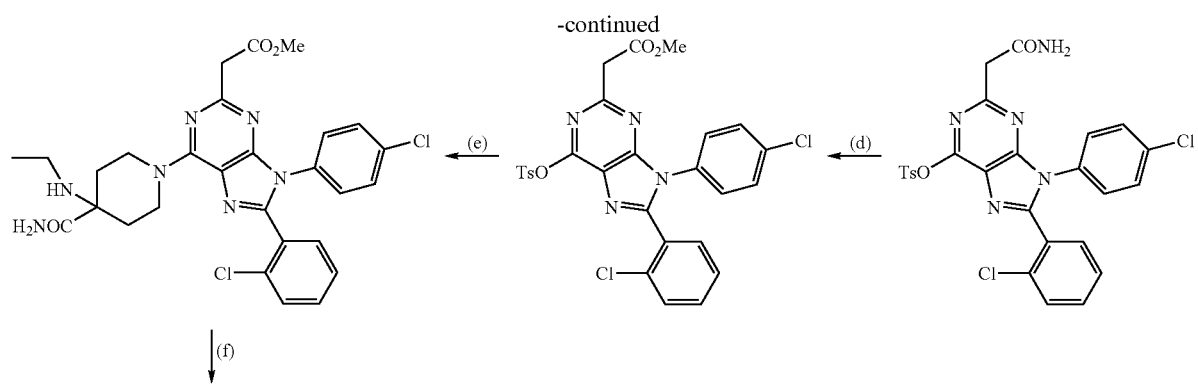

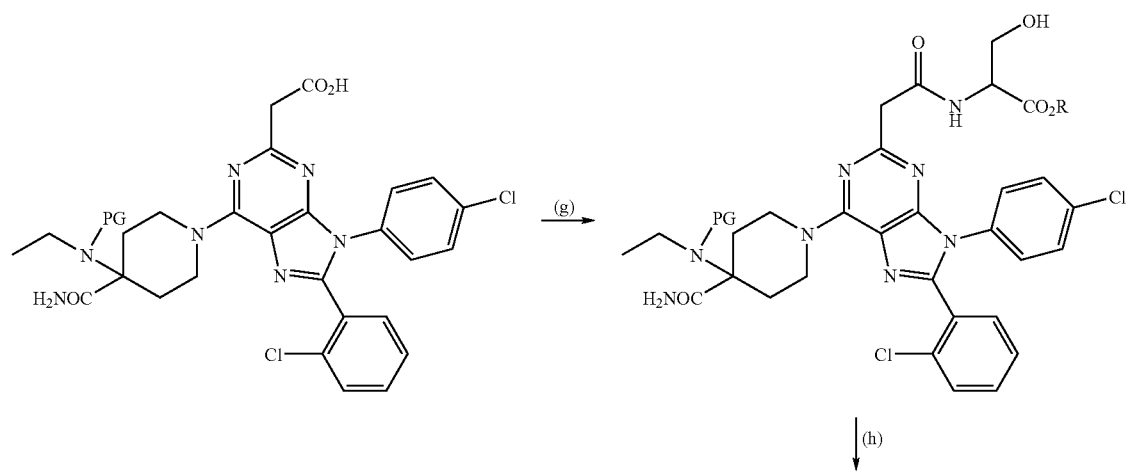

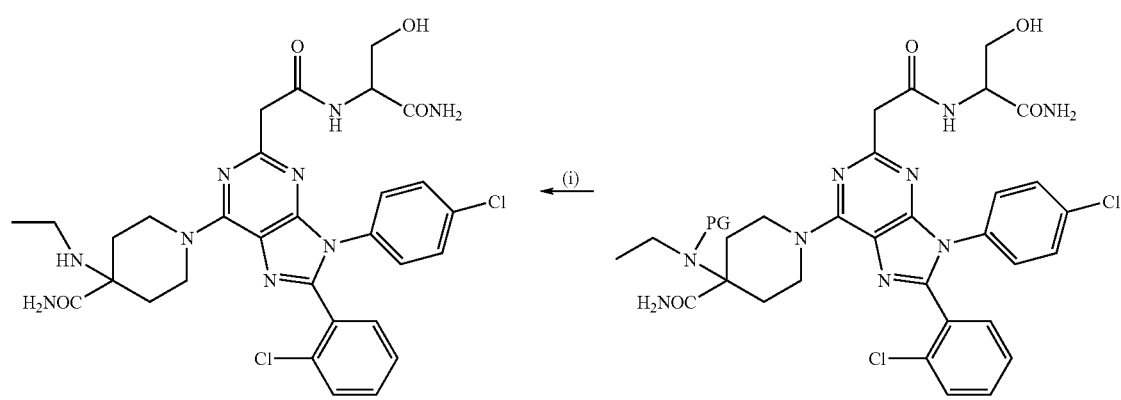

Scheme 6 shows the synthesis of amino purine adducts that have amino acid pendants on the cyclic amino groups. The chloro-purine intermediate previously described above, can be treated with ethyl 2-mopholininocarboxylate (Henegar, J. Org Chem., 3662, (2008)) in a solvent such as ethanol, acetone, water and combinations thereof in the presence of an amine such as triethylamine to produce the aminopurine adduct (step a). Hydrolysis of the ester with lithium hydroxide in aqueous THF solution will yield the carboxylic acid (step b), and condensation with an amino ester, such as alanine, in the presence of isobutylchloroformate (IBCF) and N-methylmorpholine in methylene chloride at 0° C. to room temperature should yield the amino acid ester adduct (step c). Hydrolysis of the ester as, described above, and conversion of the acid with anhydrous ammonia in the presence of isobutylchloroformate (IBCF) and N-methylmorpholine in methylene chloride at 0° C. to room temperature can produce the carboxamide (step d). Alternatively, the amino acid adduct from step c can be treated with a second amino ester such as glycine in the presence of isobutylchloroformate (IBCF) and N-methylmorpholine in methylene chloride at 0° C. to room temperature to produce the diamino ester adduct which can be hydrolyzed to the carboxylic acid, or converted to carboxamide as described above (step e).

yield the carboxylic acid (step b), and condensation with an amino ester, such as alanine, in the presence of isobutylchloroformate (IBCF) and N-methylmorpholine in methylene chloride at 0° C. to room temperature should yield the amino acid ester adduct (step c). Hydrolysis of the ester with lithium hydroxide in aqueous THF solution will yield the carboxylic

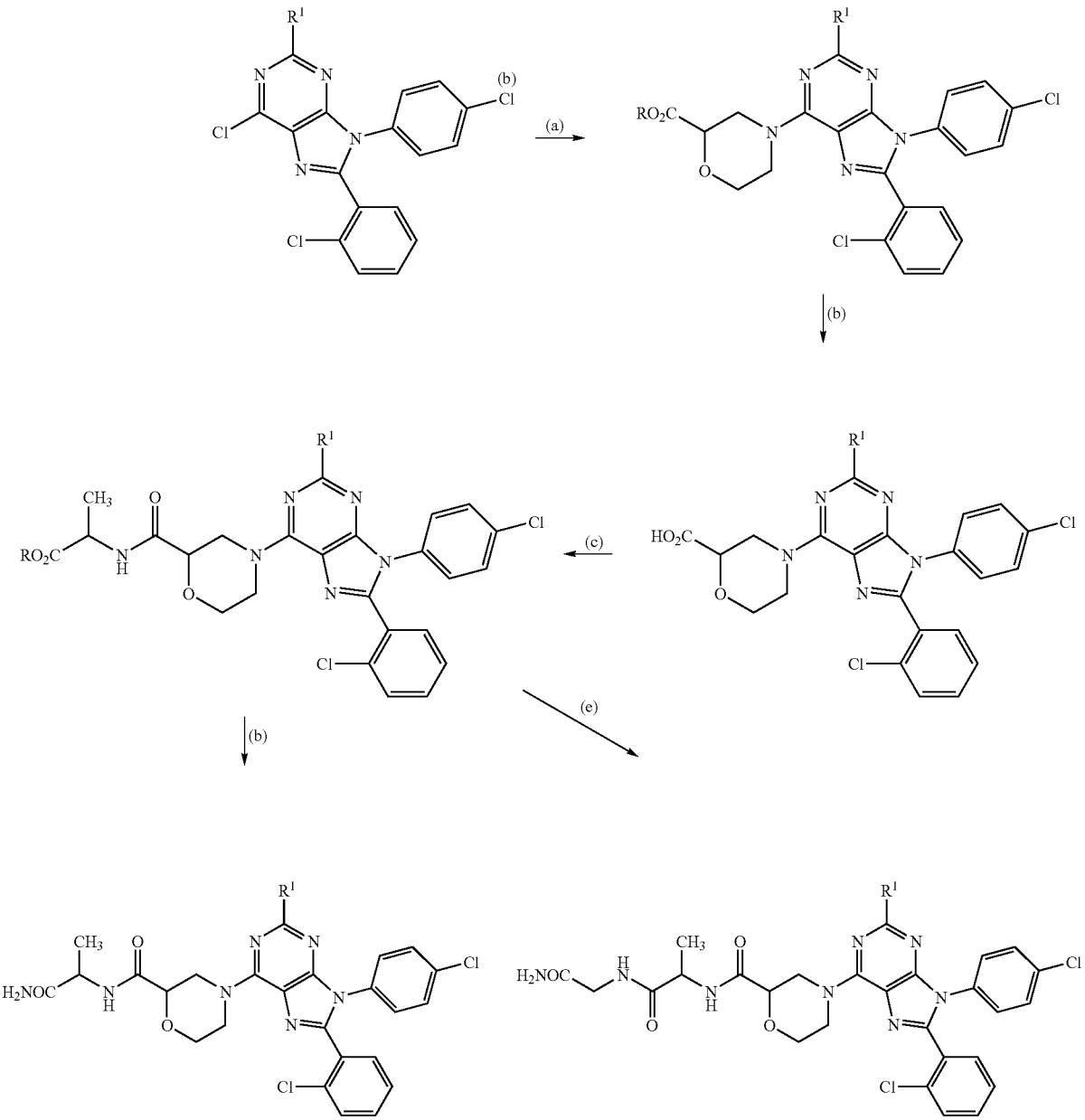

Scheme 6

Scheme 7 shows the synthesis of amino purine adducts that have amino acid pendants at another position of the amine heterocycle. The previously described chloropurine can be condensed with piperazine-1,3-dicarboxylic acid 1-t-butyl ester 3-ethyl ester (Chiu and Griffith, EP 1004583 A2) in a solvent such as ethanol, acetone, water and combinations thereof in the presence of an amine such as triethylamine to produce the aminopurine adduct (step a). Hydrolysis of the ester with lithium hydroxide in aqueous THF solution will acid (step d) which upon further treatment with TFA in methylene chloride can produce the amino acid (step e). Optionally, the t-Boc protected amino acid can be condensed with anhydrous ammonia in the presence of isobutylchloroformate (IBCF) and N-methylmorpholine in methylene chloride at 0° C. to room temperature to yield the carboxamide (step f) which upon treatment with TFA in methylene chloride can produce the unprotected amino-carboxamide (step g).

Scheme 7

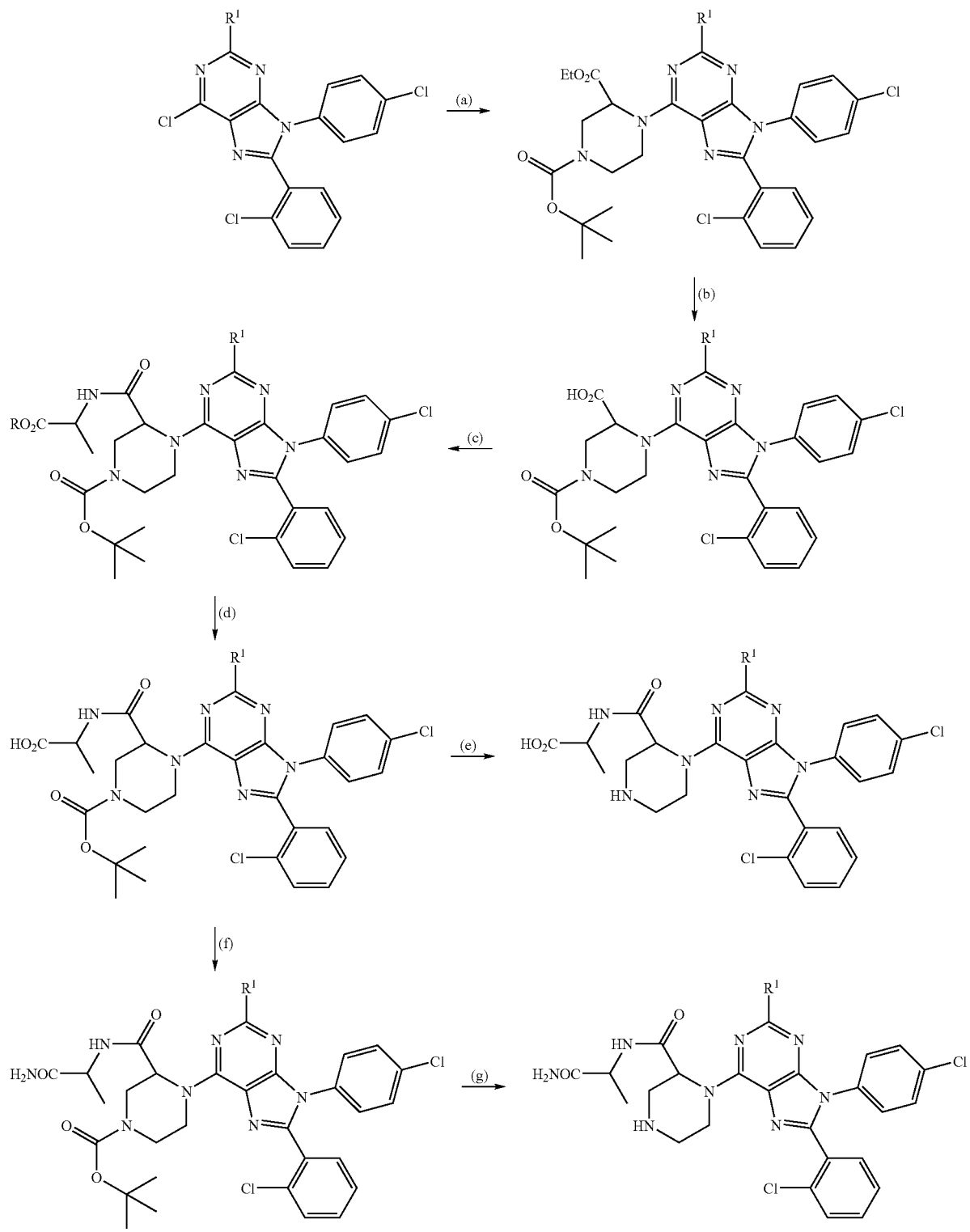

Scheme 8 shows the route to heterocyclic amine adducts with functionality on the N-atom of the heterocycle. The previously described chloropurine can be condensed with 1-t-BOC-piperazine (Sigma-Aldrich) to produce the carbamate (step a). Removal of the protecting group using TFA in methylene chloride (step b) and acylation of the amine with ethyl malonylchloride in a solvent such as methylene chloride in the presence of a base such as triethylamine should afford the ester (step c). Hydrolysis of the ester with lithium hydroxide in aqueous THF solution will yield the carboxylic acid (step d), which can be condensed with anhydrous ammonia in the presence of isobutylchloroformate (IBCF) and N-methylmorpholine in methylene chloride at 0° C. to room temperature to yield the carboxamide (step e). Alternatively, the carboxylic acid can be treated with amino acid esters such as that of glycine in the presence of isobutylchloroformate (IBCF) and N-methylmorpholine in methylene chloride at 0° C. to room temperature to yield the ester (step f). Hydrolysis with lithium hydroxide and amination with ammonia as described above can afford the caboxamide (step g).

Scheme 8

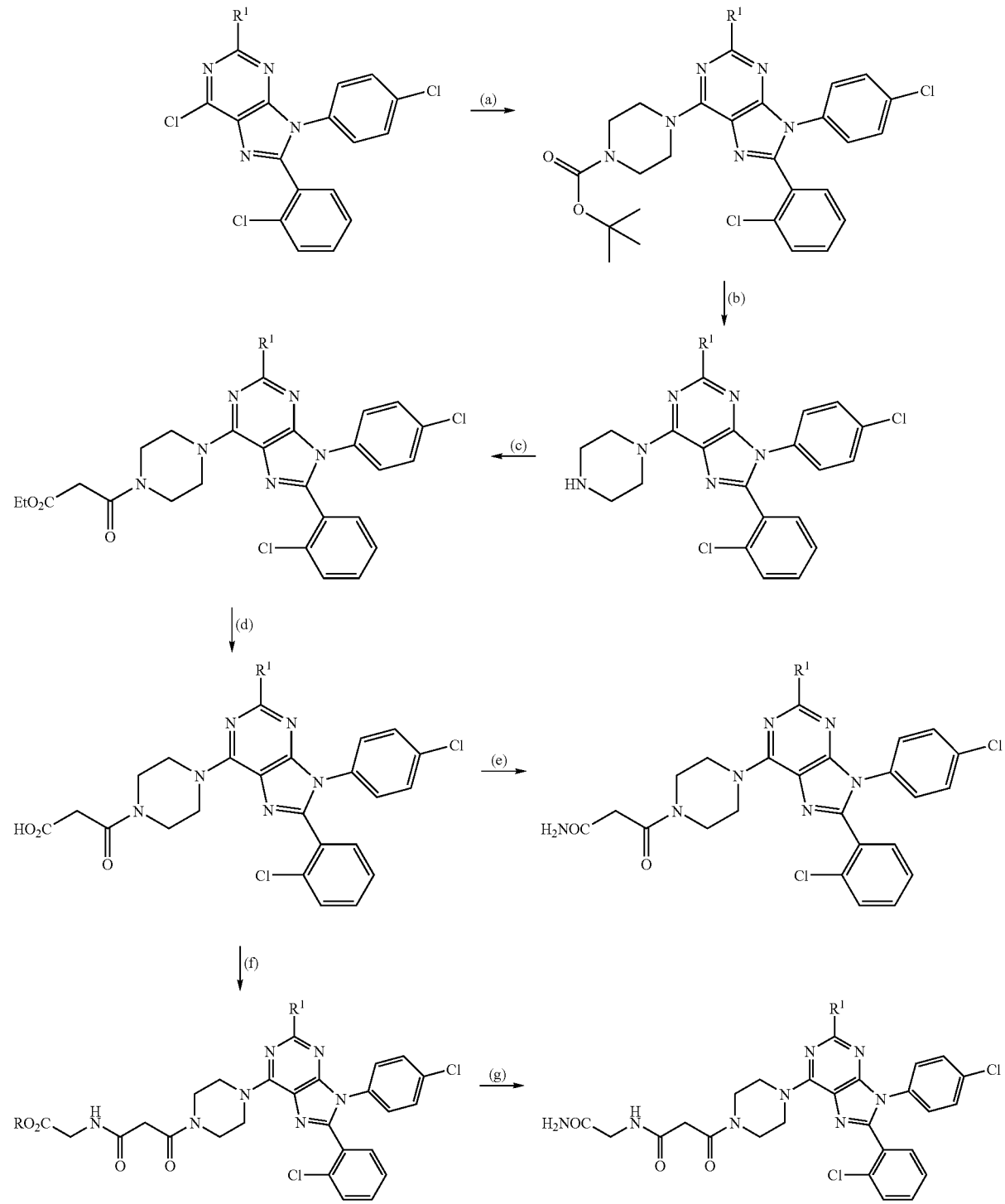

The sequence of reactions in Scheme 9 shows the preparation of analogs with functionality incorporated onto the N-ethyl group of the piperidine ring. Treatment of the forementioned chloro-purine with 4-piperidone in a solvent such as ethanol, acetone, water and combinations thereof in the presence of an amine such as triethylamine should produce the piperidone adduct (step a). Treatment of this ketone with an amine such as beta-alanine carboxamide in the presence of trimethylsilylcyanide and ytterbium (III) triflate in dichloromethane should afford the aminonitrile (step b). Hydration of the nitrile with sulfuric acid in dichloromethane should produce the aminocarboxamide (step c). Alternativley, N-benzyl-4-piperidone can be treated with an aminoester in the presence of trimethylsilylcyanide and ytterbium (III) triflate in dichloromethane to produce an amino-ester nitrile adduct that can be hydrated with sulfuric acid and catalytically de-benzylated over Pd/C in the presence of hydrogen to yield the amino-ester carboxamide. Condensation of this amine with chloropurine, as described above, can also afford the piperidine adduct (step d). Hyrolysis of the ester with lithium hydroxide in aqueous THF solution followed by coupling of the resultant carboxylic acid with ammonia in the presence of isobutylchloroformate should yield the di-carboxamide (step e).

Scheme 9

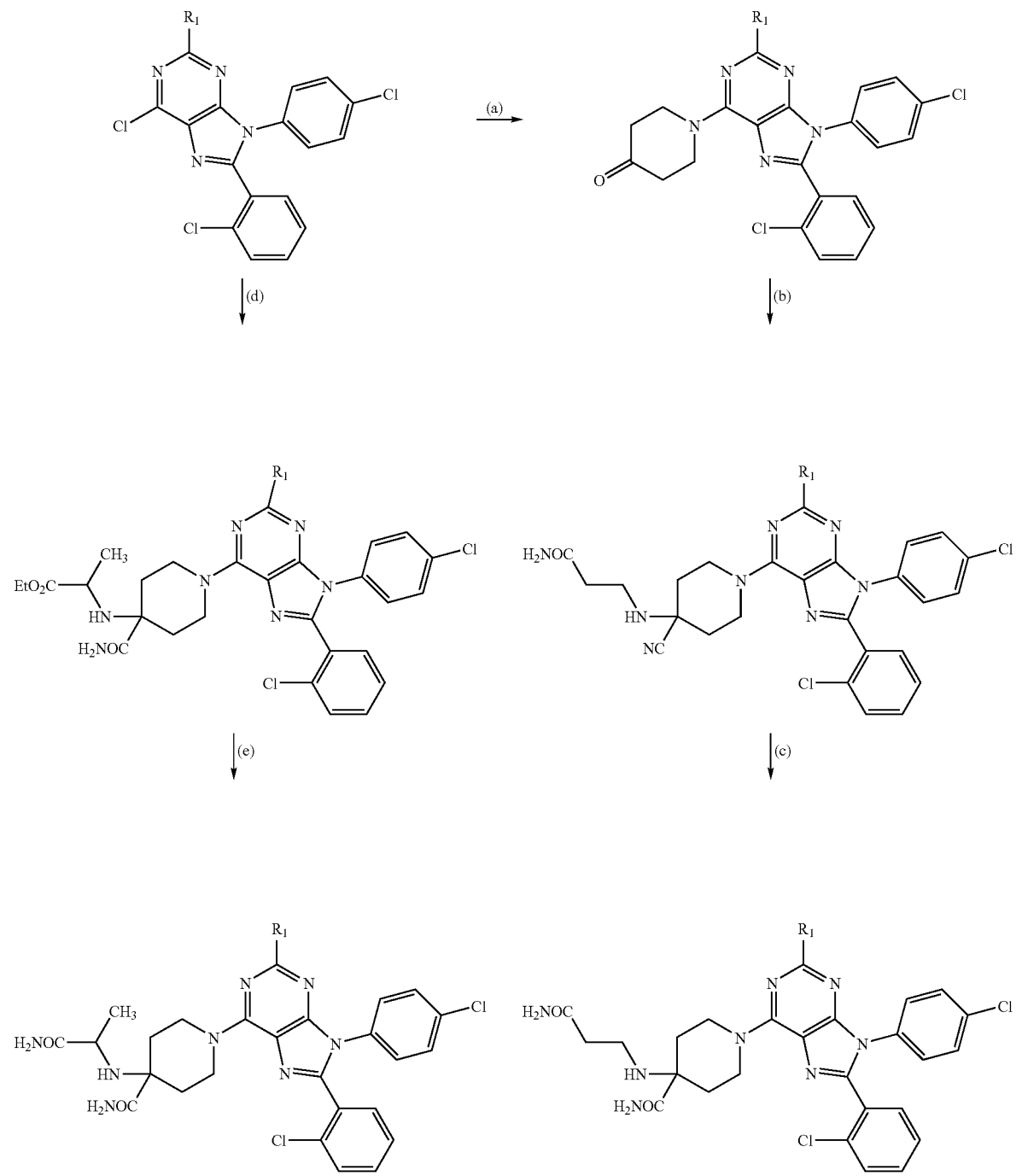

One stereoisomer of a compound of the present invention may be a more potent cannabinoid receptor antagonist than its counterpart(s). Thus, stereoisomers are included in the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of the present invention may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

Other features of the invention will become apparent in the course of the following descriptions of exemplary embodiments that are given for illustration of the invention and are not intended to be limiting thereof.

EXAMPLES

Compounds in Tables A-C have been made according to the designated synthetic route, characterized by $^1$H NMR, and tested for CB1 activity. All have been shown to be active CB1 antagonists/inverse agonists.

TABLE A

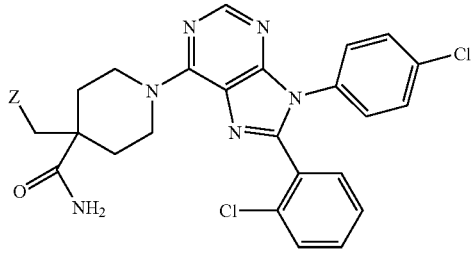

| Ex. # | Z | NMR (ppm) CDCl$_3$ or as indicated | Syn Route (Scheme) |
|---|---|---|---|
| 1 | CH$_2$CO$_2$CH$_2$CH$_3$ | 1.27 (3H, t) CH$_3$<br>1.28 (3H, t) CH$_3$<br>1.79 (2H, m) ring-CH$_2$<br>2.29 (2H, m) ring-CH$_2$<br>2.58 (2H, q) CH$_2$N<br>2.85 (2H, q) CH$_2$CO$_2$Et<br>3.90 (2H, bdr s) ring-CH$_2$<br>4.18 (2H, q) OCH$_2$<br>4.95 (2H brd s) ring-CH$_2$<br>5.41 (1H, bdr s) NH<br>7.21-7.51 (8H) aromatic H's<br>8.38 (1H, s) aromatic H | 9 |
| 2 | CH$_2$CONH$_2$ | 1.78 (2H, m) ring-CH$_2$<br>2.23 (2H, m) ring-CH$_2$<br>3.31 (2H, s) CH$_2$CONH$_2$<br>4.08 (2H, bdr s) ring-CH$_2$<br>4.77 (2H brd s) ring-CH$_2$<br>5.70 (1H, bdr s) NH<br>5.80 (1H, bdr s) NH<br>6.48 (1H, bdr s) NH<br>6.88 (1H, bdr s) NH<br>7.18-7.51 (8H) aromatic H's<br>8.37 (1H, s) aromatic H | 9 |
| 3 | CH$_2$SO$_2$NH$_2$ | 1.78 (2H, m) ring-CH$_2$<br>2.10 (2H, m) ring-CH$_2$<br>2.99 (2H, brd s) CH$_2$SO$_2$NH$_2$<br>3.32 (2H, brd s) NCH$_2$<br>3.82 (2H, bdr s) ring-CH$_2$<br>4.90 (2H brd s) ring-CH$_2$<br>5.74 (1H, bdr s) NH<br>6.74 (1H, bdr s) NH<br>7.06 (1H, bdr s) NH<br>7.16-7.50 (8H) aromatic H's<br>8.32 (1H, s) aromatic H | 9 |
| 4 | CH$_2$CH$_2$CH$_2$—CH(NH$_2$)CO$_2$CH$_3$ | CD$_3$OD<br>1.57 (4H, m) CH$_2$s<br>1.88 (4H, m) CH$_2$s<br>2.12 (2H, m) ring-CH$_2$<br>2.54 (2H, t) NCH$_2$<br>3.78 (3H, s) OCH$_3$<br>3.81 (1H, m) chain-CH<br>4.18 (2H, bdr s) ring-CH$_2$<br>4.69 (2H brd s) ring-CH$_2$<br>7.29-7.61 (8H) aromatic H's<br>8.23 (1H, s) aromatic H | 9 |

TABLE A-continued

| Ex. # | Z | NMR (ppm) CDCl₃ or as indicated | Syn Route (Scheme) |
|---|---|---|---|
| 5 | CH₂CH₂CH₂—CH(NH₂)CONH₂ | CD₃OD<br>1.55-1.87 (8H, m's) CH₂s<br>2.12 (2H, m) ring-CH₂<br>2.53 (2H, t) NCH₂<br>3.50 (1H, t) chain-CH<br>4.20 (2H, bdr s) ring-CH₂<br>4.69 (2H brd s) ring-CH₂<br>7.29-7.60 (8H) aromatic H's<br>8.22 (1H, s) aromatic H | 9 |
| 6 | CH₂CONHCH₃ | 1.82 (2H, m) ring-CH₂<br>2.12 (2H, m) ring-CH₂<br>2.41 (2H, t) CH₂CO<br>2.73 (3H, s) NCH₃<br>2.79 (2H, t) NCH₂<br>3.32 (2H, brd s) NCH₂<br>3.95 (2H, bdr s) ring-CH₂<br>7.29-7.61 (8H) aromatic H's<br>8.22 (1H, s) aromatic H | 9 |
| 7 | CH₂CH₂CONH₂ | 1.82 (4H, m) CH₂s<br>2.10 (2H, m) ring-CH₂<br>2.32 (2H, t) CH₂CO<br>2.55 (2H, t) NCH₂<br>4.10 (2H, bdr s) ring-CH₂<br>4.76 (2H, bdr s) ring-CH₂<br>7.28-7.6 1 (8H) aromatic H's<br>8.22 (1H, s) aromatic H | 9 |

TABLE B

| Ex. # | Z | NMR (ppm) CDCl₃ or as indicated | Syn Route (Scheme) |
|---|---|---|---|
| 1 | CH₂CO₂CH₃ | CD₃OD<br>1.15 (3H, t) CH₃<br>1.80 (2H, m) ring-CH₂<br>2.17 (2H, m) ring-CH₂<br>2.59 (2H, q) CH₂N<br>3.72 (3H, s) OCH₃<br>3.98 (2H, s) CH₂CO<br>4.25 (2H, bdr s) ring-CH₂<br>4.68 (2H, brd s) ring-CH₂<br>7.28-7.62 (8H) aromatic H's<br>8.23 (1H, s) aromatic H | 1 |
| 2 | CH₂CONH₂ | 1.16 (3H, t) CH₃<br>1.78 (2H, m) ring-CH₂<br>2.23 (2H, m) ring-CH₂<br>2.56 (2H, q) CH₂N<br>3.83 (2H, bdr s) ring-CH₂<br>3.95 (2H, d) CH₂CO | 1 |

TABLE B-continued

Structure: 9-(4-chlorophenyl)-8-(2-chlorophenyl)-6-[4-ethyl-4-(NH-Z-carbamoyl)piperidin-1-yl]-9H-purine

| Ex. # | Z | NMR (ppm) CDCl₃ or as indicated | Syn Route (Scheme) |
|---|---|---|---|
| | | 5.00 (H, brd s) ring-CH₂<br>5.50 (1H, m) NH<br>6.02 (1H, m) NH<br>7.19-7.50 (8H) aromatic H's<br>8.01 (1H, m) NH<br>8.38 (1H, s) aromatic H | |
| 3 | CHCH₃CO₂CH₃ | 1.17 (3H, t) CH₃<br>1.42 (3H, d) CH₃<br>1.77 (2H, m) ring-CH₂<br>2.25 (2H, m) ring-CH₂<br>2.60 (2H, q) CH₂N<br>3.75 (3H, s) OCH₃<br>4.04 (2H, bdr s) ring-CH₂<br>4.57 (1H, m) CHCO<br>4.83 (2H brd s) ring-CH₂<br>7.21-7.52 (8H) aromatic H's<br>7.87 (1H, d) NH<br>8.38 (1H, s) aromatic H | 1 |
| 4 | CHCH₃CONH₂ | 1.15 (3H, t) CH₃<br>1.40 (3H, d) CH₃<br>1.77 (2H, m) ring-CH₂<br>2.12 (2H, m) ring-CH₂<br>2.54 (2H, q) CH₂N<br>3.78 (2H, bdr s) ring-CH₂<br>4.45 (1H, m) CHCO<br>5.00 (2H, brd s) ring-CH₂<br>5.31 (1H, brd s) NH<br>6.20 (1H, brd s) NH<br>7.19-7.51 (8H) aromatic H's<br>7.83 (1H, d) NH<br>8.39 (1H, s) aromatic H | 1 |
| 5 | CH(CH₂OH)CO₂CH₃ | 1.18 (3H, t) CH₃<br>1.80 (2H, m) CH₂<br>2.25 (2H, m) ring-CH₂<br>2.62 (2H, q) CH₂N<br>3.78 (3H, s) OCH₃<br>3.95 (2H, bdr s) ring-CH₂<br>3.96 (2H, dq) O—CH₂<br>4.64 (1H, dt) CHCO<br>4.80 (2H, brd s) ring-CH₂<br>7.19-7.49 (8H) aromatic H's<br>8.30 (1H, d) NH<br>8.38 (1H, s) aromatic H | 1 |
| 6<br>6009 | CH(CH₂OH)CONH₂ | 1.16 (3H, t) CH₃<br>1.80 (2H, m) CH₂<br>2.20 (2H, m) ring-CH₂<br>2.56 (2H, q) CH₂N<br>3.65 (1H, dd) OCH<br>3.80 (2H, bdr s) ring-CH₂<br>4.17 (1H, dd) OCH<br>4.42 (1H, dt) CHCO<br>5.04 (2H, brd s) ring-CH₂<br>5.41 (1H, brd s) NH<br>6.72 (1H, brd s) NH<br>7.19-7.50 (8H) aromatic H's<br>8.38 (1H, s) aromatic H<br>8.39 (1H, brd s) NH | 1 |
| 7 | CH(CHCH₃OH)CO₂CH₃ | 1.18 (3H, t) CH₃<br>1.23 (3H, d) CH₃<br>1.80 (2H, m) CH₂<br>2.28 (2H, m) ring-CH₂<br>2.62 (2H, q) CH₂N<br>3.77 (3H, s) OCH₃<br>3.95 (2H, bdr s) ring-CH₂ | 1 |

TABLE B-continued

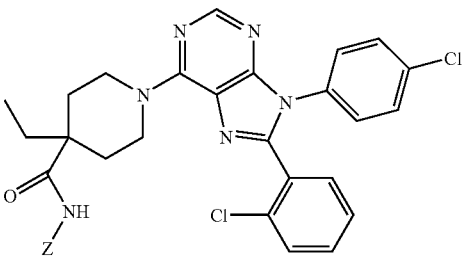

| Ex. # | Z | NMR (ppm) CDCl$_3$ or as indicated | Syn Route (Scheme) |
|---|---|---|---|
|  |  | 4.40 (2H, dq) O—CH<br>4.56 (1H, dt) CHCO<br>4.92 (2H, brd s) ring-CH$_2$<br>7.19-7.50 (8H) aromatic H's<br>8.13 (1H, d) NH<br>8.39 (1H, s) aromatic H |  |
| 8 | CH(CHCH$_3$OH)CONH$_2$ | 1.16-1.19 (6H) CH$_3$'s<br>1.80 (2H, m) CH$_2$<br>2.25 (2H, m) ring-CH$_2$<br>2.56 (2H, q) CH$_2$N<br>3.80 (2H, bdr s) ring-CH$_2$<br>4.27 (1H, d) O—CH<br>4.42 (1H, dq) CHCO<br>5.05 (2H, brd s) ring-CH$_2$<br>5.39 (1H, brd s) NH<br>6.70 (1H, brd s) NH<br>7.19-7.49 (8H) aromatic H's<br>8.30 (1H, d) NH<br>8.39 (1H, s) aromatic H | 1 |
| 9 | CH$_2$CHOHCH$_2$CO$_2$CH$_3$ | 1.14 (3H, t) CH$_3$<br>1.75 (2H, m) CH$_2$<br>2.25 (2H, m) ring-CH$_2$<br>2.49 (2H, dd) CH$_2$N<br>2.55 (2H, q) CH$_2$N<br>3.25 (1H, m) CH$_2$CO<br>3.50 (1H, m) CH$_2$CO<br>3.72 (3H, s) OCH$_3$<br>3.87 (2H, bdr s) ring-CH$_2$<br>4.12 (1H, M) O—CH<br>4.98 (2H, brd s) ring-CH$_2$<br>7.19-7.50 (8H) aromatic H's<br>7.83 (1H, m) NH<br>8.40 (1H, s) aromatic H | 1 |
| 10 | CH$_2$CHOHCH$_2$CONH$_2$ | (CD$_3$OD)<br>1.17 (3H, t) CH$_3$<br>1.81 (2H, m) CH$_2$<br>2.20 (2H, m) ring-CH$_2$<br>2.40 (2H, dq) NCH$_2$<br>2.60 (2H, m) NCH$_2$<br>~3.3 (2H) CH$_2$CO<br>4.15 (2H, bdr s) ring-CH$_2$<br>4.10 (1H, m) O—CH<br>4.82 (2H, brd s) ring-CH$_2$<br>7.29-7.6 1 (8H) aromatic H's<br>8.24 (1H, s) aromatic H | 1 |
| 11 | CH$_2$CH$_2$CHOHCO$_2$CH$_3$ | 1.17 (3H, brd s) CH$_3$<br>1.80 (2H, m) CH$_2$<br>2.03 (2H, brd s) CH$_2$<br>2.27 (2H, m) ring-CH$_2$<br>2.58 (2H, brd s) CH$_2$N<br>3.79 (3H, s) OCH$_3$<br>3.83 (2H, bdr s) ring-CH$_2$<br>4.22 (1H, M) O—CH<br>4.87 (2H, brd s) ring-CH$_2$<br>7.19-7.49 (8H) aromatic H's<br>7.80 (1H, m) NH<br>8.38 (1H, s) aromatic H | 1 |
| 12 | CH$_2$CH$_2$CHOHCONH$_2$ | (CD$_3$OD)<br>1.15 (3H, t) CH$_3$<br>1.79 (2H, m) CH$_2$<br>2.00 (2H, brd s) CH$_2$<br>2.16 (2H, m) ring-CH$_2$<br>2.53 (2H, q) CH$_2$N<br>4.02 (1H) CHCO | 1 |

TABLE B-continued

[Structure: purine core with 9-(4-chlorophenyl), 8-(2-chlorophenyl), and 6-(4-ethyl-4-carboxamido-piperidinyl) substituents; amide is C(=O)NH-Z]

| Ex. # | Z | NMR (ppm) CDCl₃ or as indicated | Syn Route (Scheme) |
|---|---|---|---|
| 13 | CH[CH(CH₃)₂]CO₂CH₃ | 4.17 (2H, bdr s) ring-CH₂<br>4.68 (2H, brd s) ring-CH₂<br>7.29-7.62 (8H) aromatic H's<br>8.23 (1H, s) aromatic H<br>0.93 (6H, dd) CH₃'s<br>1.17 (3H, t) CH₃<br>1.79 (2H, m) CH₂<br>2.25 (2H, m) ring-CH₂<br>2.30 (1H, m) CH<br>2.60 (2H, q) CH₂N<br>3.74 (3H, s) OCH₃<br>3.93 (2H, brd s) ring-CH₂<br>4.50 (1H, d) CHCO<br>4.90 (2H brd s) ring-CH₂<br>7.19-7.51 (8H) aromatic H's<br>7.97 (1H, d) NH<br>8.40 (1H, s) aromatic H | 1 |
| 14 | CH[CH(CH₃)₂]CONH₂ | 0.98 (6H, dd) CH₃'s<br>1.16 (3H, t) CH₃<br>1.80 (2H, m) CH₂<br>2.20 (3H, m) CH, CH₂<br>2.55 (2H, m) CH₂N<br>3.87 (2H, brd s) ring-CH₂<br>4.22 (1H, m) CHCO<br>5.00 (2H brd s) ring-CH₂<br>5.45 (1H, brd s) NH<br>5.98 (1H, brd s) NH<br>7.19-7.51 (8H) aromatic H's<br>8.03 (1H, brd s) NH<br>8.38 (1H, s) aromatic H | 1 |
| 15 | CHCH₂[CH(CH₃)₂]CO₂CH₃ | 0.95 (6H, d) CH₃'s<br>1.16 (3H, t) CH₃<br>1.78 (2H, m) ring-CH₂<br>2.18 (2H, m) ring-CH₂<br>2.60 (2H, q) CH₂N<br>3.73 (3H, s) OCH₃<br>4.00 (2H, brd s) ring-CH₂<br>4.57 (1H, d) CHCO<br>4.90 (2H brd s) ring-CH₂<br>7.19-7.51 (8H) aromatic H's<br>7.75 (1H, d)NH<br>8.38 (1H, s) aromatic H | 1 |
| 16 | CHCH₂[CH(CH₃)₂]CONH₂ | 0.95 (6H, d) CH₃'s<br>1.14 (3H, t) CH₃<br>1.78 (2H, m) ring-CH₂<br>2.23 (2H, m) ring-CH₂<br>2.30 (1H, m) CH<br>2.54 (2H, q) CH₂N<br>3.88 (2H, brd s) ring-CH₂<br>4.43 (1H, d) CHCO<br>4.95 (2H brd s) ring-CH₂<br>5.35 (1H, brd s) NH<br>6.21 (1H, brd s) NH<br>7.19-7.51 (8H) aromatic H's<br>7.78 (1H, d) NH<br>8.438 (1H, s) aromatic H | 1 |
| 17 | CH[C(CH₃)₃]CO₂CH₃ | 0.99 (9H, s) CH₃'s<br>1.18 (3H, t) CH₃<br>1.78 (2H, m) CH₂<br>2.25 (2H, m) ring-CH₂<br>2.60 (2H, q) CH₂N<br>3.72 (3H, s) OCH₃<br>3.90 (2H, brd s) ring-CH₂<br>4.36 (1H, d) CHCO | 1 |

TABLE B-continued

| Ex. # | Z | NMR (ppm) CDCl₃ or as indicated | Syn Route (Scheme) |
|---|---|---|---|
| | | 4.93 (2H brd s) ring-CH₂ 7.19-7.51 (8H) aromatic H's 8.10 (1H, d) NH 8.38 (1H, s) aromatic H | |
| 18 | CH[CH₂(C₆H₅)]CO₂CH₃ | 0.99 (3H, t) CH₃ 1.59 (1H, brd m) ring H 1.71 (1H, brd m) ring H 2.10 (1H, brd m) ring H 2.23 (1H, brd m) ring H 2.41 (2H, brd d) CH₂N 3.05 (1H, dd) CH-phenyl 3.21 (1H, m) CH-phenyl 3.75 (3H, s) OCH₃ 3.90 (2H, brd s) ring-CH₂ 4.80 (2H brd s) ring-CH₂ 4.85 (1H, m) CHCO 7.18-7.50 (8H) aromatic H's 8.10 (1H, m) NH 8.37 (1H, s) aromatic H | 1 |
| 19 | CH[CH₂(C₆H₅)]CONH₂ | CD₃OD 1.01 (3H, t) CH₃ 1.55 (3H, brd m) ring H's 1.95 (1H, brd m) ring H 2.09 (1H, brd m) ring H 2.23 (1H, brd m) ring H 2.35 (1H, brd m) CH₂N 2.92 (1H, dd) CH-phenyl 3.19 (1H, m) CH-phenyl 4.12 (2H, brd s) ring-CH₂ 4.75 (1H, m) CHCO 7.18-7.48 (13H) aromatic H's 8.20 (1H, s) aromatic H | 1 |
| 20 | C(CH₃)₂CO₂CH₃ | 1.15 (3H, t) CH₃ 1.54 (6H, s) CH₃'s 1.73 (2H, m) CH₂ 2.23 (2H, m) ring-CH₂ 2.59 (2H, q) CH₂N 3.73 (3H, s) OCH₃ 4.03 (2H, brd s) ring-CH₂ 4.81 (2H brd s) ring-CH₂ 7.19-7.51 (8H) aromatic H's 7.86 (1H, d) NH 8.37 (1H, s) aromatic H | 1 |
| 21 | cyclobutyl-CO₂CH₃ | 1.15 (3H, t) CH₃ 1.73 (2H, m) CH₂ 2.05 (2H, m) ring-CH₂ 2.30 (4H, m) ring-CH₂'s 2.62 (4H, m) CH₂N, ring-CH₂ 3.76 (3H, s) OCH₃ 4.10 (2H, brd s) ring-CH₂ 4.78 (2H brd s) ring-CH₂ 7.19-7.52 (8H) aromatic H's 7.89 (1H, d) NH 8.37 (1H, s) aromatic H | 1 |

TABLE B-continued

| Ex. # | Z | NMR (ppm) CDCl₃ or as indicated | Syn Route (Scheme) |
|---|---|---|---|
| 22 6034 | CONH₂ (cyclobutyl) | 1.16 (3H, t) CH₃<br>1.75 (2H, m) CH₂<br>1.97 (2H, m) ring-CH₂<br>2.30 (4H, m) ring-CH₂'s<br>2.57 (2H, m) CH₂N<br>2.77 (2H, m) ring-CH₂<br>3.88 (2H, brd s) ring-CH₂<br>4.93 (2H brd s) ring-CH₂<br>5.20 (1H, brd s) NH<br>7.14 (1H, brd s) NH<br>7.19-7.49 (8H) aromatic H's<br>7.97 (1H, d) NH<br>8.38 (1H, s) aromatic H | 1 |

TABLE C

| Ex. # | X | NMR (ppm) CDCl₃ or as indicated | Syn Route (Scheme) |
|---|---|---|---|
| 1 | 4-OCH₂CO₂CH₂CH₃ | 1.14 (3H, t) CH₃<br>1.28 (3H, t) CH₃<br>1.80 (2H, m) ring-CH₂<br>2.25 (2H, m) ring-CH₂<br>2.60 (2H, q) CH₂N<br>3.96 (2H, bdr s) ring-CH₂<br>4.26 (2H, q) OCH₂<br>4.59 (2H, s) OCH₂<br>4.90 (2H brd s) ring-CH₂<br>5.40 (1H, bdr s) NH<br>6.88-7.51 (8H) aromatic H's<br>8.38 (1H, s) aromatic H | 2 |
| 2 | 4-OCH₂CONH₂ | 1.14 (3H, t) CH₃<br>1.79 (2H, m) ring-CH₂<br>2.22 (2H, m) ring-CH₂<br>2.60 (2H, q) CH₂N<br>3.95 (2H, bdr s) ring-CH₂<br>4.47 (2H, s) OCH₂<br>4.90 (2H brd s) rig-CH₂<br>5.52 (1H, bdr s) NH<br>5.85 (1H, bdr s) NH<br>6.51 (1H, bdr s) NH<br>6.89-7.49 (8H) aromatic H's<br>8.40 (1H, s) aromatic H | 2 |
| 3 | 4-OCH₂CO₂H | (CD₃SOCD₃)<br>1.16 (3H, t) CH₃<br>1.91 (2H, brd s) ring-CH₂<br>2.20 (2H, brd s) ring-CH₂<br>2.59 (2H, brd s) CH₂N<br>6.88-7.70 (8H) aromatic H's<br>8.03 (1H, brd s) NH<br>8.23 (1H, s) aromatic H | |
| 4 | 4-NHCH₂CO₂CH₂CH₃ | 1.14 (3H, t) CH₃<br>1.28 (3H, t) CH₃<br>1.80 (2H, m) ring-CH₂<br>2.25 (2H, m) ring-CH₂<br>2.59 (2H, q) CH₂N<br>3.85 (2H, d) NHCH₂CO<br>3.96 (2H, bdr s) ring-CH₂<br>4.25 (2H, s) OCH₂<br>4.43 (1H, t) NH<br>4.90 (2H brd s) ring-CH₂<br>5.42 (1H, bdr s) NH<br>6.53-7.48 (8H) aromatic H's<br>7.17 (1H, brd s) NH<br>8.38 (1H, s) aromatic H | 4 |
| 5 | 4-NHCH₂CONH₂ | (CD₃OD)<br>1.14 (3H, t) CH₃<br>1.77 (2H, m) ring-CH₂<br>2.13 (2H, m) ring-CH₂<br>2.55 (2H, q) CH₂N<br>3.72 (2H, s) NHCH₂CO<br>4.25 (2H, bdr s) ring-CH₂<br>4.57 (2H brd s) rig-CH₂<br>6.56-7.51 (8H) aromatic H's<br>8.19 (1H, s) aromatic H | 4 |

Tables 1-8 show representative examples of the compounds of the present invention. Each example in each table represents an individual species of the present invention.

TABLE 1

| Ex. # | A¹ | A² | R¹ | Q | R |
|---|---|---|---|---|---|
| 1 | Cl | H | H | H | OMe |
| 2 | Cl | H | H | H | OH |
| 3 | Cl | H | H | H | NH₂ |
| 4 | Cl | H | H | H | NHCH₂CO₂CH₃ |
| 5 | Cl | H | H | H | NHCH₂CO₂H |
| 6 | Cl | H | H | H | NHCH₂CONH₂ |
| 7 | Cl | H | CH₃ | H | OMe |
| 8 | Cl | H | CH₃ | H | OH |
| 9 | Cl | H | CH₃ | H | NH₂ |
| 10 | Cl | H | CH₃ | H | NHCH₂CO₂CH₃ |
| 11 | Cl | H | CH₃ | H | NHCH₂CO₂H |
| 12 | Cl | H | CH₃ | H | NHCH₂CONH₂ |
| 13 | Cl | H | H | CH₃ | OMe |
| 14 | Cl | H | H | CH₃ | OH |
| 15 | Cl | H | H | CH₃ | NH₂ |
| 16 | Cl | H | H | CH₃ | NHCH₂CO₂CH₃ |
| 17 | Cl | H | H | CH₃ | NHCH₂CO₂H |
| 18 | Cl | H | H | CH₃ | NHCH₂CONH₂ |
| 19 | Cl | H | CH₃ | CH₃ | OMe |
| 20 | Cl | H | CH₃ | CH₃ | OH |
| 21 | Cl | H | CH₃ | CH₃ | NH₂ |
| 22 | Cl | H | CH₃ | CH₃ | NHCH₂CO₂CH₃ |
| 23 | Cl | H | CH₃ | CH₃ | NHCH₂CO₂H |
| 24 | Cl | H | CH₃ | CH₃ | NHCH₂CONH₂ |
| 25 | Cl | H | H | CH₂OH | OMe |
| 26 | Cl | H | H | CH₂OH | OH |
| 27 | Cl | H | H | CH₂OH | NH₂ |
| 28 | Cl | H | H | CH₂OH | NHCH₂CO₂CH₃ |
| 29 | Cl | H | H | CH₂OH | NHCH₂CO₂H |
| 30 | Cl | H | H | CH₂OH | NHCH₂CONH₂ |
| 31 | Cl | H | CH₃ | CH₂OH | OMe |
| 32 | Cl | H | CH₃ | CH₂OH | OH |
| 33 | Cl | H | CH₃ | CH₂OH | NH₂ |
| 34 | Cl | H | CH₃ | CH₂OH | NHCH₂CO₂CH₃ |
| 35 | Cl | H | CH₃ | CH₂OH | NHCH₂CO₂H |
| 36 | Cl | H | CH₃ | CH₂OH | NHCH₂CONH₂ |
| 37 | F | Cl | H | H | OMe |
| 38 | F | Cl | H | H | OH |
| 39 | F | Cl | H | H | NH₂ |
| 40 | F | Cl | H | H | NHCH₂CO₂CH₃ |
| 41 | F | Cl | H | H | NHCH₂CO₂H |
| 42 | F | Cl | H | H | NHCH₂CONH₂ |
| 43 | F | Cl | CH₃ | H | OMe |
| 44 | F | Cl | CH₃ | H | OH |
| 45 | F | Cl | CH₃ | H | NH₂ |
| 46 | F | Cl | CH₃ | H | NHCH₂CO₂CH₃ |
| 47 | F | Cl | CH₃ | H | NHCH₂CO₂H |
| 48 | F | Cl | CH₃ | H | NHCH₂CONH₂ |
| 49 | F | Cl | H | CH₃ | OMe |
| 50 | F | Cl | H | CH₃ | OH |
| 51 | F | Cl | H | CH₃ | NH₂ |
| 52 | F | Cl | H | CH₃ | NHCH₂CO₂CH₃ |
| 53 | F | Cl | H | CH₃ | NHCH₂CO₂H |
| 54 | F | Cl | H | CH₃ | NHCH₂CONH₂ |
| 55 | F | Cl | CH₃ | CH₃ | OMe |
| 56 | F | Cl | CH₃ | CH₃ | OH |
| 57 | F | Cl | CH₃ | CH₃ | NH₂ |
| 58 | F | Cl | CH₃ | CH₃ | NHCH₂CO₂CH₃ |
| 59 | F | Cl | CH₃ | CH₃ | NHCH₂CO₂H |
| 60 | F | Cl | CH₃ | CH₃ | NHCH₂CONH₂ |
| 61 | F | Cl | H | CH₂OH | OMe |
| 62 | F | Cl | H | CH₂OH | OH |
| 63 | F | Cl | H | CH₂OH | NH₂ |
| 64 | F | Cl | H | CH₂OH | NHCH₂CO₂CH₃ |
| 65 | F | Cl | H | CH₂OH | NHCH₂CO₂H |
| 66 | F | Cl | H | CH₂OH | NHCH₂CONH₂ |
| 67 | F | Cl | CH₃ | CH₂OH | OMe |
| 68 | F | Cl | CH₃ | CH₂OH | OH |
| 69 | F | Cl | CH₃ | CH₂OH | NH₂ |
| 70 | F | Cl | CH₃ | CH₂OH | NHCH₂CO₂CH₃ |
| 71 | F | Cl | CH₃ | CH₂OH | NHCH₂CO₂H |
| 72 | F | Cl | CH₃ | CH₂OH | NHCH₂CONH₂ |

TABLE 2

| Ex. # | A¹ | A² | R¹ | B¹ |
|---|---|---|---|---|
| 1 | Cl | H | H | OCH₂CO₂Et |
| 2 | Cl | H | H | OCH₂CO₂H |
| 3 | Cl | H | H | OCH₂CONH₂ |
| 4 | Cl | H | H | OCH₂CH=CHCO₂Et |
| 5 | Cl | H | H | OCH₂CH=CHCO₂H |
| 6 | Cl | H | H | OCH₂CH=CHCONH₂ |
| 7 | Cl | H | H | NHCOCH₂CO₂Et |
| 8 | Cl | H | H | NHCOCH₂CO₂H |
| 9 | Cl | H | H | NHCOCH₂CONH₂ |
| 10 | Cl | H | CH₃ | OCH₂CO₂Et |
| 11 | Cl | H | CH₃ | OCH₂CO₂H |
| 12 | Cl | H | CH₃ | OCH₂CONH₂ |
| 13 | Cl | H | CH₃ | OCH₂CH=CHCO₂Et |
| 14 | Cl | H | CH₃ | OCH₂CH=CHCO₂H |
| 15 | Cl | H | CH₃ | OCH₂CH=CHCONH₂ |
| 16 | Cl | H | CH₃ | NHCOCH₂CO₂Et |

TABLE 2-continued

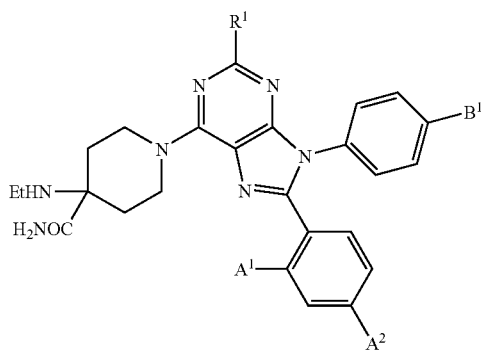

| Ex. # | A¹ | A² | R¹ | B¹ |
|---|---|---|---|---|
| 17 | Cl | H | CH₃ | NHCOCH₂CO₂H |
| 18 | Cl | H | CH₃ | NHCOCH₂CONH₂ |
| 19 | F | Cl | H | OCH₂CO₂Et |
| 20 | F | Cl | H | OCH₂CO₂H |
| 21 | F | Cl | H | OCH₂CONH₂ |
| 22 | F | Cl | H | OCH₂CH=CHCO₂Et |
| 23 | F | Cl | H | OCH₂CH=CHCO₂H |
| 24 | F | Cl | H | OCH₂CH=CHCONH₂ |
| 25 | F | Cl | H | NHCOCH₂CO₂Et |
| 26 | F | Cl | H | NHCOCH₂CO₂H |
| 27 | F | Cl | H | NHCOCH₂CONH₂ |
| 28 | F | Cl | CH₃ | OCH₂CO₂Et |
| 29 | F | Cl | CH₃ | OCH₂CO₂H |
| 30 | F | Cl | CH₃ | OCH₂CONH₂ |
| 31 | F | Cl | CH₃ | OCH₂CH=CHCO₂Et |
| 32 | F | Cl | CH₃ | OCH₂CH=CHCO₂H |
| 33 | F | Cl | CH₃ | OCH₂CH=CHCONH₂ |
| 34 | F | Cl | CH₃ | NHCOCH₂CO₂Et |
| 35 | F | Cl | CH₃ | NHCOCH₂CO₂H |
| 36 | F | Cl | CH₃ | NHCOCH₂CONH₂ |

TABLE 3

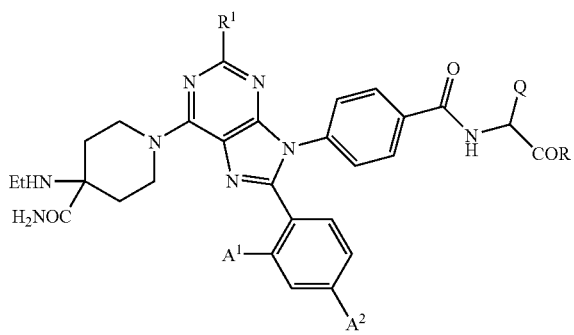

| Ex. # | A¹ | A² | R¹ | Q | R |
|---|---|---|---|---|---|
| 1 | Cl | H | H | H | OMe |
| 2 | Cl | H | H | H | OH |
| 3 | Cl | H | H | H | NH₂ |
| 4 | Cl | H | H | H | NHCH₂CO₂CH₃ |
| 5 | Cl | H | H | H | NHCH₂CO₂H |
| 6 | Cl | H | H | H | NHCH₂CONH₂ |
| 7 | Cl | H | CH₃ | H | OMe |
| 8 | Cl | H | CH₃ | H | OH |
| 9 | Cl | H | CH₃ | H | NH₂ |
| 10 | Cl | H | CH₃ | H | NHCH₂CO₂CH₃ |
| 11 | Cl | H | CH₃ | H | NHCH₂CO₂H |
| 12 | Cl | H | CH₃ | H | NHCH₂CONH₂ |
| 13 | Cl | H | H | CH₃ | OMe |
| 14 | Cl | H | H | CH₃ | OH |
| 15 | Cl | H | H | CH₃ | NH₂ |
| 16 | Cl | H | H | CH₃ | NHCH₂CO₂CH₃ |
| 17 | Cl | H | H | CH₃ | NHCH₂CO₂H |

TABLE 3-continued

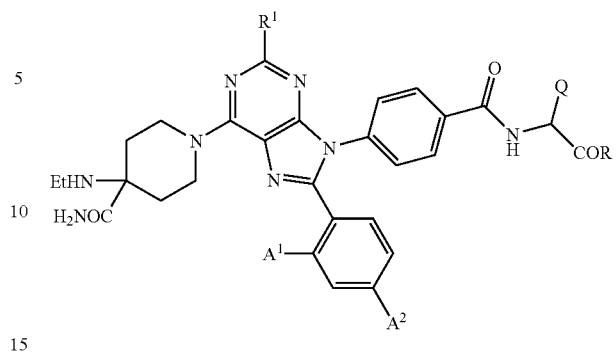

| Ex. # | A¹ | A² | R¹ | Q | R |
|---|---|---|---|---|---|
| 18 | Cl | H | H | CH₃ | NHCH₂CONH₂ |
| 19 | Cl | H | CH₃ | CH₃ | OMe |
| 20 | Cl | H | CH₃ | CH₃ | OH |
| 21 | Cl | H | CH₃ | CH₃ | NH₂ |
| 22 | Cl | H | CH₃ | CH₃ | NHCH₂CO₂CH₃ |
| 23 | Cl | H | CH₃ | CH₃ | NHCH₂CO₂H |
| 24 | Cl | H | CH₃ | CH₃ | NHCH₂CONH₂ |
| 25 | Cl | H | H | CH₂OH | OMe |
| 26 | Cl | H | H | CH₂OH | OH |
| 27 | Cl | H | H | CH₂OH | NH₂ |
| 28 | Cl | H | H | CH₂OH | NHCH₂CO₂CH₃ |
| 29 | Cl | H | H | CH₂OH | NHCH₂CO₂H |
| 30 | Cl | H | H | CH₂OH | NHCH₂CONH₂ |
| 31 | Cl | H | CH₃ | CH₂OH | OMe |
| 32 | Cl | H | CH₃ | CH₂OH | OH |
| 33 | Cl | H | CH₃ | CH₂OH | NH₂ |
| 34 | Cl | H | CH₃ | CH₂OH | NHCH₂CO₂CH₃ |
| 35 | Cl | H | CH₃ | CH₂OH | NHCH₂CO₂H |
| 36 | Cl | H | CH₃ | CH₂OH | NHCH₂CONH₂ |

TABLE 4

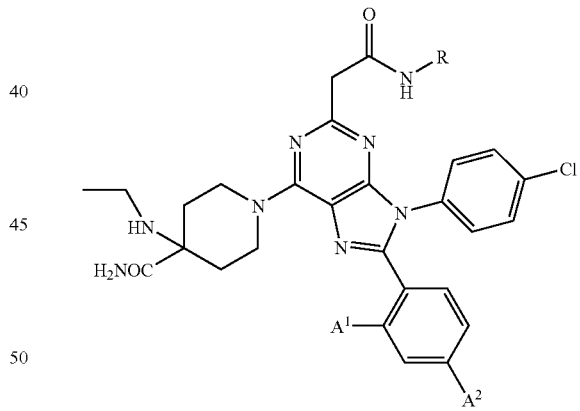

| Ex. # | A¹ | A² | R |
|---|---|---|---|
| 1 | Cl | H | H |
| 2 | Cl | H | CH₂CO₂Me |
| 3 | Cl | H | CH₂CO₂H |
| 4 | Cl | H | CH₂CONH₂ |
| 5 | Cl | H | CHCH₃CO₂Me |
| 6 | Cl | H | CHCH₃CO₂H |
| 7 | Cl | H | CHCH₃CONH₂ |
| 8 | Cl | H | CHCH₂OHCO₂Me |
| 9 | Cl | H | CHCH₂OHCO₂H |
| 10 | Cl | H | CHCH₂OHCONH₂ |
| 11 | F | Cl | H |
| 12 | F | Cl | CH₂CO₂Me |
| 13 | F | Cl | CH₂CO₂H |
| 14 | F | Cl | CH₂CONH₂ |
| 15 | F | Cl | CHCH₃CO₂Me |

TABLE 4-continued

[Structure: purine core with acetamide group at 2-position (NHR), ethylamino-piperidine-carboxamide at 6-position, 4-chlorophenyl at 9-position, and A¹/A² substituted phenyl at 8-position]

| Ex. # | A¹ | A² | R |
|---|---|---|---|
| 16 | F | Cl | CHCH₃CO₂H |
| 17 | F | Cl | CHCH₃CONH₂ |
| 18 | F | Cl | CHCH₂OHCO₂Me |
| 19 | F | Cl | CHCH₂OHCO₂H |
| 20 | F | Cl | CHCH₂OHCONH₂ |

TABLE 5

[Structure: purine core with (CH₂)ₙR at 2-position, ethylamino-piperidine-carboxamide at 6-position, 4-chlorophenyl at 9-position, and A¹/A² substituted phenyl at 8-position]

| Ex. # | n | A¹ | A² | R |
|---|---|---|---|---|
| 1 | 0 | Cl | H | NH₂ |
| 2 | 0 | Cl | H | NH(CH₂)₃CH(NH₂)CO₂Et |
| 3 | 0 | Cl | H | NH(CH₂)₃CH(NH₂)CO₂H |
| 4 | 0 | Cl | H | NH(CH₂)₃CH(NH₂)CONH₂ |
| 5 | 0 | Cl | H | NHCOCH₂CO₂Et |
| 6 | 0 | Cl | H | NHCOCH₂CO₂H |
| 7 | 0 | Cl | H | NHCOCH₂CONH₂ |
| 8 | 0 | Cl | H | NHCH₂CO₂Et |
| 9 | 0 | Cl | H | NHCH₂CO₂H |
| 10 | 0 | Cl | H | NHCH₂CONH₂ |
| 11 | 1 | Cl | H | NHCOCH₂CO₂Et |
| 12 | 1 | Cl | H | NHCOCH₂CO₂H |
| 13 | 1 | Cl | H | NHCOCH₂CONH₂ |
| 14 | 1 | Cl | H | NHCH₂CO₂Et |
| 15 | 1 | Cl | H | NHCH₂CO₂H |
| 16 | 1 | Cl | H | NHCH₂CONH₂ |
| 17 | 0 | F | Cl | NH(CH₂)₃CH(NH₂)CO₂Et |
| 18 | 0 | F | Cl | NH(CH₂)₃CH(NH₂)CO₂H |
| 19 | 0 | F | Cl | NH(CH₂)₃CH(NH₂)CONH₂ |
| 20 | 0 | F | Cl | NHCOCH₂CO₂Et |
| 21 | 0 | F | Cl | NHCOCH₂CO₂H |
| 22 | 0 | F | Cl | NHCOCH₂CONH₂ |
| 23 | 1 | F | Cl | NHCH₂CO₂Et |
| 24 | 1 | F | Cl | NHCH₂CO₂H |
| 25 | 1 | F | Cl | NHCH₂CONH₂ |
| 26 | 1 | F | Cl | NHCOCH₂CO₂Et |
| 27 | 1 | F | Cl | NHCOCH₂CO₂H |
| 28 | 1 | F | Cl | NHCOCH₂CONH₂ |

TABLE 5-continued

| Ex. # | n | A¹ | A² | R |
|---|---|---|---|---|
| 29 | 1 | F | Cl | NHCH₂CO₂Et |
| 30 | 1 | F | Cl | NHCH₂CO₂H |
| 31 | 1 | F | Cl | NHCH₂CONH₂ |

TABLE 6

[Structure: purine core with R¹ at 2-position, morpholine-2-carboxamide (RNHC(O)-) at 6-position via morpholine N, 4-chlorophenyl at 9-position, and A¹/A² substituted phenyl at 8-position]

| Ex. # | R¹ | A¹ | A² | R |
|---|---|---|---|---|
| 1 | H | Cl | H | H |
| 2 | H | Cl | H | CH₂CO₂Me |
| 3 | H | Cl | H | CH₂CO₂H |
| 4 | H | Cl | H | CH₂CONH₂ |
| 5 | H | Cl | H | CHCH₃CO₂Me |
| 6 | H | Cl | H | CHCH₃CO₂H |
| 7 | H | Cl | H | CHCH₃CONH₂ |
| 8 | H | Cl | H | CHCH₂OHCO₂Me |
| 9 | H | Cl | H | CHCH₂OHCO₂H |
| 10 | H | Cl | H | CHCH₂OHCONH₂ |
| 11 | H | Cl | H | CH₂CONHCH₂CO₂Me |
| 12 | H | Cl | H | CH₂CONHCH₂CO₂H |
| 13 | H | Cl | H | CH₂CONHCH₂CONH₂ |
| 14 | H | F | Cl | H |
| 15 | H | F | Cl | CH₂CO₂Me |
| 16 | H | F | Cl | CH₂CO₂H |
| 17 | H | F | Cl | CH₂CONH₂ |
| 18 | H | F | Cl | CHCH₃CO₂Me |
| 19 | H | F | Cl | CHCH₃CO₂H |
| 20 | H | F | Cl | CHCH₃CONH₂ |
| 21 | H | F | Cl | CHCH₂OHCO₂Me |
| 22 | H | F | Cl | CHCH₂OHCO₂H |
| 23 | H | F | Cl | CHCH₂OHCONH₂ |
| 24 | H | F | Cl | CH₂CONHCH₂CO₂Me |
| 25 | H | F | Cl | CH₂CONHCH₂CO₂H |
| 26 | H | F | Cl | CH₂CONHCH₂CONH₂ |
| 27 | CH₃ | Cl | H | H |
| 28 | CH₃ | Cl | H | CH₂CO₂Me |
| 29 | CH₃ | Cl | H | CH₂CO₂H |
| 30 | CH₃ | Cl | H | CH₂CONH₂ |
| 31 | CH₃ | Cl | H | CHCH₃CO₂Me |
| 32 | CH₃ | Cl | H | CHCH₃CO₂H |
| 33 | CH₃ | Cl | H | CHCH₃CONH₂ |

TABLE 6-continued

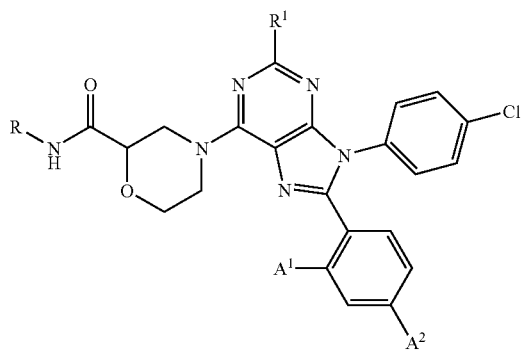

| Ex. # | R¹ | A¹ | A² | R |
|---|---|---|---|---|
| 34 | $CH_3$ | Cl | H | $CHCH_2OHCO_2Me$ |
| 35 | $CH_3$ | Cl | H | $CHCH_2OHCO_2H$ |
| 36 | $CH_3$ | Cl | H | $CHCH_2OHCONH_2$ |
| 37 | $CH_3$ | Cl | H | $CH_2CONHCH_2CO_2Me$ |
| 38 | $CH_3$ | Cl | H | $CH_2CONHCH_2CO_2H$ |
| 39 | $CH_3$ | Cl | H | $CH_2CONHCH_2CONH_2$ |
| 40 | $CH_3$ | F | Cl | H |
| 41 | $CH_3$ | F | Cl | $CH_2CO_2Me$ |
| 42 | $CH_3$ | F | Cl | $CH_2CO_2H$ |
| 43 | $CH_3$ | F | Cl | $CH_2CONH_2$ |
| 44 | $CH_3$ | F | Cl | $CHCH_3CO_2Me$ |
| 45 | $CH_3$ | F | Cl | $CHCH_3CO_2H$ |
| 46 | $CH_3$ | F | Cl | $CHCH_3CONH_2$ |
| 47 | $CH_3$ | F | Cl | $CHCH_2OHCO_2Me$ |
| 48 | $CH_3$ | F | Cl | $CHCH_2OHCO_2H$ |
| 49 | $CH_3$ | F | Cl | $CHCH_2OHCONH_2$ |
| 50 | $CH_3$ | F | Cl | $CH_2CONHCH_2CO_2Me$ |
| 51 | $CH_3$ | F | Cl | $CH_2CONHCH_2CO_2H$ |
| 52 | $CH_3$ | F | Cl | $CH_2CONHCH_2CONH_2$ |

TABLE 7

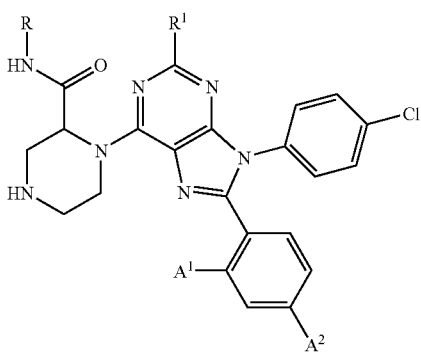

| Ex. # | R¹ | A¹ | A² | R |
|---|---|---|---|---|
| 1 | H | Cl | H | $CH_2CO_2Me$ |
| 2 | H | Cl | H | $CH_2CO_2H$ |
| 3 | H | Cl | H | $CH_2CONH_2$ |
| 4 | H | Cl | H | $CHCH_3CO_2Me$ |
| 5 | H | Cl | H | $CHCH_3CO_2H$ |
| 6 | H | Cl | H | $CHCH_3CONH_2$ |
| 7 | H | Cl | H | $CHCH_2OHCO_2Me$ |
| 8 | H | Cl | H | $CHCH_2OHCO_2H$ |
| 9 | H | Cl | H | $CHCH_2OHCONH_2$ |
| 10 | H | Cl | H | $CH_2CONHCH_2CO_2Me$ |
| 11 | H | Cl | H | $CH_2CONHCH_2CO_2H$ |
| 12 | H | Cl | H | $CH_2CONHCH_2CONH_2$ |
| 13 | H | F | Cl | $CH_2CO_2Me$ |
| 14 | H | F | Cl | $CH_2CO_2H$ |
| 15 | H | F | Cl | $CH_2CONH_2$ |
| 16 | H | F | Cl | $CHCH_3CO_2Me$ |
| 17 | H | F | Cl | $CHCH_3CO_2H$ |

TABLE 7-continued

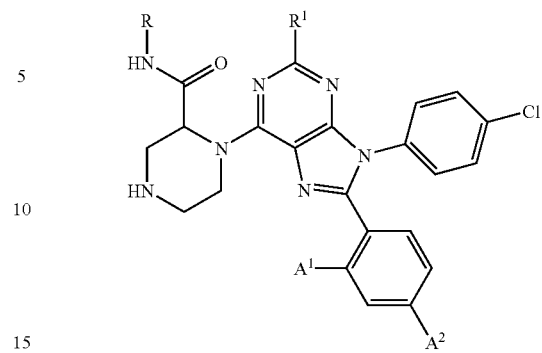

| Ex. # | R¹ | A¹ | A² | R |
|---|---|---|---|---|
| 18 | H | F | Cl | $CHCH_3CONH_2$ |
| 19 | H | F | Cl | $CHCH_2OHCO_2Me$ |
| 20 | H | F | Cl | $CHCH_2OHCO_2H$ |
| 21 | H | F | Cl | $CHCH_2OHCONH_2$ |
| 22 | H | F | Cl | $CH_2CONHCH_2CO_2Me$ |
| 23 | H | F | Cl | $CH_2CONHCH_2CO_2H$ |
| 24 | H | F | Cl | $CH_2CONHCH_2CONH_2$ |
| 25 | $CH_3$ | Cl | H | $CH_2CO_2Me$ |
| 26 | $CH_3$ | Cl | H | $CH_2CO_2H$ |
| 27 | $CH_3$ | Cl | H | $CH_2CONH_2$ |
| 28 | $CH_3$ | Cl | H | $CHCH_3CO_2Me$ |
| 29 | $CH_3$ | Cl | H | $CHCH_3CO_2H$ |
| 30 | $CH_3$ | Cl | H | $CHCH_3CONH_2$ |
| 31 | $CH_3$ | Cl | H | $CHCH_2OHCO_2Me$ |
| 32 | $CH_3$ | Cl | H | $CHCH_2OHCO_2H$ |
| 33 | $CH_3$ | Cl | H | $CHCH_2OHCONH_2$ |
| 34 | $CH_3$ | Cl | H | $CH_2CONHCH_2CO_2Me$ |
| 35 | $CH_3$ | Cl | H | $CH_2CONHCH_2CO_2H$ |
| 36 | $CH_3$ | Cl | H | $CH_2CONHCH_2CONH_2$ |
| 37 | $CH_3$ | F | Cl | $CH_2CO_2Me$ |
| 38 | $CH_3$ | F | Cl | $CH_2CO_2H$ |
| 39 | $CH_3$ | F | Cl | $CH_2CONH_2$ |
| 40 | $CH_3$ | F | Cl | $CHCH_3CO_2Me$ |
| 41 | $CH_3$ | F | Cl | $CHCH_3CO_2H$ |
| 42 | $CH_3$ | F | Cl | $CHCH_3CONH_2$ |
| 43 | $CH_3$ | F | Cl | $CHCH_2OHCO_2Me$ |
| 44 | $CH_3$ | F | Cl | $CHCH_2OHCO_2H$ |
| 45 | $CH_3$ | F | Cl | $CHCH_2OHCONH_2$ |
| 46 | $CH_3$ | F | Cl | $CH_2CONHCH_2CO_2Me$ |
| 47 | $CH_3$ | F | Cl | $CH_2CONHCH_2CO_2H$ |
| 48 | $CH_3$ | F | Cl | $CH_2CONHCH_2CONH_2$ |

TABLE 8

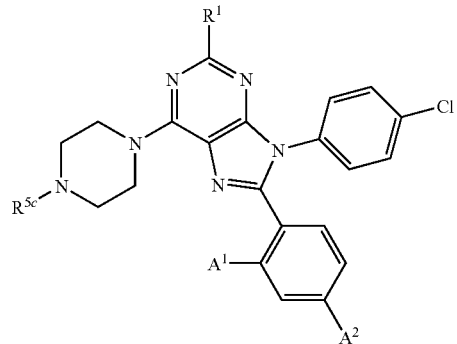

| Ex. # | R¹ | A¹ | A² | $R^{5c}$ |
|---|---|---|---|---|
| 1 | H | Cl | H | $CH_2CO_2Me$ |
| 2 | H | Cl | H | $CH_2CO_2H$ |
| 3 | H | Cl | H | $CH_2CONH_2$ |
| 4 | H | Cl | H | $CH_2CONHCH_2CO_2Me$ |
| 5 | H | Cl | H | $CH_2CONHCH_2CO_2H$ |

TABLE 8-continued

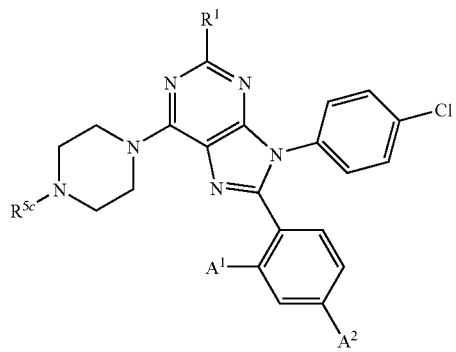

| Ex. # | R¹ | A¹ | A² | R⁵ᶜ |
|---|---|---|---|---|
| 6 | H | Cl | H | CH₂CONHCH₂CONH₂ |
| 7 | H | Cl | H | COCH₂CO₂Me |
| 8 | H | Cl | H | COCH₂CO₂H |
| 9 | H | Cl | H | COCH₂CONH₂ |
| 10 | H | Cl | H | COCH₂CONHCH₂CO₂Et |
| 11 | H | Cl | H | COCH₂CONHCH₂CO₂H |
| 12 | H | Cl | H | COCH₂CONHCH₂CONH₂ |
| 13 | CH₃ | Cl | H | CH₂CO₂Me |
| 14 | CH₃ | Cl | H | CH₂CO₂H |
| 15 | CH₃ | Cl | H | CH₂CONH₂ |
| 16 | CH₃ | Cl | H | CH₂CONHCH₂CO₂Me |
| 17 | CH₃ | Cl | H | CH₂CONHCH₂CO₂H |
| 18 | CH₃ | Cl | H | CH₂CONHCH₂CONH₂ |
| 19 | CH₃ | Cl | H | COCH₂CO₂Me |
| 20 | CH₃ | Cl | H | COCH₂CO₂H |
| 21 | CH₃ | Cl | H | COCH₂CONH₂ |
| 22 | CH₃ | Cl | H | COCH₂CONHCH₂CO₂Et |
| 23 | CH₃ | Cl | H | COCH₂CONHCH₂CO₂H |
| 24 | CH₃ | Cl | H | COCH₂CONHCH₂CONH₂ |
| 25 | H | F | Cl | CH₂CO₂Me |
| 26 | H | F | Cl | CH₂CO₂H |
| 27 | H | F | Cl | CH₂CONH₂ |
| 28 | H | F | Cl | CH₂CONHCH₂CO₂Me |
| 29 | H | F | Cl | CH₂CONHCH₂CO₂H |
| 30 | H | F | Cl | CH₂CONHCH₂CONH₂ |
| 31 | H | F | Cl | COCH₂CO₂Me |
| 32 | H | F | Cl | COCH₂CO₂H |
| 33 | H | F | Cl | COCH₂CONH₂ |
| 34 | H | F | Cl | COCH₂CONHCH₂CO₂Et |
| 35 | H | F | Cl | COCH₂CONHCH₂CO₂H |
| 36 | H | F | Cl | COCH₂CONHCH₂CONH₂ |
| 37 | CH₃ | F | Cl | CH₂CO₂Me |
| 38 | CH₃ | F | Cl | CH₂CO₂H |
| 39 | CH₃ | F | Cl | CH₂CONH₂ |
| 40 | CH₃ | F | Cl | CH₂CONHCH₂CO₂Me |
| 41 | CH₃ | F | Cl | CH₂CONHCH₂CO₂H |
| 42 | CH₃ | F | Cl | CH₂CONHCH₂CONH₂ |
| 43 | CH₃ | F | Cl | COCH₂CO₂Me |
| 44 | CH₃ | F | Cl | COCH₂CO₂H |
| 45 | CH₃ | F | Cl | COCH₂CONH₂ |
| 46 | CH₃ | F | Cl | COCH₂CONHCH₂CO₂Et |
| 47 | CH₃ | F | Cl | COCH₂CONHCH₂CO₂H |
| 48 | CH₃ | F | Cl | COCH₂CONHCH₂CONH₂ |

Numerous modifications and variations of the present invention are possible in light of the above teachings. It is therefore to be understood that within the scope of the appended claims, the invention may be practiced otherwise that as specifically described herein.

What is claimed is:

1. A compound of formula I or a stereoisomer or pharmaceutically acceptable salt thereof:

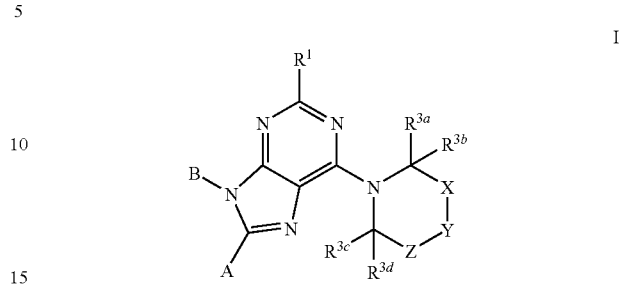

wherein:
one of A and B is selected from a substituted aryl and a substituted heteroaryl, the substituent being selected from the group consisting of $CO_2R$, $RO_2C(CH_2)_mCHQ(CH_2)_mNHC(O)(CH_2)_m—$, $R^c_2NC(O)(CH_2)_mCHQ(CH_2)_mNHC(O)(CH_2)_m—$, $RO_2C(CH_2)_mCHQ(CH_2)_mNHC(O)(CH_2)_mCHQ(CH_2)_mNHC(O)(CH_2)_m—$, $R^c_2NC(O)(CH_2)_mCHQ(CH_2)_mNHC(O)(CH_2)_mCHQ(CH_2)_mNHC(O)(CH_2)_m—$, $(CH_2)_nCO_2R$, $O(CH_2)_nCO_2R$, $OCH_2CH=CHCO_2R$, $CH_2—O—(CH_2)_nCO_2R$, $CH_2OCH_2CH=CHCO_2R$, $O(CH_2)_nPO(OR)_2$, $CH_2—O—(CH_2)_nPO(OR)_2$, $NR^a(CH_2)_mCO_2R$, $NR^a(CH_2)_nPO(OR)_2$, $NR^aCH_2CH=CHCO_2R$, $NR^aSO_2CH_3$, $NR^aCO(CH_2)_nCO_2R$, $O(CH_2)_nC_6H_4CO_2R$, $O(CH_2)_nC_6H_4(CH_2)_nCO_2R$, $CH_2—O—(CH_2)_nC_6H_4CO_2R$, $O(CH_2)_nC_6H_4CONR^c_2$, $O(CH_2)_nC_6H_4(CH_2)_nCONR^c_2$, $CH_2—O—(CH_2)_nC_6H_4CONR^c_2$, $O(CH_2)_nC_6H_4$-tetrazole, $CH_2—O—(CH_2)_nC_6H_4$-tetrazole, $O(CH_2)_nC_6H_4(CH_2)_n$-tetrazole, $NR^a(CH_2)_nC_6H_4CO_2R$, $CH_2NR^a(CH_2)_nC_6H_4CO_2R$, $NR^a(CH_2)_nC_6H_4CONR^c_2$, $CH_2NR^a(CH_2)_nC_6H_4CONR^c_2$, $NR^a(CH_2)_nC_6H_4$-tetrazole, $CH_2NR^a(CH_2)_nC_6H_4$-tetrazole, $—CN$, $(CH_2)_mC(=NH)NH_2$, $(CH_2)_mNHC(=NH)NH_2$, $(CH_2)_mNHC(=CHNO_2)NH_2$, $(CH_2)_mNHC(=NCN)NH_2$, $CONR^c_2$, $(CH_2)_nCONR^c_2$, $O(CH_2)_nCONR^c_2$, $CH_2—O—(CH_2)_nCONR^c_2$, $NR^a(CH_2)_mCONHR^a$, $OCH_2CH=CHCONR^c_2$, $CH_2OCH_2CH=CHCONR^c_2$, $NR^aCH_2CH=CHCONR^c_2$, tetrazole, $O(CH_2CH_2O)_pR$, $NR^a(CH_2CH_2O)_pR$, $SONH_2$, and $SO_2NR^aCH_3$;

the other of A and B is selected from an aryl and an heteroaryl, the aryl or heteroaryl being substituted with 0-3 substituents selected from halo, $C_{1-4}$ alkoxy, $C_{1-4}$ alkyl, $C_{1-4}$ haloalkyl, and cyano;

X is selected from a bond, $—CH_2CH_2—$ and $—C(R^{4a})(R^{4b})—$;

Y is selected from O, S, $NR^{5c}$, C(O), C=NOH, and $—C(R^{5a})(R^{5b})—$;

Z is selected from a bond, $—CH_2CH_2—$ and $—C(R^{4c})(R^{4d})—$;

R¹ is selected from H, $C_{1-4}$ alkyl, $C_{1-4}$ haloalkyl, and $C_{1-4}$ alkoxy;

$R^{3a}$, $R^{3b}$, $R^{3c}$, $R^{3d}$, $R^{4a}$, $R^{4b}$, $R^{4c}$, $R^{4d}$, $R^{5a}$, and $R^{5b}$ are each independently selected from H, cyano, OH, $NH_2$, $H_2NC(O)—$, $C_{1-6}$ alkyl, $C_{1-6}$ alkoxy, $C_{1-6}$ acyloxy, $C_{1-6}$ acyl, $C_{1-3}$ alkyl-OC(O)—, $C_{1-4}$ alkyl-NHC(O)—, $(C_{1-4}$ alkyl$)_2$NC(O), $C_{3-8}$ cycloalkyl, $C_{1-6}$ alkylamino-, $(C_{1-4}$ alkyl$)_2$amino-, $C_{3-6}$ cycloalkylamino-, $C_{1-6}$ acylamino-, aryl$C_{1-4}$ alkylamino-, heteroaryl$C_{1-4}$ alkylamino-, aryl, heteroaryl, a 3-6 membered heterocycle, and a 3-8 membered carbocyclic ring, wherein the alkyl, cycloalkyl, aryl, heterocycle, and heteroaryl groups are substituted with 0-2 $R^6$;

alternatively, $R^{5a}$ and $R^{5b}$ taken together with the carbon atom to which each is attached form a ring selected from a 3-6 membered heterocyclic ring, a 5-6 membered lactone ring, and a 4-6 membered lactam ring, wherein the ring is substituted with 0-2 $R^6$ and the lactone ring and the lactam ring optionally contain an additional heteroatom selected from O, N, NR, and S;

$R^{5c}$ is selected from H, $C_{1-6}$ alkyl, $C_{3-6}$ cycloalkyl, $C_{1-3}$ alkylsulfonyl-, $C_{1-3}$ alkylaminosulfonyl-, $diC_{1-3}$ alkylaminosulfonyl-, $C_{1-6}$ acyl, $C_{1-6}$ alkyl-OC(O)—, aryl, and heteroaryl, wherein the alkyl, aryl, and heteroaryl groups are substituted with 0-2 $R^6$;

$R^6$ at each occurrence is independently selected from halo, —CN, OH, $C_{1-6}$ alkyl, $C_{2-6}$ alkenyl, $C_{3-8}$ cycloalkyl, $C_{1-6}$ alkoxy, $C_{1-6}$ acyl, $C_{1-6}$ acyloxy, $C_{1-6}$ alkyl-OC(O)—, $C_{1-4}$ alkyl-NHC(O)—, $(C_{1-4}$ alkyl$)_2$NC(O), $NH_2$, $C_{1-6}$ alkylamino-, $(C_{1-4}$ alkyl$)_2$amino-, $C_{3-6}$ cycloalkylamino-, $C_{1-6}$ acylamino-, $C(O)NH_2$, —$CONH(CH_2)_m$ $CHQ(CH_2)_mCO_2R$, and —$CONH(CH_2)_mCHQ(CH_2)_m$ $CONHR$;

alternatively, $R^{3a}$ and $R^{3b}$ taken together with $R^{3c}$ and $R^{3d}$ forms a bond, a methylene bridge, or an ethylene bridge;

alternatively, $R^{4a}$ and $R^{4b}$ taken together with $R^{3c}$ and $R^{3d}$ forms a bond, a methylene bridge, or an ethylene bridge; and, alternatively, either $R^{4c}$ and $R^{4d}$ taken together with $R^{4a}$ and $R^{4b}$ or with $R^{3a}$ and $R^{3b}$ forms a bond, a methylene bridge, or an ethylene bridge;

Q is selected from H, OH, $C_{1-6}$ alkyl, $C_{1-6}$alkylene-OH, $(CH_2)_mNR^c_2$, $(CH_2)_nCONR^c_2$, $(CH_2)_nNHCONR^c_2$, $(CH_2)_mC(=NH)NH_2$, $(CH_2)_m$—$C_{3-6}$-cycloalkyl, $(CH_2)_m$-heteroaryl, and $(CH_2)_m$-aryl, wherein each aryl and heteroaryl is substituted with 0-2 groups selected from $CF_3$, halogen, $C_{1-4}$ alkyl, —CN, $CONR^c_2$, $NO_2$, $NR_2$, OR, $NHSO_2CH_3$, and SONHR;

R is independently selected from H and $C_{1-6}$ alkyl;

$R^a$ is independently selected from H, $C_{1-6}$ alkyl, $C_{2-6}$ alkenyl, and $C_{2-6}$ alkynyl;

$R^c$ is independently selected from H, OH, alkyl, $C_{1-6}$ alkyl, $C_{2-6}$ alkenyl, aryl$C_{1-4}$ alkyl- and $C_{2-6}$ alkynyl, where each alkyl may be optionally substituted with a hydroxyl group on the alkyl chain, and the aryl group is optionally substituted with 0-2 groups selected from $CF_3$, halogen, $C_{1-4}$ alkyl, —CN, $CONR_2$, $NO_2$, $NR_2$, OR, $NHSO_2CH_3$ and SONHR;

m is selected from 0, 1, 2, 3, and 4; and, n is selected from 1, 2, 3, and 4.

2. A compound of claim 1, wherein the compound is of formula IIa or a stereoisomer or pharmaceutically acceptable salt thereof:

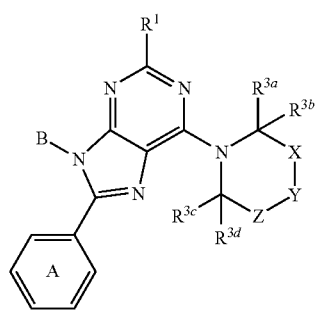

IIa wherein:

ring A is substituted with 0-3 substituents selected from the group consisting of halo, $C_{1-4}$ alkoxy, $C_{1-4}$ alkyl, $C_{1-4}$ haloalkyl, and cyano.

3. A compound of formula I or a stereoisomer or pharmaceutically acceptable salt thereof:

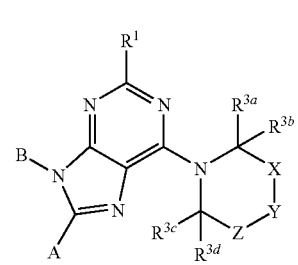

I wherein:

A and B are selected from an optionally substituted aryl or an optionally substituted heteroaryl, the substituents being from one to three independently selected from halo, $C_{1-4}$ alkoxy, $C_{1-4}$ alkyl, $C_{1-4}$ haloalkyl, and cyano;

X is selected from a bond, —$CH_2CH_2$— and —$C(R^{4a})(R^{4b})$—;

Y is selected from O, S, $NR^{5c}$, C(O), C=NOH, and —$C(R^{5a})(R^{5b})$—;

Z is selected from a bond, —$CH_2CH_2$— and —$C(R^{4c})(R^{4d})$—;

$R^1$ is selected from $(CH_2)_mCO_2R$, $RO_2C(CH_2)_mCHQ$ $(CH_2)_mNHC(O)(CH_2)_n$—, $R^c_2NC(O)(CH_2)_mCHQ$ $(CH_2)_mNHC(O)(CH_2)_n$—, $OCH_2CH=CHCO_2R$, $CH_2$—O—$(CH_2)_nCO_2R$, $CH_2OCH_2CH=CHCO_2R$, $O(CH_2)_nPO(OR)_2$, $CH_2$—O—$(CH_2)_nPO(OR)_2$, $NR^a$ $(CH_2)_mCO_2R$, $NR^a(CH_2)_nPO(OR)_2$, $NR^aCH_2CH=CHCO_2R$, $NR^aSO_2CH_3$, $NR^aCO(CH_2)_n$ $CO_2R$, $(CH_2)_mNHC(=NH)NH_2$, $(CH_2)_mNHC$ $(=CHNO_2)NH_2$, $(CH_2)_mNHC(=NCN)NH_2$, $(CH_2)_n$ $CONR^c_2$, $O(CH_2)_nCONR^c_2$, $CH_2$—O—$(CH_2)_n$ $CONR^c_2$, $(CH_2)_mNR^a(CH_2)_nCONHR^a$, $(CH_2)_mNR^aC$ $(O)(CH_2)_nCO_2R$, $(CH_2)_mNR^aC(O)(CH_2)_nCONR^c_2$, $(CH_2)_mNR^a(CH_2)_mCHQCO_2R$, $(CH_2)_mNR^a(CH_2)_m$ $CHQCONR^c_2$, $(CH_2)_nCH(NHR^a)CO_2R$, $(CH_2)_nCH$ $(NHR^a)CONHR^a$, $CH_2OCH_2CH=CHCONR^c_2$, $NR^aCH_2CH=CHCONR^c_2$, and $(CH_2)_m$tetrazole, $R^{3a}$, $R^{3b}$, $R^{3c}$, $R^{3d}$, $R^{4a}$, $R^{4b}$, $R^{4c}$, $R^{4d}$, $R^{5a}$, and $R^{5b}$ are each independently selected from H, cyano, OH, $NH_2$, $H_2NC$ (O)—, $C_{1-6}$ alkyl, $C_{1-6}$ alkoxy, $C_{1-6}$ acyloxy, $C_{1-6}$ acyl, $C_{1-3}$ alkyl-OC(O)—, $C_{1-4}$ alkyl-NHC(O)—, $C_{1-4}$ alkyl$)_2$ NC(O), $C_{3-8}$ cycloalkyl, $C_{1-6}$ alkylamino-, $(C_{1-4}$ alkyl$)_2$ amino-, $C_{3-6}$ cycloalkylamino-, $C_{1-6}$ acylamino-, aryl$C_{1-4}$ alkylamino-, heteroaryl$C_{1-4}$ alkylamino-, aryl, heteroaryl, a 3-6 membered heterocycle, and a 3-8 membered carbocyclic ring, wherein the alkyl, cycloalkyl, aryl, heterocycle, and heteroaryl groups are substituted with 0-2 $R^6$;

alternatively, $R^{5a}$ and $R^{5b}$ taken together with the carbon atom to which each is attached form a ring selected from a 3-6 membered heterocyclic ring, a 5-6 membered lactone ring, and a 4-6 membered lactam ring, wherein the ring is substituted with 0-2 $R^6$ and the lactone ring and the lactam ring optionally contain an additional heteroatom selected from O, N, NR, and S;

$R^{5c}$ is selected from H, $C_{1-6}$ alkyl, $C_{3-6}$ cycloalkyl, $C_{1-3}$ alkylsulfonyl-, $C_{1-3}$ alkylaminosulfonyl-, $diC_{1-3}$ alkylaminosulfonyl-, $C_{1-6}$ acyl, $C_{1-6}$ alkyl-OC(O)—, aryl, and heteroaryl, wherein the alkyl, aryl, and heteroaryl groups are substituted with 0-2 $R^6$;

R⁶ at each occurrence is independently selected from halo, —CN, OH, $C_{1-6}$ alkyl, $C_{2-6}$ alkenyl, $C_{3-8}$ cycloalkyl, $C_{1-6}$ alkoxy, $C_{1-6}$ acyl, $C_{1-6}$ acyloxy, $C_{1-6}$ alkyl-OC(O)—, $C_{1-4}$ alkyl-NHC(O)—, $(C_{1-4}$ alkyl$)_2$NC(O), $NH_2$, $C_{1-6}$ alkylamino-, $(C_{1-4}$ alkyl$)_2$amino-, $C_{3-6}$ cycloalkylamino-, $C_{1-6}$ acylamino-, $C(O)NH_2$, —$CONH(CH_2)_m$ $CHQ(CH_2)_mCO_2R$, and —$CONH(CH_2)_mCHQ(CH_2)_m$ CONHR;

alternatively, $R^{3a}$ and $R^{3b}$ taken together with $R^{3c}$ and $R^{ad}$ forms a bond, a methylene bridge, or an ethylene bridge;

alternatively, $R^{4a}$ and $R^{4b}$ taken together with $R^{3c}$ and $R^{ad}$ forms a bond, a methylene bridge, or an ethylene bridge; and, alternatively, either $R^{4c}$ and $R^{4d}$ taken together with $R^{4a}$ and $R^{4b}$ or with $R^{3a}$ and $R^{3b}$ forms a bond, a methylene bridge, or an ethylene bridge;

Q is selected from H, OH, $C_{1-6}$ alkyl, $C_{1-6}$ alkylene-OH, $(CH_2)_mNR^c_2$, $(CH_2)_nCONR^c_2$, $(CH_2)_nNHCONR^c_2$, $(CH_2)_mC(=NH)NH_2$, $(CH_2)_m$—$C_{3-6}$cycloalkyl, $(CH_2)_m$-heteroaryl, and $(CH_2)_m$-aryl, wherein each aryl and heteroaryl is substituted with 0-2 groups selected from $CF_3$, halogen, $C_{1-4}$ alkyl, —CN, $CONR^c_2$, $NO_2$, $NR_2$, OR, $NHSO_2CH_3$, and SONHR;

R is independently selected from H and $C_{1-6}$ alkyl;

$R^a$ is independently selected from H, $C_{1-6}$ alkyl, $C_{2-6}$ alkenyl, and $C_{2-6}$ alkynyl;

$R^c$ is independently selected from H, OH, $C_{1-6}$ alkyl, $C_{2-6}$ alkenyl, aryl$C_{1-4}$ alkyl- and $C_{2-6}$ alkynyl, where each alkyl may be optionally substituted with a hydroxyl group on the alkyl chain, and the aryl group is optionally substituted with 0-2 groups selected from $CF_3$, halogen, $C_{1-4}$ alkyl, —CN, $CONR_2$, $NO_2$, $NR_2$, OR, $NHSO_2CH_3$, and SONHR;

m is selected from 0, 1, 2, 3, and 4; and, n is selected from 1, 2, 3, and 4.

4. A compound of claim 3, wherein the compound is of formula IIa or a stereoisomer or pharmaceutically acceptable salt thereof:

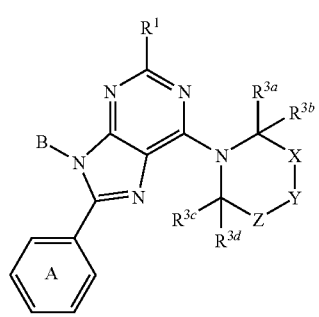

IIa wherein:

ring A is substituted with 0-3 substituents selected from the group consisting of halo, $C_{1-4}$ alkoxy, $C_{1-4}$ alkyl, $C_{1-4}$ haloalkyl, and cyano.

5. A compound of formula I or a stereoisomer or pharmaceutically acceptable salt thereof:

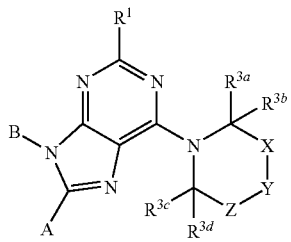

I wherein:

A and B are selected from an optionally substituted aryl or an optionally substituted heteroaryl, the substituents being from one to three independently selected from halo, $C_{1-4}$ alkoxy, $C_{1-4}$ alkyl, $C_{1-4}$ haloalkyl, and cyano;

X is selected from a bond, —$CH_2CH_2$— and —$C(R^{4a})(R^{4b})$—;

Y is selected from O, S, $NR^{5c}$, C(O), C=NOH, and —$C(R^{5a})(R^{5b})$—;

Z is selected from a bond, —$CH_2CH_2$— and —$C(R^{4c})(R^{4d})$—;

$R^1$ is selected from H, $C_{1-4}$ alkyl, $C_{1-4}$ haloalkyl, and $C_{1-4}$ alkoxy;

one or two of $R^{3a}$, $R^{3b}$, $R^{3c}$, $R^{3d}$, $R^{4a}$, $R^{4b}$, $R^{4c}$, $R^{4d}$, $R^{5a}$, and $R^{5b}$ are selected from $RO_2C(CH_2)_mCHQ(CH_2)_m$—, $R_2N(O)C(CH_2)_mCHQ(CH_2)_m$—, $R_2NS(O_2)C(CH_2)_mCHQ(CH_2)_m$—, $RO_2C(CH_2)_mCHQ(CH_2)_mNHC(O)$—, $R^c_2NC(O)(CH_2)_mCHQ(CH_2)_mNHC(O)$—, $RO_2C(CH_2)_mCHQ(CH_2)_mNHC(O)(CH_2)_mCHQ(CH_2)_mNHC(O)$—, $R^c_2NC(O)(CH_2)_mCHQ(CH_2)_mNHC(O)(CH_2)_mCHQ(CH_2)_mNHC(O)$—, $RO_2C(CH_2)_mCHQ(CH_2)_mNHC(O)(CH_2)_mCHQ(CH_2)_mNHC(O)(CH_2)_m$ CHQ$(CH_2)_mNHC(O)$—, $R^c_2NC(O)(CH_2)_mCHQ(CH_2)_mNHC(O)(CH_2)_mCHQ(CH_2)_mNHC(O)(CH_2)_m$ CHQ$(CH_2)_mN$ HC(O)—, $ROS(O_2)(CH_2)_mCHQ(CH_2)_mNHC(O)$—, and $R^c_2NS(O_2)(CH_2)_mCHQ(CH_2)_mNHC(O)$—;

the remainder of $R^{3a}$, $R^{3b}$, $R^{3c}$, $R^{3d}$, $R^{4a}$, $R^{4b}$, $R^{4c}$, $R^{4d}$, $R^{5a}$, and $R^{5b}$ are each independently selected from H, cyano, OH, $NH_2$, $C_{1-4}$ alkyl-NH—, $(C_{1-4}$ alkyl$)_2$N—, $H_2NC(O)$—, $C_{1-6}$ alkyl, $C_{1-6}$ alkoxy, $C_{1-6}$ acyloxy, $C_{1-6}$ acyl, $C_{1-3}$ alkyl-OC(O)—, $C_{1-4}$ alkyl-NHC(O)—, $C_{1-4}$ alkyl$)_2$ NC(O), $C_{3-8}$ cycloalkyl, $C_{1-6}$ alkylamino-, $(C_{1-4}$ alkyl$)_2$ amino-, $C_{3-6}$ cycloalkylamino-, $C_{1-6}$ acylamino-, aryl$C_{1-4}$ alkylamino-, heteroaryl$C_{1-4}$ alkylamino-, aryl, heteroaryl, a 3-6 membered heterocycle, and a 3-8 membered carbocyclic ring, wherein the alkyl, cycloalkyl, aryl, heterocycle, and heteroaryl groups are substituted with 0-2 $R^6$;

alternatively, $R^{5a}$ and $R^{5b}$ taken together with the carbon atom to which each is attached form a ring selected from a 3-6 membered heterocyclic ring, a 5-6 membered lactone ring, and a 4-6 membered lactam ring, wherein the ring is substituted with 0-2 $R^6$ and the lactone ring and the lactam ring optionally contain an additional heteroatom selected from O, N, NR, and S;

$R^{5c}$ is selected from H, $C_{1-6}$ alkyl, $C_{3-6}$ cycloalkyl, $C_{1-3}$ alkylsulfonyl-, $C_{1-3}$ alkylaminosulfonyl-, di$C_{1-3}$ alkylaminosulfonyl-, $C_{1-6}$ acyl, $C_{1-6}$ alkyl-OC(O)—, aryl, and heteroaryl, wherein the alkyl, aryl, and heteroaryl groups are substituted with 0-2 $R^6$;

$R^6$ at each occurrence is independently selected from halo, —CN, OH, $C_{1-6}$ alkyl, $C_{2-6}$ alkenyl, $C_{3-8}$ cycloalkyl, $C_{1-6}$ alkoxy, $C_{1-6}$ acyl, $C_{1-6}$ acyloxy, $C_{1-6}$ alkyl-OC (O)—, $C_{1-4}$ alkyl-NHC(O)—, ($C_{1-4}$ alkyl)$_2$NC(O), NH$_2$, $C_{1-6}$ alkylamino-, ($C_{1-4}$ alkyl)$_2$amino-, $C_{3-6}$ cycloalkylamino-, $C_{1-6}$ acylamino-, C(O)NH$_2$, —CONH(CH$_2$)$_m$CHQ(CH$_2$)$_m$CO$_2$R, and —CONH(CH$_2$)$_m$CHQ(CH$_2$)$_m$CONHR;

alternatively, $R^{3a}$ and $R^{3b}$ taken together with $R^{3c}$ and $R^{3d}$ forms a bond, a methylene bridge, or an ethylene bridge;

alternatively, $R^{4a}$ and $R^{4b}$ taken together with $R^{3c}$ and $R^{3d}$ forms a bond, a methylene bridge, or an ethylene bridge; and, alternatively, either $R^{4c}$ and $R^{4d}$ taken together with $R^{4a}$ and $R^{4b}$ or with $R^{3a}$ and $R^{3b}$ forms a bond, a methylene bridge, or an ethylene bridge;

Q is selected from H, OH, $C_{1-6}$ alkyl, $C_{1-6}$alkylene-OH, (CH$_2$)$_m$NR$^c_2$, (CH$_2$)$_n$CONR$^c_2$, (CH$_2$)$_n$NHCONR$^c_2$, (CH$_2$)$_m$C(=NH)NH$_2$, (CH$_2$)$_m$—$C_{3-6}$-cycloalkyl, (CH$_2$)$_m$-heteroaryl, and (CH$_2$)$_m$-aryl, wherein each aryl and heteroaryl is substituted with 0-2 groups selected from CF$_3$, halogen, $C_{1-4}$ alkyl, —CN, CONR$^c_2$, NO$_2$, NR$_2$, OR, NHSO$_2$CH$_3$, and SONHR;

R is independently selected from H and $C_{1-6}$ alkyl;

$R^c$ is independently selected from H, OH, alkyl, $C_{1-6}$ alkyl, $C_{2-6}$ alkenyl, arylC$_{1-4}$ alkyl- and $C_{2-6}$ alkynyl, where each alkyl may be optionally substituted with a hydroxyl group on the alkyl chain, and the aryl group is optionally substituted with 0-2 groups selected from CF$_3$, halogen, $C_{1-4}$ alkyl, —CN, CONR$_2$, NO$_2$, NR$_2$, OR, NHSO$_2$CH$_3$ and SONHR;

m is selected from 0, 1, 2, 3, and 4; and, n is selected from 1, 2, 3, and 4.

6. A compound of claim 5, wherein the compound is of formula IIa or a stereoisomer or pharmaceutically acceptable salt thereof:

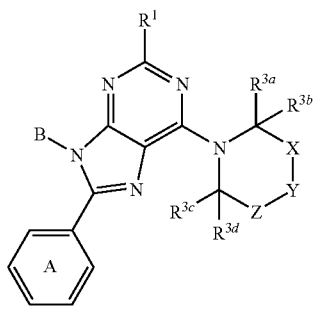

IIa wherein:

ring A is substituted with 0-3 substituents selected from the group consisting of halo, $C_{1-4}$ alkoxy, $C_{1-4}$ alkyl, $C_{1-4}$ haloalkyl, and cyano.

7. A compound of claim 5, wherein:

$R^{3a}$ is selected from RO$_2$C(CH$_2$)$_m$CHQ(CH$_2$)$_m$—, R$_2$N(O)C(CH$_2$)$_m$CHQ(CH$_2$)$_m$—, R$_2$NS(O$_2$)C(CH$_2$)$_m$CHQ(CH$_2$)$_m$—, RO$_2$C(CH$_2$)$_m$CHQ(CH$_2$)$_m$NHC(O)—, R$^c_2$NC(O)(CH$_2$)$_m$CHQ(CH$_2$)$_m$NHC(O)—, RO$_2$C(CH$_2$)$_m$CHQ(CH$_2$)$_m$NHC(O)(CH$_2$)$_m$CHQ(CH$_2$)$_m$NHC(O)—, R$^c_2$NC(O)(CH$_2$)$_m$CHQ(CH$_2$)$_m$NHC(O)(CH$_2$)$_m$CHQ(CH$_2$)$_m$NHC(O)—, RO$_2$C(CH$_2$)$_m$CHQ(CH$_2$)$_m$NHC(O)(CH$_2$)$_m$CHQ(CH$_2$)$_m$NHC(O)(CH$_2$)$_m$CHQ(CH$_2$)$_m$NHC(O)—, R$^c_2$NC(O)(CH$_2$)$_m$CHQ(CH$_2$)$_m$NHC(O)(CH$_2$)$_m$CHQ(CH$_2$)$_m$NHC(O)(CH$_2$)$_m$CHQ(CH$_2$)$_m$NHC(O)—, ROS(O$_2$)(CH$_2$)$_m$CHQ(CH$_2$)$_m$NHC(O)—, and, R$^c_2$NS(O$_2$)(CH$_2$)$_m$CHQ(CH$_2$)$_m$NHC(O)—.

8. A compound of claim 7, wherein the compound is of formula IIa or a stereoisomer or pharmaceutically acceptable salt thereof:

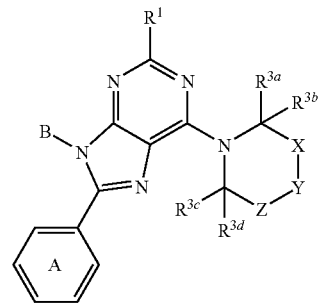

IIa wherein:

ring A is substituted with 0-3 substituents selected from the group consisting of halo, $C_{1-4}$ alkoxy, $C_{1-4}$ alkyl, $C_{1-4}$ haloalkyl, and cyano.

9. A compound of claim 5, wherein:

$R^{3c}$ is selected from RO$_2$C(CH$_2$)$_m$CHQ(CH$_2$)$_m$—, R$_2$N(O)C(CH$_2$)$_m$CHQ(CH$_2$)$_m$—, R$_2$NS(O$_2$)C(CH$_2$)$_m$CHQ(CH$_2$)$_m$—, RO$_2$C(CH$_2$)$_m$CHQ(CH$_2$)$_m$NHC(O)—, R$^c_2$NC(O)(CH$_2$)$_m$CHQ(CH$_2$)$_m$NHC(O)—, RO$_2$C(CH$_2$)$_m$CHQ(CH$_2$)$_m$NHC(O)(CH$_2$)$_m$CHQ(CH$_2$)$_m$NHC(O)—, R$^c_2$NC(O)(CH$_2$)$_m$CHQ(CH$_2$)$_m$NHC(O)(CH$_2$)$_m$CHQ(CH$_2$)$_m$NHC(O)—, RO$_2$C(CH$_2$)$_m$CHQ(CH$_2$)$_m$NHC(O)(CH$_2$)$_m$CHQ(CH$_2$)$_m$NHC(O)(CH$_2$)$_m$CHQ(CH$_2$)$_m$NHC(O)—, R$^c_2$NC(O)(CH$_2$)$_m$CHQ(CH$_2$)$_m$NHC(O)(CH$_2$)$_m$CHQ(CH$_2$)$_m$NHC(O)—, ROS(O$_2$)(CH$_2$)$_m$CHQ(CH$_2$)$_m$NHC(O)—, and, R$^c_2$NS(O$_2$)(CH$_2$)$_m$CHQ(CH$_2$)$_m$NHC(O)—.

10. A compound of claim 9, wherein the compound is of formula IIa or a stereoisomer or pharmaceutically acceptable salt thereof:

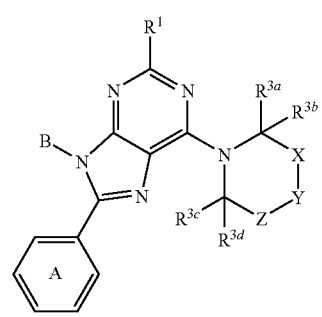

IIa wherein:

ring A is substituted with 0-3 substituents selected from the group consisting of halo, $C_{1-4}$ alkoxy, $C_{1-4}$ alkyl, $C_{1-4}$ haloalkyl, and cyano.

11. A compound of claim 5, wherein the compound is of formula IIIa or a stereoisomer or pharmaceutically acceptable salt thereof:

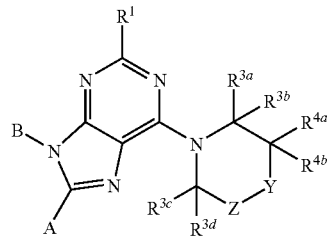

wherein:
$R^{4a}$ is selected from $RO_2C(CH_2)_mCHQ(CH_2)_m-$, $R_2N(O)C(CH_2)_mCHQ(CH_2)_m-$, $R_2NS(O_2)C(CH_2)_mCHQ(CH_2)_m-$, $RO_2C(CH_2)_mCHQ(CH_2)_mNHC(O)-$, $R^c{}_2NC(O)(CH_2)_mCHQ(CH_2)_mNHC(O)-$, $RO_2C(CH_2)_mCHQ(CH_2)_mNHC(O)(CH_2)_mCHQ(CH_2)_mNHC(O)-$, $R^c{}_2NC(O)(CH_2)_mCHQ(CH_2)_mNHC(O)(CH_2)_mCHQ(CH_2)_mNHC(O)-$, $RO_2C(CH_2)_mCHQ(CH_2)_mNHC(O)(CH_2)_mCHQ(CH_2)_mNHC(O)(CH_2)_mCHQ(CH_2)_mNHC(O)-$, $R^c{}_2NC(O)(CH_2)_mCHQ(CH_2)_mNHC(O)(CH_2)_mCHQ(CH_2)_mNHC(O)(CH_2)_mCHQ(CH_2)_mNHC(O)-$, $ROS(O_2)(CH_2)_mCHQ(CH_2)_mNHC(O)-$, and $R^c{}_2NS(O_2)(CH_2)_mCHQ(CH_2)_mNHC(O)-$.

12. A compound of claim 11, wherein the compound is of formula IIIb or a stereoisomer or pharmaceutically acceptable salt thereof:

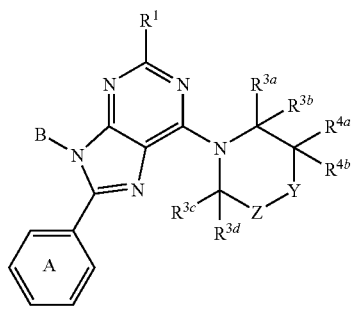

wherein:
ring A is substituted with 0-3 substituents selected from the group consisting of halo, $C_{1-4}$ alkoxy, $C_{1-4}$ alkyl, $C_{1-4}$ haloalkyl, and cyano.

13. A compound of claim 5, wherein the compound is of formula IVa or a stereoisomer or pharmaceutically acceptable salt thereof:

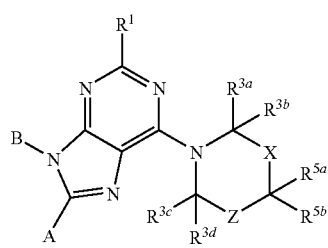

wherein:
$R^{5a}$ is selected from $RO_2C(CH_2)_mCHQ(CH_2)_m-$, $R_2N(O)C(CH_2)_mCHQ(CH_2)_m-$, $R_2NS(O_2)C(CH_2)_mCHQ(CH_2)_m-$, $RO_2C(CH_2)_mCHQ(CH_2)_mNHC(O)-$, $R^c{}_2NC(O)(CH_2)_mCHQ(CH_2)_mNHC(O)-$, $RO_2C(CH_2)_mCHQ(CH_2)_mNHC(O)(CH_2)_mCHQ(CH_2)_mNHC(O)-$, $R^c{}_2NC(O)(CH_2)_mCHQ(CH_2)_mNHC(O)(CH_2)_mCHQ(CH_2)_mNHC(O)-$, $RO_2C(CH_2)_mCHQ(CH_2)_mNHC(O)(CH_2)_mCHQ(CH_2)_mNHC(O)(CH_2)_mCHQ(CH_2)_mNHC(O)-$, $R^c{}_2NC(O)(CH_2)_mCHQ(CH_2)_mNHC(O)(CH_2)_mCHQ(CH_2)_mNHC(O)(CH_2)_mCHQ(CH_2)_mNHC(O)-$, $ROS(O_2)(CH_2)_mCHQ(CH_2)_mNHC(O)-$, and $R^c{}_2NS(O_2)(CH_2)_mCHQ(CH_2)_mNHC(O)-$.

14. A compound of claim 13, wherein the compound is of formula IVb or a stereoisomer or pharmaceutically acceptable salt thereof:

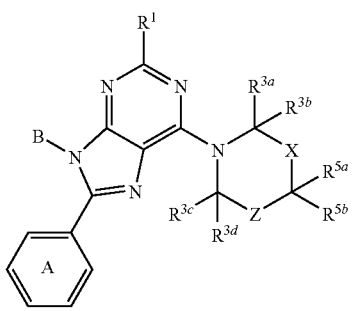

wherein:
ring A is substituted with 0-3 substituents selected from the group consisting of halo, $C_{1-4}$ alkoxy, $C_{1-4}$ alkyl, $C_{1-4}$ haloalkyl, and cyano.

15. A compound of claim 5, wherein the compound is of formula Va or a stereoisomer or pharmaceutically acceptable salt thereof:

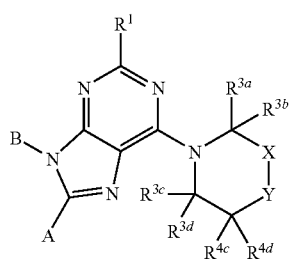

wherein:
$R^{4c}$ is selected from $RO_2C(CH_2)_mCHQ(CH_2)_m-$, $R_2N(O)C(CH_2)_mCHQ(CH_2)_m-$, $R_2NS(O_2)C(CH_2)_mCHQ(CH_2)_m-$, $RO_2C(CH_2)_mCHQ(CH_2)_mNHC(O)-$, $R^c{}_2NC(O)(CH_2)_mCHQ(CH_2)_mNHC(O)-$, $RO_2C(CH_2)_mCHQ(CH_2)_mNHC(O)(CH_2)_mCHQ(CH_2)_mNHC(O)-$, $R^c{}_2NC(O)(CH_2)_mCHQ(CH_2)_mNHC(O)(CH_2)_mCHQ(CH_2)_mNHC(O)-$, $RO_2C(CH_2)_mCHQ(CH_2)_mNHC(O)(CH_2)_mCHQ(CH_2)_mNHC(O)(CH_2)_mCHQ(CH_2)_mNHC(O)-$, $R^c{}_2NC(O)(CH_2)_mCHQ(CH_2)_mNHC(O)(CH_2)_mCHQ(CH_2)_mNHC(O)(CH_2)_mCHQ(CH_2)_mNHC(O)-$, $ROS(O_2)(CH_2)_mCHQ(CH_2)_mNHC(O)-$, and $R^c{}_2NS(O_2)(CH_2)_mCHQ(CH_2)_mNHC(O)-$.

16. A compound of claim 15, wherein the compound is of formula Vb or a stereoisomer or pharmaceutically acceptable salt thereof:

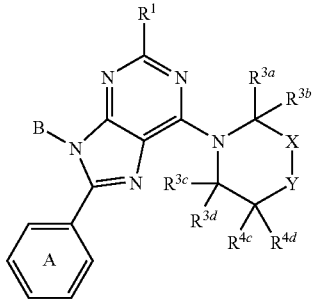

wherein:
ring A is substituted with 0-3 substituents selected from the group consisting of halo, $C_{1-4}$ alkoxy, $C_{1-4}$ alkyl, $C_{1-4}$ haloalkyl, and cyano.

17. A compound of formula VIa or a stereoisomer or pharmaceutically acceptable salt thereof:

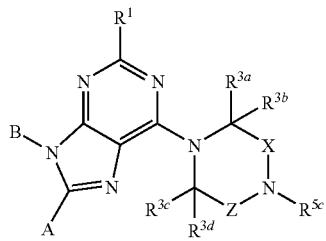

wherein:
A and B are selected from an optionally substituted aryl or an optionally substituted heteroaryl, the substituents being from one to three independently selected from halo, $C_{1-4}$ alkoxy, $C_{1-4}$ alkyl, $C_{1-4}$haloalkyl, and cyano;
X is selected from a bond, —$CH_2CH_2$— and —$C(R^{4a})(R^{4b})$—;
Z is selected from a bond, —$CH_2CH_2$— and —$C(R^{4c})(R^{4d})$—;
$R^1$ is selected from H, $C_{1-4}$ alkyl, $C_{1-4}$ haloalkyl, and $C_{1-4}$ alkoxy;
$R^{3a}$, $R^{3b}$, $R^{3c}$, $R^{3d}$, $R^{4a}$, $R^{4b}$, $R^{4c}$, and $R^{4d}$ are each independently selected from H, cyano, OH, $NH_2$, $H_2NC(O)$—, $C_{1-6}$ alkyl, $C_{1-6}$ alkoxy, $C_{1-6}$ acyloxy, $C_{1-6}$ acyl, $C_{1-3}$ alkyl-OC(O)—, $C_{1-4}$ alkyl-NHC(O)—, $(C_{1-4}$ alkyl$)_2$NC(O), $C_{1-6}$ alkylamino-, $(C_{1-4}$ alkyl$)_2$amino-, $C_{3-6}$ cycloalkylamino-, $C_{1-6}$ acylamino-, arylC$_{1-4}$ alkylamino-, heteroarylC$_{1-4}$ alkylamino-, aryl, heteroaryl, a 3-6 membered heterocycle, and a 3-8 membered carbocyclic ring, wherein the alkyl, cycloalkyl, aryl, heterocycle, and heteroaryl groups are substituted with 0-2 $R^6$;
alternatively, $R^{5a}$ and $R^{5b}$ taken together with the carbon atom to which each is attached form a ring selected from a 3-6 membered heterocyclic ring, a 5-6 membered lactone ring, and a 4-6 membered lactam ring, wherein the ring is substituted with 0-2 $R^6$ and the lactone ring and the lactam ring optionally contain an additional heteroatom selected from O, N, NR, and S;

$R^{5c}$ is selected from —$(CH_2)_mCO_2R$, —$C(O)(CH_2)_nCO_2R$, —$(CH_2)_mCONR^c{}_2$, —$C(O)(CH_2)_nCONR^c{}_2$, —$(CH_2)_mC(O)NH(CH_2)_nCO_2R$, —$(CH_2)_mC(O)NH(CH_2)_nCONR^c{}_2$, —$C(O)(CH_2)_nCONH(CH_2)_mCHQ(CH_2)_mCO_2R$, and —$C(O)(CH_2)_nCONH(CH_2)_mCHQ(CH_2)_mCONR^c{}_2$;
$R^6$ at each occurrence is independently selected from halo, —CN, OH, $C_{1-6}$ alkyl, $C_{2-6}$ alkenyl, $C_{3-8}$ cycloalkyl, $C_{1-6}$ alkoxy, $C_{1-6}$ acyl, $C_{1-6}$ acyloxy, $C_{1-6}$ alkyl-OC(O)—, $C_{1-4}$ alkyl-NHC(O)—, $(C_{1-4}$ alkyl$)_2$NC(O), $NH_2$, $C_{1-6}$ alkylamino-, $(C_{1-4}$ alkyl$)_2$amino-, $C_{3-6}$ cycloalkylamino-, $C_{1-6}$ acylamino-, $C(O)NH_2$, —$CONH(CH_2)_mCHQ(CH_2)_mCO_2R$, and —$CONH(CH_2)_mCHQ(CH_2)_mCONHR$;
alternatively, $R^{3a}$ and $R^{3b}$ taken together with $R^{3c}$ and $R^{3d}$ forms a bond, a methylene bridge, or an ethylene bridge;
alternatively, $R^{4a}$ and $R^{4b}$ taken together with $R^{3c}$ and $R^{3d}$ forms a bond, a methylene bridge, or an ethylene bridge; and,
alternatively, either $R^{4c}$ and $R^{4d}$ taken together with $R^{4a}$ and $R^{4b}$ or with $R^{3a}$ and $R^{3b}$ forms a bond, a methylene bridge, or an ethylene bridge;
Q is selected from H, OH, $C_{1-6}$ alkyl, $C_{1-6}$alkylene-OH, $(CH_2)_mNR^c{}_2$, $(CH_2)_nCONR^c{}_2$, $(CH_2)_nNHCONR^c{}_2$, $(CH_2)_mC(=NH)NH_2$, $(CH_2)_m$—$C_{3-6}$-cycloalkyl, $(CH_2)_m$-heteroaryl, and $(CH_2)_m$-aryl, wherein each aryl and heteroaryl is substituted with 0-2 groups selected from $CF_3$, halogen, $C_{1-4}$ alkyl, —CN, $CONR^c{}_2$, $NO_2$, $NR_2$, OR, $NHSO_2CH_3$, and $SONHR$;
R is independently selected from H and $C_{1-6}$ alkyl;
$R^c$ is independently selected from H, OH, alkyl, $C_{1-6}$ alkyl, $C_{2-6}$ alkenyl, arylC$_{1-4}$ alkyl- and $C_{2-6}$ alkynyl, where each alkyl may be optionally substituted with a hydroxyl group on the alkyl chain, and the aryl group is optionally substituted with 0-2 groups selected from $CF_3$, halogen, $C_{1-4}$ alkyl, —CN, $CONR_2$, $NO_2$, $NR_2$, OR, $NHSO_2CH_3$ and $SONHR$;
m is selected from 0, 1, 2, 3, and 4; and,
n is selected from 1, 2, 3, and 4.

18. A compound of claim 17, wherein the compound is of formula VIb or a stereoisomer or pharmaceutically acceptable salt thereof:

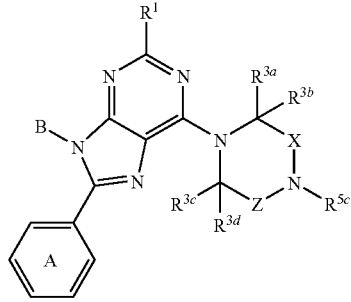

wherein:
ring A is substituted with 0-3 substituents selected from the group consisting of halo, $C_{1-4}$ alkoxy, $C_{1-4}$ alkyl, $C_{1-4}$ haloalkyl, and cyano.

19. A pharmaceutical composition, comprising: a compound of claim 1 and a pharmaceutically acceptable carrier.

20. A pharmaceutical composition, comprising: a compound of claim 3 and a pharmaceutically acceptable carrier.

21. A pharmaceutical composition, comprising: a compound of claim 5 and a pharmaceutically acceptable carrier.

22. A pharmaceutical composition, comprising: a compound of claim 17 and a pharmaceutically acceptable carrier.

23. A compound of claim 1, wherein the compound is selected from a compound of Table 2 and 3 or a pharmaceutically acceptable salt thereof.

TABLE 2

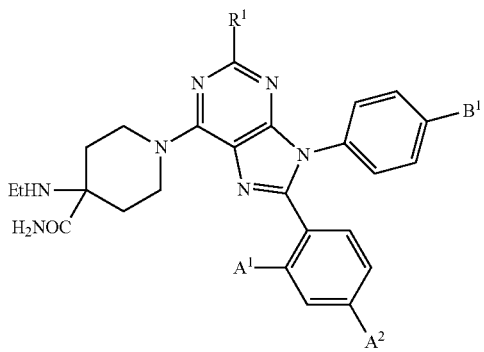

| Ex. # | A¹ | A² | R¹ | B¹ |
|---|---|---|---|---|
| 1 | Cl | H | H | OCH₂CO₂Et |
| 2 | Cl | H | H | OCH₂CO₂H |
| 3 | Cl | H | H | OCH₂CONH₂ |
| 4 | Cl | H | H | OCH₂CH=CHCO₂Et |
| 5 | Cl | H | H | OCH₂CH=CHCO₂H |
| 6 | Cl | H | H | OCH₂CH=CHCONH₂ |
| 7 | Cl | H | H | NHCOCH₂CO₂Et |
| 8 | Cl | H | H | NHCOCH₂CO₂H |
| 9 | Cl | H | H | NHCOCH₂CONH₂ |
| 10 | Cl | H | CH₃ | OCH₂CO₂Et |
| 11 | Cl | H | CH₃ | OCH₂CO₂H |
| 12 | Cl | H | CH₃ | OCH₂CONH₂ |
| 13 | Cl | H | CH₃ | OCH₂CH=CHCO₂Et |
| 14 | Cl | H | CH₃ | OCH₂CH=CHCO₂H |
| 15 | Cl | H | CH₃ | OCH₂CH=CHCONH₂ |
| 16 | Cl | H | CH₃ | NHCOCH₂CO₂Et |
| 17 | Cl | H | CH₃ | NHCOCH₂CO₂H |
| 18 | Cl | H | CH₃ | NHCOCH₂CONH₂ |
| 19 | F | Cl | H | OCH₂CO₂Et |
| 20 | F | Cl | H | OCH₂CO₂H |
| 21 | F | Cl | H | OCH₂CONH₂ |
| 22 | F | Cl | H | OCH₂CH=CHCO₂Et |
| 23 | F | Cl | H | OCH₂CH=CHCO₂H |
| 24 | F | Cl | H | OCH₂CH=CHCONH₂ |
| 25 | F | Cl | H | NHCOCH₂CO₂Et |
| 26 | F | Cl | H | NHCOCH₂CO₂H |
| 27 | F | Cl | H | NHCOCH₂CONH₂ |
| 28 | F | Cl | CH₃ | OCH₂CO₂Et |
| 29 | F | Cl | CH₃ | OCH₂CO₂H |
| 30 | F | Cl | CH₃ | OCH₂CONH₂ |
| 31 | F | Cl | CH₃ | OCH₂CH=CHCO₂Et |
| 32 | F | Cl | CH₃ | OCH₂CH=CHCO₂H |
| 33 | F | Cl | CH₃ | OCH₂CH=CHCONH₂ |
| 34 | F | Cl | CH₃ | NHCOCH₂CO₂Et |
| 35 | F | Cl | CH₃ | NHCOCH₂CO₂H |
| 36 | F | Cl | CH₃ | NHCOCH₂CONH₂ |

TABLE 3

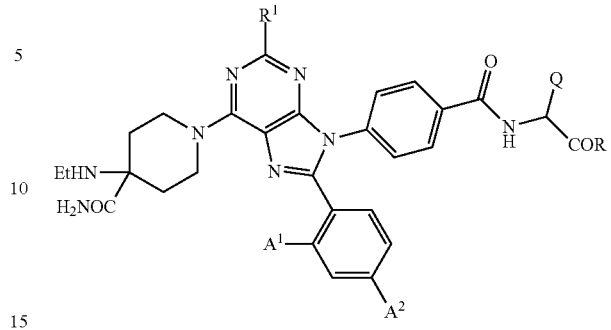

| Ex. # | A¹ | A² | R¹ | Q | R |
|---|---|---|---|---|---|
| 1 | Cl | H | H | H | OMe |
| 2 | Cl | H | H | H | OH |
| 3 | Cl | H | H | H | NH₂ |
| 4 | Cl | H | H | H | NHCH₂CO₂CH₃ |
| 5 | Cl | H | H | H | NHCH₂CO₂H |
| 6 | Cl | H | H | H | NHCH₂CONH₂ |
| 7 | Cl | H | CH₃ | H | OMe |
| 8 | Cl | H | CH₃ | H | OH |
| 9 | Cl | H | CH₃ | H | NH₂ |
| 10 | Cl | H | CH₃ | H | NHCH₂CO₂CH₃ |
| 11 | Cl | H | CH₃ | H | NHCH₂CO₂H |
| 12 | Cl | H | CH₃ | H | NHCH₂CONH₂ |
| 13 | Cl | H | H | CH₃ | OMe |
| 14 | Cl | H | H | CH₃ | OH |
| 15 | Cl | H | H | CH₃ | NH₂ |
| 16 | Cl | H | H | CH₃ | NHCH₂CO₂CH₃ |
| 17 | Cl | H | H | CH₃ | NHCH₂CO₂H |
| 18 | Cl | H | H | CH₃ | NHCH₂CONH₂ |
| 19 | Cl | H | CH₃ | CH₃ | OMe |
| 20 | Cl | H | CH₃ | CH₃ | OH |
| 21 | Cl | H | CH₃ | CH₃ | NH₂ |
| 22 | Cl | H | CH₃ | CH₃ | NHCH₂CO₂CH₃ |
| 23 | Cl | H | CH₃ | CH₃ | NHCH₂CO₂H |
| 24 | Cl | H | CH₃ | CH₃ | NHCH₂CONH₂ |
| 25 | Cl | H | H | CH₂OH | OMe |
| 26 | Cl | H | H | CH₂OH | OH |
| 27 | Cl | H | H | CH₂OH | NH₂ |
| 28 | Cl | H | H | CH₂OH | NHCH₂CO₂CH₃ |
| 29 | Cl | H | H | CH₂OH | NHCH₂CO₂H |
| 30 | Cl | H | H | CH₂OH | NHCH₂CONH₂ |
| 31 | Cl | H | CH₃ | CH₂OH | OMe |
| 32 | Cl | H | CH₃ | CH₂OH | OH |
| 33 | Cl | H | CH₃ | CH₂OH | NH₂ |
| 34 | Cl | H | CH₃ | CH₂OH | NHCH₂CO₂CH₃ |
| 35 | Cl | H | CH₃ | CH₂OH | NHCH₂CO₂H |
| 36 | Cl | H | CH₃ | CH₂OH | NHCH₂CONH₂. |

24. A compound of claim 3, wherein the compound is selected from a compound of Table 4 and 5 or a pharmaceutically acceptable salt thereof.

TABLE 4

| Ex. # | A¹ | A² | R |
|---|---|---|---|
| 1 | Cl | H | H |
| 2 | Cl | H | CH$_2$CO$_2$Me |
| 3 | Cl | H | CH$_2$CO$_2$H |
| 4 | Cl | H | CH$_2$CONH$_2$ |
| 5 | Cl | H | CHCH$_3$CO$_2$Me |
| 6 | Cl | H | CHCH$_3$CO$_2$H |
| 7 | Cl | H | CHCH$_3$CONH$_2$ |
| 8 | Cl | H | CHCH$_2$OHCO$_2$Me |
| 9 | Cl | H | CHCH$_2$OHCO$_2$H |
| 10 | Cl | H | CHCH$_2$OHCONH$_2$ |
| 11 | F | Cl | H |
| 12 | F | Cl | CH$_2$CO$_2$Me |
| 13 | F | Cl | CH$_2$CO$_2$H |
| 14 | F | Cl | CH$_2$CONH$_2$ |
| 15 | F | Cl | CHCH$_3$CO$_2$Me |
| 16 | F | Cl | CHCH$_3$CO$_2$H |
| 17 | F | Cl | CHCH$_3$CONH$_2$ |
| 18 | F | Cl | CHCH$_2$OHCO$_2$Me |
| 19 | F | Cl | CHCH$_2$OHCO$_2$H |
| 20 | F | Cl | CHCH$_2$OHCONH$_2$ |

TABLE 5

| Ex. # | n | A¹ | A² | R |
|---|---|---|---|---|
| 1 | 0 | Cl | H | NH$_2$ |
| 2 | 0 | Cl | H | NH(CH$_2$)$_3$CH(NH$_2$)CO$_2$Et |
| 3 | 0 | Cl | H | NH(CH$_2$)$_3$CH(NH$_2$)CO$_2$H |
| 4 | 0 | Cl | H | NH(CH$_2$)$_3$CH(NH$_2$)CONH$_2$ |
| 5 | 0 | Cl | H | NHCOCH$_2$CO$_2$Et |
| 6 | 0 | Cl | H | NHCOCH$_2$CO$_2$H |
| 7 | 0 | Cl | H | NHCOCH$_2$CONH$_2$ |
| 8 | 0 | Cl | H | NHCH$_2$CO$_2$Et |
| 9 | 0 | Cl | H | NHCH$_2$CO$_2$H |
| 10 | 0 | Cl | H | NHCH$_2$CONH$_2$ |
| 11 | 1 | Cl | H | NHCOCH$_2$CO$_2$Et |
| 12 | 1 | Cl | H | NHCOCH$_2$CO$_2$H |
| 13 | 1 | Cl | H | NHCOCH$_2$CONH$_2$ |
| 14 | 1 | Cl | H | NHCH$_2$CO$_2$Et |
| 15 | 1 | Cl | H | NHCH$_2$CO$_2$H |
| 16 | 1 | Cl | H | NHCH$_2$CONH$_2$ |
| 17 | 0 | F | Cl | NH(CH$_2$)$_3$CH(NH$_2$)CO$_2$Et |
| 18 | 0 | F | Cl | NH(CH$_2$)$_3$CH(NH$_2$)CO$_2$H |
| 19 | 0 | F | Cl | NH(CH$_2$)$_3$CH(NH$_2$)CONH$_2$ |
| 20 | 0 | F | Cl | NHCOCH$_2$CO$_2$Et |
| 21 | 0 | F | Cl | NHCOCH$_2$CO$_2$H |
| 22 | 0 | F | Cl | NHCOCH$_2$CONH$_2$ |
| 23 | 1 | F | Cl | NHCH$_2$CO$_2$Et |
| 24 | 1 | F | Cl | NHCH$_2$CO$_2$H |
| 25 | 1 | F | Cl | NHCH$_2$CONH$_2$ |
| 26 | 1 | F | Cl | NHCOCH$_2$CO$_2$Et |
| 27 | 1 | F | Cl | NHCOCH$_2$CO$_2$H |
| 28 | 1 | F | Cl | NHCOCH$_2$CONH$_2$ |
| 29 | 1 | F | Cl | NHCH$_2$CO$_2$Et |
| 30 | 1 | F | Cl | NHCH$_2$CO$_2$H |
| 31 | 1 | F | Cl | NHCH$_2$CONH$_2$. |

25. A compound of claim 5, wherein the compound is selected from a compound of Table 1, 6, and 7 or a pharmaceutically acceptable salt thereof.

TABLE 1

| Ex. # | A¹ | A² | R¹ | Q | R |
|---|---|---|---|---|---|
| 1 | Cl | H | H | H | OMe |
| 2 | Cl | H | H | H | OH |
| 3 | Cl | H | H | H | NH$_2$ |
| 4 | Cl | H | H | H | NHCH$_2$CO$_2$CH$_3$ |
| 5 | Cl | H | H | H | NHCH$_2$CO$_2$H |
| 6 | Cl | H | H | H | NHCH$_2$CONH$_2$ |
| 7 | Cl | H | CH$_3$ | H | OMe |
| 8 | Cl | H | CH$_3$ | H | OH |
| 9 | Cl | H | CH$_3$ | H | NH$_2$ |
| 10 | Cl | H | CH$_3$ | H | NHCH$_2$CO$_2$CH$_3$ |
| 11 | Cl | H | CH$_3$ | H | NHCH$_2$CO$_2$H |
| 12 | Cl | H | CH$_3$ | H | NHCH$_2$CONH$_2$ |
| 13 | Cl | H | H | CH$_3$ | OMe |

TABLE 1-continued

| Ex. # | A¹ | A² | R¹ | Q | R |
|---|---|---|---|---|---|
| 14 | Cl | H | H | CH₃ | OH |
| 15 | Cl | H | H | CH₃ | NH₂ |
| 16 | Cl | H | H | CH₃ | NHCH₂CO₂CH₃ |
| 17 | Cl | H | H | CH₃ | NHCH₂CO₂H |
| 18 | Cl | H | H | CH₃ | NHCH₂CONH₂ |
| 19 | Cl | H | CH₃ | CH₃ | OMe |
| 20 | Cl | H | CH₃ | CH₃ | OH |
| 21 | Cl | H | CH₃ | CH₃ | NH₂ |
| 22 | Cl | H | CH₃ | CH₃ | NHCH₂CO₂CH₃ |
| 23 | Cl | H | CH₃ | CH₃ | NHCH₂CO₂H |
| 24 | Cl | H | CH₃ | CH₃ | NHCH₂CONH₂ |
| 25 | Cl | H | H | CH₂OH | OMe |
| 26 | Cl | H | H | CH₂OH | OH |
| 27 | Cl | H | H | CH₂OH | NH₂ |
| 28 | Cl | H | H | CH₂OH | NHCH₂CO₂CH₃ |
| 29 | Cl | H | H | CH₂OH | NHCH₂CO₂H |
| 30 | Cl | H | H | CH₂OH | NHCH₂CONH₂ |
| 31 | Cl | H | CH₃ | CH₂OH | OMe |
| 32 | Cl | H | CH₃ | CH₂OH | OH |
| 33 | Cl | H | CH₃ | CH₂OH | NH₂ |
| 34 | Cl | H | CH₃ | CH₂OH | NHCH₂CO₂CH₃ |
| 35 | Cl | H | CH₃ | CH₂OH | NHCH₂CO₂H |
| 36 | Cl | H | CH₃ | CH₂OH | NHCH₂CONH₂ |
| 37 | F | Cl | H | H | OMe |
| 38 | F | Cl | H | H | OH |
| 39 | F | Cl | H | H | NH₂ |
| 40 | F | Cl | H | H | NHCH₂CO₂CH₃ |
| 41 | F | Cl | H | H | NHCH₂CO₂H |
| 42 | F | Cl | H | H | NHCH₂CONH₂ |
| 43 | F | Cl | CH₃ | H | OMe |
| 44 | F | Cl | CH₃ | H | OH |
| 45 | F | Cl | CH₃ | H | NH₂ |
| 46 | F | Cl | CH₃ | H | NHCH₂CO₂CH₃ |
| 47 | F | Cl | CH₃ | H | NHCH₂CO₂H |
| 48 | F | Cl | CH₃ | H | NHCH₂CONH₂ |
| 49 | F | Cl | H | CH₃ | OMe |
| 50 | F | Cl | H | CH₃ | OH |
| 51 | F | Cl | H | CH₃ | NH₂ |
| 52 | F | Cl | H | CH₃ | NHCH₂CO₂CH₃ |
| 53 | F | Cl | H | CH₃ | NHCH₂CO₂H |
| 54 | F | Cl | H | CH₃ | NHCH₂CONH₂ |
| 55 | F | Cl | CH₃ | CH₃ | OMe |
| 56 | F | Cl | CH₃ | CH₃ | OH |
| 57 | F | Cl | CH₃ | CH₃ | NH₂ |
| 58 | F | Cl | CH₃ | CH₃ | NHCH₂CO₂CH₃ |
| 59 | F | Cl | CH₃ | CH₃ | NHCH₂CO₂H |
| 60 | F | Cl | CH₃ | CH₃ | NHCH₂CONH₂ |
| 61 | F | Cl | H | CH₂OH | OMe |
| 62 | F | Cl | H | CH₂OH | OH |
| 63 | F | Cl | H | CH₂OH | NH₂ |
| 64 | F | Cl | H | CH₂OH | NHCH₂CO₂CH₃ |
| 65 | F | Cl | H | CH₂OH | NHCH₂CO₂H |
| 66 | F | Cl | H | CH₂OH | NHCH₂CONH₂ |
| 67 | F | Cl | CH₃ | CH₂OH | OMe |
| 68 | F | Cl | CH₃ | CH₂OH | OH |
| 69 | F | Cl | CH₃ | CH₂OH | NH₂ |
| 70 | F | Cl | CH₃ | CH₂OH | NHCH₂CO₂CH₃ |
| 71 | F | Cl | CH₃ | CH₂OH | NHCH₂CO₂H |
| 72 | F | Cl | CH₃ | CH₂OH | NHCH₂CONH₂ |

TABLE 6

| Ex. # | R¹ | A¹ | A² | R |
|---|---|---|---|---|
| 1 | H | Cl | H | H |
| 2 | H | Cl | H | CH₂CO₂Me |
| 3 | H | Cl | H | CH₂CO₂H |
| 4 | H | Cl | H | CH₂CONH₂ |
| 5 | H | Cl | H | CHCH₃CO₂Me |
| 6 | H | Cl | H | CHCH₃CO₂H |
| 7 | H | Cl | H | CHCH₃CONH₂ |
| 8 | H | Cl | H | CHCH₂OHCO₂Me |
| 9 | H | Cl | H | CHCH₂OHCO₂H |
| 10 | H | Cl | H | CHCH₂OHCONH₂ |
| 11 | H | Cl | H | CH₂CONHCH₂CO₂Me |
| 12 | H | Cl | H | CH₂CONHCH₂CO₂H |
| 13 | H | Cl | H | CH₂CONHCH₂CONH₂ |
| 14 | H | F | Cl | H |
| 15 | H | F | Cl | CH₂CO₂Me |
| 16 | H | F | Cl | CH₂CO₂H |
| 17 | H | F | Cl | CH₂CONH₂ |
| 18 | H | F | Cl | CHCH₃CO₂Me |
| 19 | H | F | Cl | CHCH₃CO₂H |
| 20 | H | F | Cl | CHCH₃CONH₂ |
| 21 | H | F | Cl | CHCH₂OHCO₂Me |
| 22 | H | F | Cl | CHCH₂OHCO₂H |
| 23 | H | F | Cl | CHCH₂OHCONH₂ |
| 24 | H | F | Cl | CH₂CONHCH₂CO₂Me |
| 25 | H | F | Cl | CH₂CONHCH₂CO₂H |
| 26 | H | F | Cl | CH₂CONHCH₂CONH₂ |
| 27 | CH₃ | Cl | H | H |
| 28 | CH₃ | Cl | H | CH₂CO₂Me |
| 29 | CH₃ | Cl | H | CH₂CO₂H |
| 30 | CH₃ | Cl | H | CH₂CONH₂ |
| 31 | CH₃ | Cl | H | CHCH₃CO₂Me |

TABLE 6-continued

| Ex. # | R¹ | A¹ | A² | R |
|---|---|---|---|---|
| 32 | $CH_3$ | Cl | H | $CHCH_3CO_2H$ |
| 33 | $CH_3$ | Cl | H | $CHCH_3CONH_2$ |
| 34 | $CH_3$ | Cl | H | $CHCH_2OHCO_2Me$ |
| 35 | $CH_3$ | Cl | H | $CHCH_2OHCO_2H$ |
| 36 | $CH_3$ | Cl | H | $CHCH_2OHCONH_2$ |
| 37 | $CH_3$ | Cl | H | $CH_2CONHCH_2CO_2Me$ |
| 38 | $CH_3$ | Cl | H | $CH_2CONHCH_2CO_2H$ |
| 39 | $CH_3$ | Cl | H | $CH_2CONHCH_2CONH_2$ |
| 40 | $CH_3$ | F | Cl | H |
| 41 | $CH_3$ | F | Cl | $CH_2CO_2Me$ |
| 42 | $CH_3$ | F | Cl | $CH_2CO_2H$ |
| 43 | $CH_3$ | F | Cl | $CH_2CONH_2$ |
| 44 | $CH_3$ | F | Cl | $CHCH_3CO_2Me$ |
| 45 | $CH_3$ | F | Cl | $CHCH_3CO_2H$ |
| 46 | $CH_3$ | F | Cl | $CHCH_3CONH_2$ |
| 47 | $CH_3$ | F | Cl | $CHCH_2OHCO_2Me$ |
| 48 | $CH_3$ | F | Cl | $CHCH_2OHCO_2H$ |
| 49 | $CH_3$ | F | Cl | $CHCH_2OHCONH_2$ |
| 50 | $CH_3$ | F | Cl | $CH_2CONHCH_2CO_2Me$ |
| 51 | $CH_3$ | F | Cl | $CH_2CONHCH_2CO_2H$ |
| 52 | $CH_3$ | F | Cl | $CH_2CONHCH_2CONH_2$ |

TABLE 7

| Ex. # | R¹ | A¹ | A² | R |
|---|---|---|---|---|
| 1 | H | Cl | H | $CH_2CO_2Me$ |
| 2 | H | Cl | H | $CH_2CO_2H$ |
| 3 | H | Cl | H | $CH_2CONH_2$ |
| 4 | H | Cl | H | $CHCH_3CO_2Me$ |
| 5 | H | Cl | H | $CHCH_3CO_2H$ |
| 6 | H | Cl | H | $CHCH_3CONH_2$ |
| 7 | H | Cl | H | $CHCH_2OHCO_2Me$ |
| 8 | H | Cl | H | $CHCH_2OHCO_2H$ |
| 9 | H | Cl | H | $CHCH_2OHCONH_2$ |
| 10 | H | Cl | H | $CH_2CONHCH_2CO_2Me$ |
| 11 | H | Cl | H | $CH_2CONHCH_2CO_2H$ |
| 12 | H | Cl | H | $CH_2CONHCH_2CONH_2$ |
| 13 | H | F | Cl | $CH_2CO_2Me$ |
| 14 | H | F | Cl | $CH_2CO_2H$ |
| 15 | H | F | Cl | $CH_2CONH_2$ |
| 16 | H | F | Cl | $CHCH_3CO_2Me$ |
| 17 | H | F | Cl | $CHCH_3CO_2H$ |
| 18 | H | F | Cl | $CHCH_3CONH_2$ |
| 19 | H | F | Cl | $CHCH_2OHCO_2Me$ |
| 20 | H | F | Cl | $CHCH_2OHCO_2H$ |
| 21 | H | F | Cl | $CHCH_2OHCONH_2$ |
| 22 | H | F | Cl | $CH_2CONHCH_2CO_2Me$ |
| 23 | H | F | Cl | $CH_2CONHCH_2CO_2H$ |
| 24 | H | F | Cl | $CH_2CONHCH_2CONH_2$ |
| 25 | $CH_3$ | Cl | H | $CH_2CO_2Me$ |
| 26 | $CH_3$ | Cl | H | $CH_2CO_2H$ |
| 27 | $CH_3$ | Cl | H | $CH_2CONH_2$ |
| 28 | $CH_3$ | Cl | H | $CHCH_3CO_2Me$ |
| 29 | $CH_3$ | Cl | H | $CHCH_3CO_2H$ |
| 30 | $CH_3$ | Cl | H | $CHCH_3CONH_2$ |
| 31 | $CH_3$ | Cl | H | $CHCH_2OHCO_2Me$ |
| 32 | $CH_3$ | Cl | H | $CHCH_2OHCO_2H$ |
| 33 | $CH_3$ | Cl | H | $CHCH_2OHCONH_2$ |
| 34 | $CH_3$ | Cl | H | $CH_2CONHCH_2CO_2Me$ |
| 35 | $CH_3$ | Cl | H | $CH_2CONHCH_2CO_2H$ |
| 36 | $CH_3$ | Cl | H | $CH_2CONHCH_2CONH_2$ |
| 37 | $CH_3$ | F | Cl | $CH_2CO_2Me$ |
| 38 | $CH_3$ | F | Cl | $CH_2CO_2H$ |
| 39 | $CH_3$ | F | Cl | $CH_2CONH_2$ |
| 40 | $CH_3$ | F | Cl | $CHCH_3CO_2Me$ |
| 41 | $CH_3$ | F | Cl | $CHCH_3CO_2H$ |
| 42 | $CH_3$ | F | Cl | $CHCH_3CONH_2$ |
| 43 | $CH_3$ | F | Cl | $CHCH_2OHCO_2Me$ |
| 44 | $CH_3$ | F | Cl | $CHCH_2OHCO_2H$ |
| 45 | $CH_3$ | F | Cl | $CHCH_2OHCONH_2$ |
| 46 | $CH_3$ | F | Cl | $CH_2CONHCH_2CO_2Me$ |
| 47 | $CH_3$ | F | Cl | $CH_2CONHCH_2CO_2H$ |
| 48 | $CH_3$ | F | Cl | $CH_2CONHCH_2CONH_2$. |

26. A compound of claim 17, wherein the compound is selected from a compound of Table 8 or a pharmaceutically acceptable salt thereof.

TABLE 8

| Ex. # | $R^1$ | $A^1$ | $A^2$ | $R^{5c}$ |
|---|---|---|---|---|
| 1 | H | Cl | H | $CH_2CO_2Me$ |
| 2 | H | Cl | H | $CH_2CO_2H$ |
| 3 | H | Cl | H | $CH_2CONH_2$ |
| 4 | H | Cl | H | $CH_2CONHCH_2CO_2Me$ |
| 5 | H | Cl | H | $CH_2CONHCH_2CO_2H$ |
| 6 | H | Cl | H | $CH_2CONHCH_2CONH_2$ |
| 7 | H | Cl | H | $COCH_2CO_2Me$ |
| 8 | H | Cl | H | $COCH_2CO_2H$ |
| 9 | H | Cl | H | $COCH_2CONH_2$ |
| 10 | H | Cl | H | $COCH_2CONHCH_2CO_2Et$ |
| 11 | H | Cl | H | $COCH_2CONHCH_2CO_2H$ |
| 12 | H | Cl | H | $COCH_2CONHCH_2CONH_2$ |
| 13 | $CH_3$ | Cl | H | $CH_2CO_2Me$ |
| 14 | $CH_3$ | Cl | H | $CH_2CO_2H$ |
| 15 | $CH_3$ | Cl | H | $CH_2CONH_2$ |
| 16 | $CH_3$ | Cl | H | $CH_2CONHCH_2CO_2Me$ |
| 17 | $CH_3$ | Cl | H | $CH_2CONHCH_2CO_2H$ |
| 18 | $CH_3$ | Cl | H | $CH_2CONHCH_2CONH_2$ |
| 19 | $CH_3$ | Cl | H | $COCH_2CO_2Me$ |
| 20 | $CH_3$ | Cl | H | $COCH_2CO_2H$ |
| 21 | $CH_3$ | Cl | H | $COCH_2CONH_2$ |
| 22 | $CH_3$ | Cl | H | $COCH_2CONHCH_2CO_2Et$ |
| 23 | $CH_3$ | Cl | H | $COCH_2CONHCH_2CO_2H$ |
| 24 | $CH_3$ | Cl | H | $COCH_2CONHCH_2CONH_2$ |
| 25 | H | F | Cl | $CH_2CO_2Me$ |
| 26 | H | F | Cl | $CH_2CO_2H$ |
| 27 | H | F | Cl | $CH_2CONH_2$ |
| 28 | H | F | Cl | $CH_2CONHCH_2CO_2Me$ |
| 29 | H | F | Cl | $CH_2CONHCH_2CO_2H$ |
| 30 | H | F | Cl | $CH_2CONHCH_2CONH_2$ |
| 31 | H | F | Cl | $COCH_2CO_2Me$ |
| 32 | H | F | Cl | $COCH_2CO_2H$ |
| 33 | H | F | Cl | $COCH_2CONH_2$ |
| 34 | H | F | Cl | $COCH_2CONHCH_2CO_2Et$ |
| 35 | H | F | Cl | $COCH_2CONHCH_2CO_2H$ |
| 36 | H | F | Cl | $COCH_2CONHCH_2CONH_2$ |
| 37 | $CH_3$ | F | Cl | $CH_2CO_2Me$ |
| 38 | $CH_3$ | F | Cl | $CH_2CO_2H$ |
| 39 | $CH_3$ | F | Cl | $CH_2CONH_2$ |
| 40 | $CH_3$ | F | Cl | $CH_2CONHCH_2CO_2Me$ |
| 41 | $CH_3$ | F | Cl | $CH_2CONHCH_2CO_2H$ |
| 42 | $CH_3$ | F | Cl | $CH_2CONHCH_2CONH_2$ |
| 43 | $CH_3$ | F | Cl | $COCH_2CO_2Me$ |
| 44 | $CH_3$ | F | Cl | $COCH_2CO_2H$ |
| 45 | $CH_3$ | F | Cl | $COCH_2CONH_2$ |
| 46 | $CH_3$ | F | Cl | $COCH_2CONHCH_2CO_2Et$ |
| 47 | $CH_3$ | F | Cl | $COCH_2CONHCH_2CO_2H$ |
| 48 | $CH_3$ | F | Cl | $COCH_2CONHCH_2CONH_2$. |

27. A pharmaceutical composition, comprising: a compound of claim 23 and a pharmaceutically acceptable carrier.

28. A pharmaceutical composition, comprising: a compound of claim 24 and a pharmaceutically acceptable carrier.

29. A pharmaceutical composition, comprising: a compound of claim 25 and a pharmaceutically acceptable carrier.

30. A pharmaceutical composition, comprising: a compound of claim 26 and a pharmaceutically acceptable carrier.

\* \* \* \* \*